(12) United States Patent
Pandey et al.

(10) Patent No.: US 11,946,078 B2
(45) Date of Patent: Apr. 2, 2024

(54) POLYPEPTIDES WITH ENDOGLUCANASE ACTIVITY AND USES THEREOF

(71) Applicant: DANISCO US INC, Palo Alto, CA (US)

(72) Inventors: Neeraj Pandey, Clapham (GB); Sina Pricelius, Leiden (NL); Annapurna Sachan, Kanpur (IN); Stepan Shipovskov, Egå (DK); Richard Bott, Kirkland, WA (US); Ajit Kumar Satapathy, Bangalore (IN)

(73) Assignee: Danisco US Inc., Palo Alto, CA (US)

( * ) Notice: Subject to any disclaimer, the term of this patent is extended or adjusted under 35 U.S.C. 154(b) by 143 days.

(21) Appl. No.: 17/237,235

(22) Filed: Apr. 22, 2021

(65) Prior Publication Data

US 2021/0309983 A1 Oct. 7, 2021

Related U.S. Application Data

(63) Continuation of application No. 16/062,911, filed as application No. PCT/US2016/067223 on Dec. 16, 2016, now abandoned.

(60) Provisional application No. 62/269,678, filed on Dec. 18, 2015.

(51) Int. Cl.
*C12N 9/24* (2006.01)
*C11D 3/386* (2006.01)
*C12N 9/42* (2006.01)
*C12N 15/63* (2006.01)

(52) U.S. Cl.
CPC ........ *C12N 9/2437* (2013.01); *C11D 3/38645* (2013.01); *C12N 9/24* (2013.01); *C12N 15/63* (2013.01); *C12Y 302/01004* (2013.01)

(58) Field of Classification Search
CPC .................................. C12N 15/63; C12N 9/24
See application file for complete search history.

(56) References Cited

U.S. PATENT DOCUMENTS

2019/0106690 A1* 4/2019 Lai ..................... D06M 16/003

FOREIGN PATENT DOCUMENTS

| CN | 105155167 A | 12/2015 |
| EP | 1700917 A1 | 9/2006 |
| EP | 1702981 A1 | 9/2006 |

OTHER PUBLICATIONS

International Search Report and Written Opinion—PCT/US2016/067223—dated Jun. 6, 2017.
EP Search Report—dated Jul. 5, 2019.

* cited by examiner

*Primary Examiner* — Tekchand Saidha

(57) ABSTRACT

Disclosed herein are cellulase variants, or active fragments thereof, and polynucleotides encoding same, where the cellulase variants, or active fragments thereof, have endoglucanase activity. Also disclosed herein are compositions comprising the cellulase variants, or active fragments thereof; vectors and/or host cells comprising the polynucleotides encoding the cellulase variants, or active fragments thereof; and methods for making and/or using the cellulase variants, or active fragments thereof and/or compositions containing same; where the cellulase variants, or active fragments thereof, have endoglucanase activity.

15 Claims, 9 Drawing Sheets

Specification includes a Sequence Listing.

```
S_coccosporum_BAG69187.1     LTFTSGPVAGKTMVVQSTSTGGDLGTNHFDLAMPGGGVGIFDGCSPQFG--GLAGDRYGGV
           STCE1-WT          LTFTSGPVAGKTMVVQSTSTGGDLGTNHFDLAMPGGGVGIFDGCSPQFG--GLAGDRYGGV
           STCE1-A142P       LTFTSGPVAGKTMVVQSTSTGGDLGTNHFDLAMPGGGVGIFDGCSPQFG--GLPGDRYGGY
M_mycetomatis_KOP50759       LTFTSGPVAGKTMVVQSTSTGGDLGSNHFDLNIPGGGVGLFDGCKNQFG--GLPGAQYGGI
T_hyrcaniae_US20150299682-0004 LTFTSGPVAGRVMVVQSTSTGGDLGTNHFDLNIPCGGVGLFDGCTPQFG--GLPGAQYGGI
C_thermophilum_AGY80101.1    LTFTSGPVAGKTMVVQSTSTGGDLGSNHFDLNIPGGGVGLFDGCTPQFG--GLPGARYGGI
M_albomyces_CAD56865         LTFTSGPVAGKTMAVQSTSTGGDLGSNHFDLNIPGGGVGLFDGCTPQFG--GLPGARYGGI
Humicola_sp_CAB42308         LTFTSGPVAGKTMVVQSTSTGGDLGSNHFDIAMPGGGVGIFDGCSPQVG--GLAGQRYGGV
T_terrestris_XP_003651003.1  LTFTSGPVAGKTMVVQSTSTGGDLGSNQFDIAMPGGGVGIFNGCSSQFG--GLPGAQYGGI
H_insolens_CAA01574          LTFTSGPVAGKTMVVQSTSTGGDLGSNHFDLNIPGGGVGIFDGCTPQFG--GLPGQRYGGI
H_grisea_BAA74956.1          LTFTSGPVAGKKMVVQSTSTGGDLGSNHFDLNIPGGGVGIFDGCTPQFG--GLPGQRYGGI
Acr_therm_ACE10216           LTFNSGPVAGKTMVVQSTSTGGDLGSNQFDLAIPGGGVGIFNGCASQFG--GLPGAQYGGI
Pod_anserina_CAP61565        LTFTDGPVAGKTMVVQSTNTGGDISNNHFDILMPGGGVGLFDGCTPQYG--GIPGAQYGGV
A_chryso_KFH43153            LTFTSGPVAGKTLVVQSTNTGYDLSNNHFDILMPGGGYGLFDGCKRPQFG--GLPGCRYGGI
N_crassa_XP_003651017        LTFNSGPASGRTMIVQSTMIVQSTNTGGDLSDNHFDLLIPGGGVGAFDGCSROYC--SIPGERYGGV
Humicola_sp_CAB42311         LTFTDGPASGRTMIVQSTNTGGDLSDNHFDLLIPGGGVGIFDGCTSQYCQALPGAQYGGV
Humicola_sp_CAB42312         LTFTSGPVAGKKMVVQSTSTGGDLGSNHFDLNIPGGGVGIFDGCTPQFG--GLPGQRYGGI
S_indonesiacum_CDF76466.1    LTFTSGPVAGKKMVVQSTSTGGDLGSNHFDLNIPGGGVGIFDGCTPQFG--GLPGQRYGGI S_coccosporum_BAG69187.1     SSRSQCDSFPAALKPGCYWRFDWFNADNPTFTFRQVQCPSELVARTGCRRNDGNFPVF
           STCE1-WT          SSRSQCDSFPAALKPGCYWRFDWFNADNPTFTFRQVQCPSELVARTGCRRNDGNFPVF
           STCE1-A142P       SSRSQCDSFPAALKPGCYWRFDWFNADNPTFTFRQVQCPDELVARTGCRRSDDANFPAF
M_mycetomatis_KOP50759       SDRSQCSSFPSQLQPGCNWRFDWFMADNPSFTFDQVQCPDELVARTGCRRSDDANFPAF
T_hyrcaniae_US20150299682-0004 SSRSQCDSFPEALKPGCYWRFDWFQNADNPTFTFERVQCPSELVARTGCRRNDSSFPVF
C_thermophilum_AGY80101.1    SSRQECDSFPEPLKPGCQWRFDWFQNADNPSFTFERVQCPEELVARTGCRRHDGGFAVF
M_albomyces_CAD56865         SSRSECDSFPAALKPGCYWRFDWFKNADNPSFSFRQVQCPAELVARTGCRRNDGNFPAV
Humicola_sp_CAB42308         SSRDQCDSFPAPLKPGCQWRFDWFQNADNPTFTFQQVQCPAEIVARSGCRRNDSSFPVF
T_terrestris_XP_003651003.1  SSRNECDRFPDALKPGCYWRFDWFKNADNPSFSFRQVQCPAELVARTGCRRNDGNFPAV
H_insolens_CAA01574          SSRNECDRFPDALKPGCYWRFDWFKNADNPSFSFRQVQCPAELVARTGCRRNDGNFPAV
H_grisea_BAA74956.1          SSRSECDRFPDALKPGCYWRFDWFKNADNPSFSFRQVQCPAELVARTGCRRNDGNFPAV
Acr_therm_ACE10216           SDRSQCSSFPAPLQPGCQWRFDWFQNADNPTFTFQRVQCPSELTSRTGCKRDDDASYPVF
Pod_anserina_CAP61565        SDRSQCASFPDALKPGCCQWRFDWFQNADNPNLNFEQVQCPSELTARSGCKRDDSRFPVF
A_chryso_KFH43153            SSREECBQMPEAIKAGCQWRYDWFKNADNPSFTFRQVQCPSELTARSGCKRDDSRFPVF
N_crassa_XP_003651017        TSRDQCDQMPSALKQGCYWRFDWFKNADNPSFTFRQVQCPSELTSRTGCKRNDSQFPVF
Humicola_sp_CAB42311         SSRAECDQMPEAIKAGCQWRYDWFKNADNPSFTFRQVQCPSETTAISGCTRSDDGNFPAA
Humicola_sp_CAB42312         SSRNECERFPDALKPGCYWRFDWFKNADNPNSFRQVQCPAELVARTGCRRNDGNFPAV
S_indonesiacum_CDF76466.1    SSRNECERFPDALKPGCYWRFDWFKNADNPNSFRQVQCPAELVARTGCRRNDGNFPAV
```

FIG 6B

| Name | | | SEQ ID |
|---|---|---|---|
| S_coccosporum_BAC69187.1 | TPPSGG--QSSSSSSSSSAKPTSTSTSTSTSTKATSTSTSTASSQTSSSTGGCAAQRWAQC | GGIGFSGCTTCVSGTTCNKQNDWYSQCL------ | SEQ ID NO:1 |
| STCE1-WT | TPPSGG--QSSSSSSSSSAKPTSTSTSTSTSTKATSTSTSTASSQTSSSTGGCAAQRWAQC | GGIGFSGCTTCVSGTTCNKQNDWYSQCL------ | SEQ ID NO:5 |
| STCE1-A142P | TPPSGG--QSSSSSSSSSAKPTSTSTSTSTSTKATSTSTSTASSQTSSSTGGCAAQRWAQC | GGIGFSGCTTCVSGTTCNKQNDWYSQCL------ | SEQ ID NO:8 |
| M_mycetomatis_KOP50759 | SPPSRL------------------------------------------------------ | GGIGFSGCTTCVSGTTCNKQNDWYSQCL------ | SEQ ID NO:2 |
| T_hyrceaniae_US20150209682-0004 | TPGTSG-----SSSTAKPASSSIRAT-----STKTSAPAIQTSSTGGCVAQKWAQC | GGSGFPSGCTTCAAGSTCTRQNDYYSQCL------ | SEQ ID NO:18 |
| C_thermophilum_AGY80101.1 | TPPSGD-----SPSSSSAAPTSTSTSQQPQQPTSSSSQASVPTSNPGGCTSQKWAQC | GGIGFTGCTTCVSGTTCTKLNDWYSQCTMINL | SEQ ID NO:19 |
| M_albomyces_CAD56065 | KAPSA--------------TSSPVNQPTSTSTT-------STSTTSSPPVGPTTPSGCTAERWAQC | GGSGFSGCTTCVAGSTCTKINDWYHQCL------ | SEQ ID NO:20 |
| Humicola_sp_CAB42308 | TPPSGG------------NGGTGTP-------TSTAPGSCQTSPGGGSGCTSQHWAQC | GGIGFSGCTTCVSGTTCTKINDWYHQCL------ | SEQ ID NO:21 |
| T_terrestris_XP_003651003.1 | QIPSSS-------------TSSPVNQPTSTSTT-------STSTTSSPPVQPTTPSCCTAERWAQC | GGNGWSGCTTCVAGSTCTKINDWYHQCL------ | SEQ ID NO:22 |
| H_insolens_CAA01574 | TPPSGG-------------TSSPVGQPTSTSTT-------STSTTSSPPVQPTTPSCCTAERWAQC | GGNGWSGCTTCVAGSTCTKINDWYHQCL------ | SEQ ID NO:10 |
| H_grisea_BAA74936.1 | QIPSSS-------------TSSPVNQPTSTSTT-------STSTTSSPPVQPTTPSCCTAERWAQC | GGIGYGCTNCVAGTICTQLNPWYSQCL------ | SEQ ID NO:23 |
| Acr_therm_ACE10216 | NPPSVPGLDGSNPGNPTTTVVPPASTSTS-----RPTSSTSSPVSTPTCQPGGCTTQKWQGC | GGQGFTGCTTCEAGSTCTKINDWYHQCL------ | SEQ ID NO:24 |
| Pod_anserina_CAP61565 | SPPGGG-------------SQPQPQPT-------------SSAAQNPNTPSAAPGGCRAAKYAQC | GGSGWSGCTNCPS&STCKTINDYYHKCA | SEQ ID NO:25 |
| A_chryso_KFH43153 | --------------------G---------------SNPSTPTTPPSSGGSGCTADKYAQC | GGNGWSGCTTCVAGSTCTKINDWYHQCL------ | SEQ ID NO:26 |
| N_crassa_XP957107 | TPPSGG-------------TSSPVNQPTSTSTT-------STSTTSSPPVQPTTPSGCTAERWAQC | GGNGWSGCTTCVAGSTCTKINDWYHQCL------ | SEQ ID NO:13 |
| Humicola_sp_CAB42311 | QIPSSS-------------TSSPVNQPTSTSTT-------STSTTSSPPVQPTTPSCCTAERWAQC | GGNGWSGCTTCVAGSTCTKINDWYHQCL------ | SEQ ID NO:27 |
| Humicola_sp_CAB42312 | QIPSSS-------------TSSPVNQPTSTSTT-------STSTTSSPPVQPTTPSCCTAERWAQC | GGNGWSGCTTCVAGSTCTKINDWYHQCL------ | SEQ ID NO:28 |
| S_indonesiacum_CDF76466.1 | QIPSSS-------------TSSPRIQNLGSTRM-------LSRSRRRRP---------A | GGSQLAAAGGVRGGAP------ | SEQ ID NO:29 |

FIG 6C

```
                            1             10            20            30            40            50
                            |             |             |             |             |             |
STCE1-WT      (SEQ ID NO:5)  A--DGKSTRYWDCCKPSCCSWPGKASVNQPVFACSANFQRISDPNVKSGCD-GGSAYACAD
H. insolens   (SEQ ID NO:11) A--DGRSTRYWDCCKPSCCSWSGCGWAKKAPVNQPVFSCNANFQRITDFDAKSGCEPGGVAYSCAD
N. crassa     (SEQ ID NO:14) ASGSGQSTRYWDCCKPSCCSWSGKAPVNRPVLACDANNNPLSDASVKSGCD-GGSAYTCAN
T. terrestris (SEQ ID NO:17) ASGSGQSTRYWDCCKPSCCAWPGKAAVSQPVYACDANFQRLSDFNVQSGCN-GGSAYSCAD 60            70            80            90           100           110
                            |             |             |             |             |             |
STCE1-WT      (SEQ ID NO:5)  QTPWAVNDNFSYGFAATSISGGNEASWCCGCYELTFTSGPVAGKTMVVQSTSTGGDLGTN
H. insolens   (SEQ ID NO:11) QTPWAVNDDFALGFAATSIAGSNEAGWCCACYELTFTSGPVAGKKMVVQSTSTGGDLGSN
N. crassa     (SEQ ID NO:14) NSPWAVNDQLSYGFAATKLSGGTESSWCCACYALTFTSGPVAGKTLVVQSTSTGGDLGSN
T. terrestris (SEQ ID NO:17) QTPWAVNDNLAYGFAATSIAGGSESSWCCACYALTFTSGPVAGKTMVVQSTSTGGDLGSN 120           130           140           150           160           170
                            |             |             |             |             |             |
STCE1-WT      (SEQ ID NO:5)  HFDLAMPGGGVGIFDGCSPQFGGLAGDRYGGVSSRSQCDSFPAALKPGCYWRFDWFKNAD
H. insolens   (SEQ ID NO:11) HFDLNIPGGGVGIFDGCTPQFGGLPGQRYGGISSRNECDRFPDALKPGCYWRFDWFKNAD
N. crassa     (SEQ ID NO:14) HFDINMPGGGVGLFDGCKRQFGGLPGAQYGGISSRSQCDSFPAALKPGCWRFDWFQNAD
T. terrestris (SEQ ID NO:17) HFDIAMPGGGVGIFNGCSSQFGGLPGAQYGGISSRDQCDSFPAPLKPGCQWRFDWFQNAD 180           190           200           212
                            |             |             |             |
STCE1-WT      (SEQ ID NO:5)  NPTFTFRQVQCPSELVARTGCRRNDDGNFPVFTPP
H. insolens   (SEQ ID NO:11) NPSFSFRQVQCPAELVARTGCRRNDDGNFPAVQIP
N. crassa     (SEQ ID NO:14) NPNFTFKQVQCPSELTSRTGCKRNDDSQFPVFTPP
T. terrestris (SEQ ID NO:17) NPTFTFQQVQCPAEIVARSGCKRNDDSSFPVFTPP
```

FIG 8

POLYPEPTIDES WITH ENDOGLUCANASE ACTIVITY AND USES THEREOF

CROSS-REFERENCE TO RELATED APPLICATIONS

This application is a Continuation of U.S. application Ser. No. 16/062,911, filed Jun. 15, 2018, which is a 371 of International Application No. PCT/US16/67223, filed Dec. 16, 2016 and is related to and claims the benefit of priority from U.S. Provisional Patent Application Ser. No. 62/269,678, filed Dec. 18, 2015, which is hereby incorporated herein by reference in its entirety.

REFERENCE TO SEQUENCE LISTING SUBMITTED ELECTRONICALLY

The content of the sequence listing electronically submitted with the application as an ASCII text file (Name: NB40768WOPCT_ST25; Size: 67.5 KB; Created: Dec. 6, 2016) forms part of the application and is hereby incorporated herein by reference in its entirety.

Disclosed herein are cellulase variants, or active fragments thereof, and polynucleotides encoding same, wherein the cellulase variants, or active fragments thereof, have endoglucanase activity. Also disclosed herein are compositions comprising said cellulase variants, or active fragments thereof; vectors and/or host cells comprising the polynucleotides encoding said cellulase variants, or active fragments thereof; and methods for making and/or using said cellulase variants, or active fragments thereof and/or compositions containing same; wherein said cellulase variants, or active fragments thereof, have endoglucanase activity.

Cellulase enzymes are glycoside hydrolase enzymes that catalyze the hydrolysis of beta-1,4glycosidic linkages in cellulose to break it down into monosaccharides or shorter polysaccharides and oligosaccharides. Generally, cellulase enzymes contain a cellulose binding module (CBM) and a catalytic domain that are separated by a flexible spacer known as a "linker" or "linker peptide". The catalytic domains of cellulases are classified by both the Enzyme Commission (EC) and the Glycoside Hydrolase (GH) family systems.

The Enzyme Commission has identified two classes of cellulases, the endocellulases, which are classified as EC 3.2.1.4 enzymes and also referred to as endoglucanases, and the exocellulases, which are classified as EC 3.2.1.91 enzymes and also referred to as cellobiohydrolases or exo-glucanase. The endoglucanases randomly cleave internal bonds at amorphous sites that create new chain ends, whereas the exoglucanases cleave two to four units from the ends of the exposed chains created by the endoglucanases. The GH family system, on the other hand, groups cellulases based on enzyme structure and function resulting in a number of GH Families including, for example, GH Family 5, 6, 7, 8, 9, 10, 12, 16, 18, 19, 26, 44, 45, 48, 51, 61, and 74.

Cellulases are known to be useful, for example, in detergent compositions; for treating textiles; as animal feed additives; in processing of paper and pulp for smoothing fiber, enhancing drainage and de-inking; in the food industry for extracting and clarifying juice from fruits and vegetables and for mashing; and in reducing biomass to glucose that is then fermented and distilled to make low $CO_2$ cellulosic ethanol.

Cellulases are used in the textile industry to improve the feel and/or appearance of cotton-containing fabric by, for example, removing fuzz (untangled fiber ends that protrude from the surface of yarn or fabric) and pills (bunches or balls of tangled fibers that are held to the surface of fabric by one or more fibers), and also helping to prevent pills, which make garments appear worn, from forming through subsequent consumer wash and wear cycles. This process is known as "depilling" or "biopolishing". Cellulases are also used to impart, for example, a distressed or "stonewashed" appearance to cotton-containing denim. This process is known as "bio-stoning" and has largely replaced stones for generating the soft, faded denim desired by consumers.

Cellulases are used in detergent compositions, for example, to enhance soil removal, remove pills, brighten fabric colors, and soften fabric. The detergent compositions to which cellulases are added also often contain other enzymes, such as, for example, proteases, making it important for the cellulase to be stable in the presence of these other enzymes, as well as, other detergent additives, such as, for example, surfactants. If the cellulase is not stable, the protease, for example, will degrade the cellulase over time negating the laundering benefits associated with the cellulase. As a result, there remains a need in the art for cellulases that are stable in the presence of one or more other enzyme, such as, for example, protease and/or one or more other detergent components, such as, for example, a surfactant.

DESCRIPTION OF THE DRAWINGS

FIGS. 6A-6C provides a MUSCLE multiple sequence alignment of STCE1-WT cellulase and variants thereof with other GH45 cellulases described in Example 7.

FIG. 8 provides a MUSCLE multiple sequence alignment of the catalytic domain regions of the following GH45 cellulases: STCE-1 (SEQ ID NO:5), *H. insolens* (SEQ ID NO:11), *N. crassa* (SEQ ID NO:14) and *T. terrestris* 120H (SEQ ID NO:17).

Figure 1:
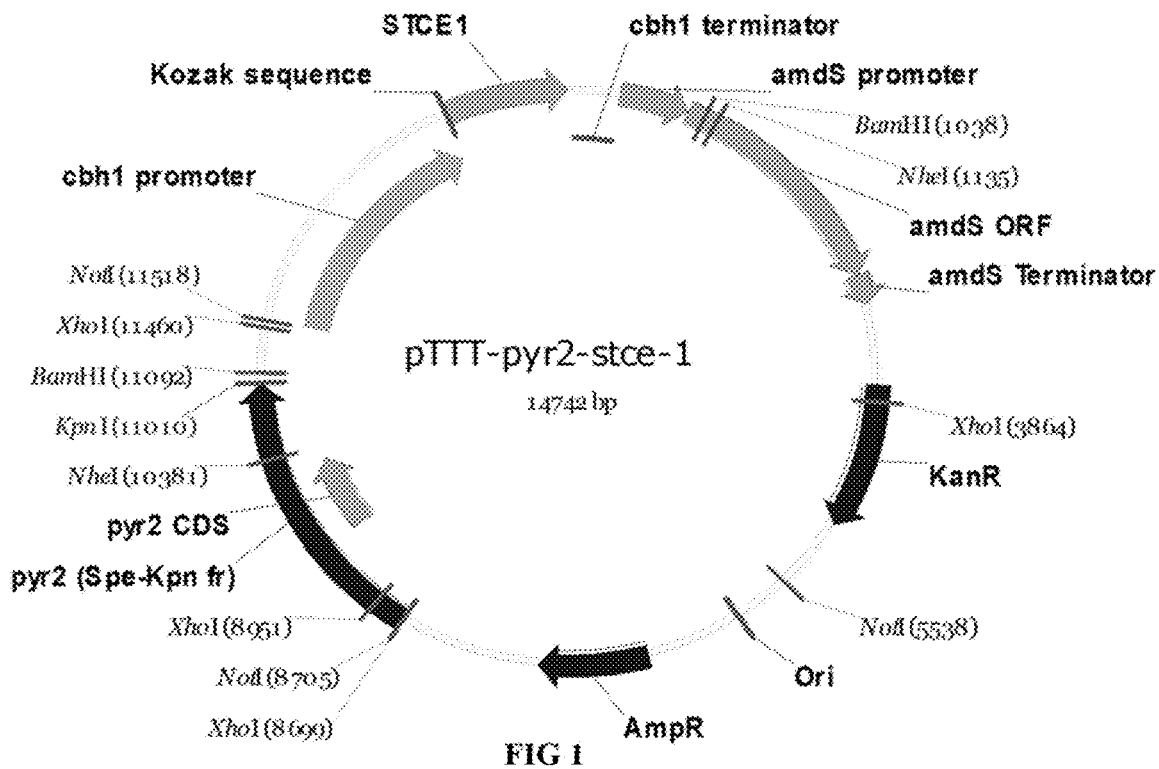
FIG. 1 provides a plasmid map of pTTT-pyr2-stce1.

One embodiment is directed to a cellulase variant, or an active fragment thereof, comprising an amino acid sequence comprising a substitution at one or more positions selected from (i) 4, 20, 23, 29, 32, 36, 44, 51, 77, 80, 87, 90, 97, 98, 99, 102, 112, 116, 135, 136, 142, 153, 154, 157, 161, 163, 192, 194, 204, 208, 210, 212, 216, 217, 221, 222, 225, 227, and 232; (ii) K4X, G/K20X, A/S23X, F29X, S32X, N/Q36X, K44X, S51X, S77X, N80X, G87X, E90X, P97X, V98X, A99X, T102X, G112X, T116X, S135X, P/S136X, A142X, G/H/S153X, Q154X, S157X, A161X, K163X, L192X, A194X, G204X, V208X, T210X, P212X, Q216X, S217X, S221X, S222X, S225X, K227X, and S232X; (iii) X4V, X20N, X23L, X29W, X32D/Y, X36T, X44V, X51T, X77K/M, X80S, X87A, X90A, X97S, X98G, X99E/Y, X102K, X112S/T/V, X116V, X135T, X136E/K/S, X142D/E/P/Q, X153D, X154E, X157D, X161E/P, X163V, X192V, X194S, X204S, X208H/K, X210V, X212S, X216D/E/G/P/S/T/V, X217G/M, X221L/M, X222A, X225K, X227R, and X232T; or (iv) K4V, G/K20L, A/S23L, F29W, S32D/Y, N/Q36T, K44V, S51T, S77K/M, N80S, G87A, E90A, P97S, V98G, A99E/Y, T102K, G112S/Y/V, T116V, S135T, P/S136E/K/S, A142D/E/P/Q, G/H/S153D, Q154E, S157D, A161E/P, K163V, L192V, A194S, G204S, V208H/K, T210V, P212S, Q216D/E/G/P/S/T/V, S217G/M, S221L/M, S222A, S225K, K227R, and S232T, wherein said variant has endoglucanase activity, and wherein the amino acid positions of the variant, or active fragment thereof are numbered by correspondence with the amino acid sequence of SEQ ID NO:5. Another embodiment is directed to a cellulase variant, or active fragment thereof, wherein said variant comprises an amino acid sequence having at least 70%, 75%, 80%, 82%, 85%, 90%, 91%, 92%, 93%, 94%, 95%, 96%, 97%, 98%, or 99% amino acid sequence identity to the amino acid sequence of SEQ ID NO:5, 11, 14, 17, 22, or amino acids 1-215 of SEQ ID NO:5. In another embodiment, the cellulase variant, or active fragment thereof is derived from a parent or reference polypeptide selected from SEQ ID NOs:5, 11, 14, 17, and 22. In still yet another embodiment, the cellulase variant, or active fragment thereof is a family GH45 cellulase.

In one embodiment, the cellulase variant, or active fragment thereof, has one or more improved property selected from improved thermostability, improved stability in the presence of one or more other enzyme, and improved stability in the presence of one or more other enzyme and one or more other detergent component. In another embodiment, the other enzyme is protease and/or the other detergent component is a surfactant. In some embodiments, the improved property is improved when compared to a parent or reference polypeptide. In other embodiments, the parent or reference polypeptide comprises an amino acid sequence having at least 70%, 75%, 80%, 82% 85%, 90%, 91%, 92%, 93%, 94%, 95%, 96%, 97%, 98%, or 99% amino acid sequence identity to the amino acid sequence of SEQ ID NO:5,11, 14, 17, 22, or amino acids 1-215 of SEQ ID NO:5. In still other embodiments, the parent or reference polypeptide comprises SEQ ID NO:5 or amino acids 1-215 of SEQ ID NO:5.

A further embodiment is directed to a composition comprising said cellulase variant, or active fragment thereof; a vector and/or host cell comprising said cellulase variant, or active fragment thereof; and a method for making and/or using said variant, or active fragment thereof and/or said compositions containing such variants, or active fragments thereof; wherein said cellulase variant, or active fragment thereof, has endoglucanase activity.

The features of the cellulase variants described herein make them well-suited for use in detergent compositions, textile processing, paper and pulp processing, and other industrial applications, such as, for example, to impart soil release or fabric care benefits and/or improve the feel and/or appearance of a cotton-containing fabric.

The following terms are defined for clarity. Terms not defined should be accorded their ordinary meaning as used in the art. For example, technical and scientific terms not defined herein have the same meaning as commonly understood by one of ordinary skill in the art (See, e.g., Singleton and Sainsbury, *Dictionary of Microbiology and Molecular Biology*, 2d Ed., John Wiley and Sons, N Y 1994; and Hale and Marham, *The Harper Collins Dictionary of Biology*, Harper Perennial, N Y 1991).

The singular terms "a," "an," and "the" include the plural reference unless the context clearly indicates otherwise.

The term "about" when used in connection with a numerical value refers to a range of −10% to +10% of the numerical value. For instance, the phrase a "pH value of about 6" refers to pH values of from 5.4 to 6.6.

The term "adjunct ingredient" when used in conjunction with a detergent or fabric care composition means any liquid, solid or gaseous material selected for the particular type of detergent or fabric care composition desired and the form of the product (e.g., liquid, granule, powder, bar, paste, spray, tablet, gel, unit dose, sheet, or foam composition), which materials are also preferably compatible with the cellulase variant or active fragment thereof used in the composition. In some embodiments, granular compositions are in "compact" form, while in other embodiments, the liquid compositions are in a "concentrated" form.

The term "cellulase variant" refers to a recombinant polypeptide that is derived from a parent or reference polypeptide by the substitution, addition, or deletion, of one or more amino acids. A cellulase variant may differ from a parent polypeptide by a small number of amino acid residues and may be defined by their level of primary amino acid sequence homology/identity with a parent polypeptide. For example, a cellulase variant has at least 70%, 75%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity with a parent (or reference) polypeptide.

The terms "detergent composition" and "detergent formulation" refer to mixtures of chemical ingredients intended for use in a wash medium to clean soiled objects. Detergent compositions/formulations may include, for example, one or more surfactant, hydrolytic enzyme, oxido-reductase, builder, bleaching agent, bleach activator, bluing agent, fluorescent dye, caking inhibitor, masking agent, enzyme activator, antioxidant, chelant, polymer, foam regulator, fragrance, and solubilizer.

The term "derived from" encompasses the terms "originated from," "obtained from," "obtainable from," "isolated from," and "created from" and generally indicates that one specified material find its origin in another specified material or has features that can be described with reference to the another specified material.

The term "effective amount" when used in conjunction with a cellulase variant or active fragment thereof refers to the quantity of cellulase variant or active fragment thereof needed to achieve the desired level of endoglucanase activity in the specified application or detergent or fabric care composition. Such effective amounts are readily ascertained by one of ordinary skill in the art and are based on many factors, such as the particular cellulase variant or active fragment thereof that is used, the application, the specific composition of the cleaning composition (including the particular protease contained therein), and whether a liquid or dry (e.g., granular, bar, powder, solid, liquid, tablet, gel, paste, foam, sheet, or unit dose) composition is required.

The term "endoglucanase" refers to an endo-1,4-(1,3;1,4)-beta-D-glucan 4-glucanohydrolase (E.C. 3.2.1.4), which catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D- glucans or xyloglucans, and other plant material containing cellulosic components. Endoglucanase activity can be determined according to the procedure described in the examples.

The term "expression vector" refers to a DNA construct containing a DNA sequence that encodes the specified polypeptide and is operably linked to a suitable control sequence capable of effecting the expression of the polypeptides in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself.

The term "fabric" refers to, for example, woven, knit, and non-woven material, as well as staple fibers and filaments that can be converted to, for example, yarns and woven, knit, and non-woven fabrics. The term encompasses material made from natural, as well as synthetic (e.g., manufactured) fibers.

The terms "fabric care composition" or "fabric care formulation" refer to a composition/formulation containing a cellulase variant, or active fragment thereof, described herein that will, when added to a wash medium, remove pills and/or fuzz from fabric; brighten fabric colors; and/or soften fabric.

The term "family GH45" refers to a polypeptide that is classified as glycoside hydrolase Family 45 according to Henrissat B., 1991, A classification of glycosyl hydrolases based on amino-acid sequence similarities, *Biochem.* 1 280: 309-316, and Henrissat and Bairoch, 1996, Updating the sequence-based classification of glycosyl hydrolases, *Biochem. J.* 316: 695-696 and classified based on structure and function relationships CMin the Carbohydrate-Active enZYmes Database, CAZy (URL: http://afmb.cnrs-mrs.fr/~cazy/CAZY/index.html).

The term "host cells" generally refers to prokaryotic or eukaryotic hosts which are transformed or transfected with vectors constructed using recombinant DNA techniques known in the art. Transformed host cells are capable of either replicating vectors encoding the protein variants or expressing the desired protein variant. In the case of vectors which encode the pre- or pro-form of the protein variant, such variants, when expressed, are typically secreted from the host cell into the host cell medium.

The term "hybridization" refers to the process by which a strand of nucleic acid joins with a complementary strand through base pairing, as known in the art.

The term "hybridization conditions" refers to the conditions under which hybridization reactions are conducted. These conditions are typically classified by degree of "stringency" of the conditions under which hybridization is measured. The degree of stringency can be based, for example, on the melting temperature ($T_m$) of the nucleic acid binding complex or probe. For example, "maximum stringency" typically occurs at about $T_m$–5° C. (5° below the $T_m$ of the probe); "high stringency" at about 5-10° C. below the $T_m$; "intermediate stringency" at about 10-20° C. below the $T_m$ of the probe; and "low stringency" at about 20-25° C. below the $T_m$. Alternatively, or in addition, hybridization conditions can be based upon the salt or ionic strength conditions of hybridization and/or one or more stringency washes, e.g., 6×SSC=very low stringency; 3×SSC=low to medium stringency; 1×SSC=medium stringency; and 0.5×SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe. For applications requiring high selectivity, it is typically desirable to use relatively stringent conditions to form the hybrids (e.g., relatively low salt and/or high temperature conditions are used).

The term "introduced" in the context of inserting a nucleic acid sequence into a cell, means transformation, transduction, or transfection. Means of transformation include protoplast transformation, calcium chloride precipitation, electroporation, naked DNA, and the like as known in the art. (See, Chang and Cohen [1979] *Mol. Gen. Genet.* 168:111-115; Smith et al. [1986] *Appl. Env. Microbiol.* 51:634; and the review article by Ferrari et al., in Harwood, *Bacillus*, Plenum Publishing Corporation, pp. 57-72, 1989).

A nucleic acid or polynucleotide is "isolated" when it is at least partially or completely separated from other components, including but not limited to, for example, other proteins, nucleic acids, and cells. Similarly, a polypeptide, protein or peptide is "isolated" when it is at least partially or completely separated from other components, including but not limited to, for example, other proteins, nucleic acids, and cells. On a molar basis, an isolated species is more abundant than are other species in a composition. For example, an isolated species may comprise at least about 60%, 65%, 70%, 75%, 80%, 85%, 90%, 91%, 92%, 93%, 94%, 95%, 96%, 97%, 98%, 99%, or 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a nucleic acid or a protein sample, respectively, followed by visualization upon staining. If desired, a high-resolution technique, such as high performance liquid chromatography (HPLC) or a similar means can be utilized for purification of the material.

The term "other detergent component" refers to a non-enzyme component that is added to a detergent composition or formulation, such as, for example, a surfactant, oxidoreductase, builder, bleaching agent, bleach activator, bluing agent, fluorescent dye, caking inhibitor, masking agent, enzyme activator, antioxidant, chelant, polymer, foam regulator, fragrance, and solubilizer.

The term "other enzyme" refers to a second, third, fourth, etc enzyme that is added to a detergent composition, wherein the first enzyme is a cellulase variant, or active fragment thereof described herein. Examples of other enzymes include, for example, acyl transferases, amylases, alpha-amylases, beta-amylases, alpha-galactosidases, arabinases, arabinosidases, aryl esterases, beta-galactosidases, beta-glucanases, carrageenases, catalases, chondroitinases, cutinases, endo-beta-mannanases, exo-beta-mannanases, esterases, exo-mannanases, galactanases, glucoamylases, hemicellulases, hyaluronidases, keratinases, laccases, lactases, ligninases, lipases, lipolytic enzymes, lipoxygenases, mannanases, metalloproteases, oxidases, pectate lyases, pectin acetyl esterases, pectinases, pentosanases, perhydrolases, peroxidases, phenoloxidases, phosphatases, phospholipases, phytases, polygalacturonases, proteases, pullulanases, reductases, rhamnogalacturonases, second cellulase, beta-glucanases, tannases, transglutaminases, xylan acetyl-esterases, xylanases, xylosidases, and combinations thereof.

The terms "polynucleotide" encompasses DNA, RNA, heteroduplexes, and synthetic molecules capable of encoding a polypeptide. Nucleic acids may be single-stranded or double-stranded, and may have chemical modifications. The terms "nucleic acid" and "polynucleotide" are used interchangeably. Because the genetic code is degenerate, more than one codon may be used to encode a particular amino acid, and the present compositions and methods encompass nucleotide sequences which encode a particular amino acid sequence. Unless otherwise indicated, nucleic acid sequences are presented in a 5'-to-3' orientation.

The term "polypeptide" refers to a molecule comprising a plurality of amino acids linked through peptide bonds. The terms "polypeptide," "peptide," and "protein" are used interchangeably. Proteins may optionally be modified (e.g., glycosylated, phosphorylated, acylated, farnesylated, prenylated, and sulfonated) to add functionality. Where such amino acid sequences exhibit activity, they may be referred to as an "enzyme". The conventional one-letter or three-letter codes for amino acid residues are used, with amino acid sequences being presented in the standard amino-to-carboxy terminal orientation (i.e., N→C).

The term "recombinant," refers to genetic material (i.e., nucleic acids, the polypeptides they encode, and vectors and cells comprising such polynucleotides) that has been modified to alter its sequence or expression characteristics, such as, for example, by mutating the coding sequence to produce an altered polypeptide, fusing the coding sequence to that of another gene, placing a gene under the control of a different promoter, expressing a gene in a heterologous organism, expressing a gene at a decreased or elevated level, and expressing a gene conditionally or constitutively in manner different from its natural expression profile. Generally recombinant nucleic acids, polypeptides, and cells based thereon, have been manipulated by man such that they are not identical to related nucleic acids, polypeptides, and/or cells found in nature.

The term "second cellulase" refers to a second cellulase enzyme that is added to a detergent composition, wherein the first cellulase enzyme is a cellulase variant, or active fragment thereof described herein. This second cellulase enzyme, includes, for example, cellobiohydrolases, endoglucanases, xyloglucanases, and combinations thereof.

The term "signal sequence" refers to a sequence of amino acids bound to the N-terminal portion of a polypeptide, and which facilitates the secretion of the mature form of the protein from the cell. The mature form of the extracellular protein lacks the signal sequence which is cleaved off during the secretion process.

The term "surfactant" refers to any compound generally recognized in the art as having surface active qualities. Surfactants can include, for example, anionic, cationic, nonionic, and zwitterionic compounds, which are further described, herein.

The terms "thermostability" and "thermostable" refer to cellulase variants that retain a specified amount of endoglucanase activity after exposure to elevated temperatures over a given period of time under conditions prevailing during cleaning, textile treatment, or other process, for example, while exposed to elevated temperatures. In some embodiments, the one or more cellulase variant retains at least about 50%, about 60%, about 70%, about 75%, about 80%, about 85%, about 90%, about 92%, about 95%, about 96%, about 97%, about 98%, or about 99% endoglucanase activity after exposure to elevated temperatures, for example, at least about 50° C., about 55° C., about 60° C., about 65° C., or about 70° C., over a given time period, for example, at least about 10 minutes, about 30 minutes, about 60 minutes, about 120 minutes, about 180 minutes, about 240 minutes, about 300 minutes, etc.

The term "variant polynucleotide" refers to a polynucleotide that encodes a cellulase variant, has a specified degree of homology/identity with a parent polynucleotide, or hybridizes under stringent conditions to a parent polynucleotide or the complement, thereof. For example, a variant polynucleotide has at least 70%, 75%, 80%, 81%, 82%, 83%, 84%, 85%, 86%, 87%, 88%, 89%, 89%, 90%, 91%, 92%, 93%, 94%, 95%, 96%, 97%, 98%, or 99% nucleotide sequence identity with a parent polynucleotide.

The terms, "wild-type" or "parental" with respect to a polypeptide, refer to a naturally-occurring polypeptide that does not include a man-made substitution, insertion, or deletion at one or more amino acid positions. Similarly, the terms "wild-type" or "parental,", with respect to a polynucleotide, refer to a naturally-occurring polynucleotide that does not include a man-made substitution, insertion, or deletion at one or more nucleosides. A polynucleotide encoding a wild-type or parental polypeptide is, however, not limited to a naturally-occurring polynucleotide, and encompasses any polynucleotide encoding the wild-type or parental polypeptide.

The term "naturally-occurring" refers to anything (e.g., polypeptide or nucleic acid sequences) that is found in nature. Conversely, the term "non-naturally occurring" refers to anything that is not found in nature (e.g., recombinant nucleic acids and polypeptide sequences produced in the laboratory or modifications of the wild-type sequence).

The term "reference", with respect to a polypeptide, refers to a naturally-occurring polypeptide that does not include a man-made substitution, insertion, or deletion at one or more amino acid positions, as well as a naturally-occurring or synthetic polypeptide that includes one or more man-made substitutions, insertions, or deletions at one or more amino acid positions. Similarly, the term "reference", with respect to a polynucleotide, refers to a naturally-occurring polynucleotide that does not include a man-made substitution, insertion, or deletion of one or more nucleosides, as well as a naturally-occurring or synthetic polynucleotide that includes one or more man-made substitutions, insertions, or deletions at one or more nucleosides. For example, a polynucleotide encoding a wild-type or parental polypeptide is not limited to a naturally-occurring polynucleotide, and encompasses any polynucleotide encoding the wild-type or parental polypeptide.

The amino acid substitutions described herein use one or more following nomenclatures: position or starting amino acid:position:substituted amino acid(s). Reference to only a position encompasses any starting amino acid that may be present in a reference polypeptide, parent or wild-type molecule at that position and any amino acid with which such starting amino acid may be substituted (i.e., amino acid substitutions exclude the starting amino acid of such reference polypeptide, parent or wild-type molecule). Reference to a substituted amino acid or a starting amino acid may be further expressed as several substituted amino acids or several starting amino acids separated by a foreslash ("/"). For example, X130A/N-209-213 represents a three amino acid substitution combination, wherein X is any starting amino acid at position 130 that can be substituted with an alanine (A) or an asparagine (N); 209 represents a position where any starting amino acid can be substituted with an amino acid that is not the starting amino acid; and 213 represents a position where any starting amino acid can be substituted with an amino acid that is not the starting amino acid. By way of further example, E/Q/S101F/G/H/T/V represents five possible substitutions at position 101, wherein the starting amino acid glutamate (E), glutamine (Q), or serine (S) can be substituted with a phenylalanine (F), glycine (G), histidine (H), threonine (T), or valine (V).

Sequence identity may be determined using known programs such as BLAST, ALIGN, and CLUSTAL using standard parameters. (See, e.g., Altschul et al. [1990] *J. Mol. Biol.* 215:403-410; Henikoff et al. [1989] *Proc. Natl. Acad. Sci. USA* 89:10915; Karin et al. *Proc. Natl. Acad. Sci USA* 90:5873; and Higgins et al. [1988] *Gene* 73:237-244). Software for performing BLAST analyses is publicly available through the National Center for Biotechnology Information (NCBI). Databases may also be searched using FASTA (Pearson et al. [1988] *Proc. Natl. Acad. Sci. USA* 85:2444-2448). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another useful algorithm for comparison of multiple protein sequences is the MUSCLE program from Geneious software (Biomatters Ltd.) (Robert C. Edgar. MUSCLE: multiple sequence alignment with high accuracy and high throughput Nucl. Acids Res. (2004) 32 (5): 1792-1797).

One embodiment is directed to a cellulase variant, or an active fragment thereof, comprising an amino acid sequence comprising a substitution at one or more positions selected from: (i) 4, 20, 23, 29, 32, 36, 44, 51, 77, 80, 87, 90, 97, 98, 99, 102, 112, 116, 135, 136, 142, 153, 154, 157, 161, 163, 192, 194, 204, 208, 210, 212, 216, 217, 221, 222, 225, 227, and 232; (ii) K4X, G/K20X, A/S23X, F29X, S32X, N/Q36X, K44X, S51X, S77X, N80X, G87X, E90X, P97X, V98X, A99X, T102X, G112X, T116X, S135X, P/S136X, A142X, G/H/S153X, Q154X, S157X, A161X, K163X, L192X, A194X, G204X, V208X, T210X, P212X, Q216X, S217X, S221X, S222X, S225X, K227X, and S232X; (iii) X4V, X20N, X23L, X29W, X32D/Y, X36T, X44V, X51T, X77K/M, X80S, X87A, X90A, X97S, X98G, X99E/Y, X102K, X112S/T/V, X116V, X135T, X136E/K/S, X142D/E/P/Q, X153D, X154E, X157D, X161E/P, X163V, X192V, X194S, X204S, X208H/K, X210V, X212S, X216D/E/G/P/S/T/V, X217G/M, X221L/M, X222A, X225K, X227R, and X232T; or (iv) K4V, G/K20L, A/S23L, F29W, S32D/Y, N/Q36T, K44V, S51T, S77K/M, N80S, G87A, E90A, P97S, V98G, A99E/Y, T102K, G112S/Y/V, T116V, S135T, P/S136E/K/S, A142D/E/P/Q, G/H/S153D, Q154E, S157D, A161E/P, K163V, L192V, A194S, G204S, V208H/K, T210V, P212S, Q216D/E/G/P/S/T/V, S217G/M, S221L/M, S222A, S225K, K227R, and S232T, where the variant has endoglucanase activity and the amino acid positions of the variant, or active fragment thereof, are numbered by correspondence with the amino acid sequence of SEQ ID NO:5. Another embodiment is directed to a cellulase variant, or an active fragment thereof, comprising an amino acid sequence comprising a substitution at one or more positions selected from: (i) 4, 20, 23, 29, 32, 36, 44, 51, 77, 80, 87, 90, 97, 98, 99, 102, 112, 116, 135, 136, 153, 154, 157, 161, 163, 192, 194, 204, 208, 210, 212, 217, 221, 222, 225, 227, and 232; (ii) K4X, G/K20X, A/S23X, F29X, S32X, N/Q36X, K44X, S51X, S77X, N80X, G87X, E90X, P97X, V98X, A99X, T102X, G112X, T116X, S135X, P/S136X, G/H/5153X, Q154X, S157X, A161X, K163X, L192X, A194X, G204X, V208X, T210X, P212X, S217X, S221X, S222X, S225X, K227X, and S232X; (iii) X4V, X20N, X23L, X29W, X32D/Y, X36T, X44V, X51T, X77K/M, X80S, X87A, X90A, X97S, X98G, X99E/Y, X102K, X112S/T/V, X116V, X135T, X136E/K/S, X153D, X154E, X157D, X161E/P, X163V, X192V, X194S, X204S, X208H/K, X210V, X212S, X217G/M, X221L/M, X222A, X225K, X227R, and X232T; or (iv) K4V, G/K20L, A/S23L, F29W, S32D/Y, N/Q36T, K44V, S51T, S77K/M, N80S, G87A, E90A, P97S, V98G, A99E/Y, T102K, G112S/Y/V, T116V, S135T, P/S136E/K/S, G/H/S153D, Q154E, S157D, A161E/P, K163V, L192V, A194S, G204S, V208H/K, T210V, P212S, S217G/M, S221L/M, S222A, S225K, K227R, and S232T, where the variant has endoglucanase activity and the amino acid positions of the variant, or active fragment thereof, are numbered by correspondence with the amino acid sequence of SEQ ID NO:5.

Another embodiment is directed to a cellulase variant, or active fragment thereof, wherein said variant comprises an amino acid sequence having at least 70%, 75%, 80%, 82%, 85%, 90%, 91%, 92%, 93%, 94%, 95%, 96%, 97%, 98%, or 99% amino acid sequence identity to the amino acid sequence of SEQ ID NO:5, 11, 14, 17, 22, or amino acids 1-215 of SEQ ID NO:5.

Another further embodiment is directed to a cellulase variant, or an active fragment thereof, comprising an amino acid sequence comprising a substitution at one or more positions selected from: (i) 142 and 216; (ii) A142X and Q216X; (iii) X142D/E/P/Q and X216D/E/G/P/S/T/V; or (iv) A142D/E/P/Q, and Q216D/E/G/P/S/T/V, where the variant has endoglucanase activity and the amino acid positions of the variant, or active fragment thereof, are numbered by correspondence with the amino acid sequence of SEQ ID NO:5. A still further embodiment is directed to a cellulase variant, or an active fragment thereof, comprising an amino acid sequence comprising a substitution at one or more positions selected from 142 and 216, where the variant has endoglucanase activity and the amino acid positions of the variant, or active fragment thereof, are numbered by correspondence with the amino acid sequence of SEQ ID NO:5. Another still further embodiment is directed to a cellulase variant, or an active fragment thereof, comprising an amino acid sequence comprising a substitution at one or more positions selected from A142X and Q216X, where the variant has endoglucanase activity and the amino acid positions of the variant, or active fragment thereof, are numbered by correspondence with the amino acid sequence of SEQ ID NO:5. An even still further embodiment is directed to a cellulase variant, or an active fragment thereof, comprising an amino acid sequence comprising a substitution at one or more positions selected from X142D, X142E, X142P, X142Q, X216D, X216E, X216G, X216P, X216S, X216T, and X216V, where the variant has endoglucanase activity and the amino acid positions of the variant, or active fragment thereof are numbered by correspondence with the amino acid sequence of SEQ ID NO:5. A yet even still further embodiment is directed to a cellulase variant, or an active fragment thereof, comprising an amino acid sequence comprising a substitution at one or more positions selected from A142D, A142E, A142P, A142Q, Q216D, Q216E, Q216G, Q216P, Q216S, Q216T, and Q216V, where the variant has endoglucanase activity and the amino acid positions of the variant, or active fragment thereof, are numbered by correspondence with the amino acid sequence of SEQ ID NO:5. A still even further embodiment is directed to a cellulase variant, or an active fragment thereof, comprising an amino acid sequence comprising a substitution at position (i) 142, (ii) 216, or (iii) 142 and 216, where the variant has endoglucanase activity and the amino acid positions of the variant, or active fragment thereof, are numbered by correspondence with the amino acid sequence of SEQ ID NO:5.

Another embodiment is directed to a cellulase variant, or an active fragment thereof, comprising an amino acid sequence comprising a substitution at position 142, where the variant has endoglucanase activity and the amino acid positions of the variant, or active fragment thereof, are numbered by correspondence with the amino acid sequence of SEQ ID NO:5. A further embodiment is directed to a cellulase variant, or an active fragment thereof, comprising an amino acid sequence comprising a substitution at position 142X, where the variant has endoglucanase activity and the amino acid positions of the variant, or active fragment thereof, are numbered by correspondence with the amino acid sequence of SEQ ID NO:5. A still further embodiment is directed to a cellulase variant, or an active fragment thereof, comprising an amino acid sequence comprising a substitution at position X142D, X142E, X142P, or X142Q, where the variant has endoglucanase activity and the amino acid positions of the variant, or active fragment thereof are numbered by correspondence with the amino acid sequence of SEQ ID NO:5. A yet even still further embodiment is directed to a cellulase variant, or an active fragment thereof, comprising an amino acid sequence comprising a substitution at position A142D, A142E, A142P, or A142Q, where the variant has endoglucanase activity and the amino acid positions of the variant, or active fragment thereof, are numbered by correspondence with the amino acid sequence of SEQ ID NO:5.

A further embodiment is directed to a cellulase variant, or an active fragment thereof, comprising an amino acid sequence comprising a substitution at position 216, where the variant has endoglucanase activity and the amino acid positions of the variant, or active fragment thereof, are numbered by correspondence with the amino acid sequence of SEQ ID NO:5. Another embodiment is directed to a cellulase variant, or an active fragment thereof, comprising an amino acid sequence comprising a substitution at position Q216X, where the variant has endoglucanase activity and the amino acid positions of the variant, or active fragment thereof, are numbered by correspondence with the amino acid sequence of SEQ ID NO:5. A still further embodiment is directed to a cellulase variant, or an active fragment thereof, comprising an amino acid sequence comprising a substitution at position X216D, X216E, X216G, X216P, X216S, X216T, or X216V, where the variant has endoglucanase activity and the amino acid positions of the variant, or active fragment thereof are numbered by correspondence with the amino acid sequence of SEQ ID NO:5. A yet even still further embodiment is directed to a cellulase variant, or an active fragment thereof, comprising an amino acid sequence comprising a substitution at position Q216D, Q216E, Q216G, Q216P, Q216S, Q216T, or Q216V, where the variant has endoglucanase activity and the amino acid positions of the variant, or active fragment thereof, are numbered by correspondence with the amino acid sequence of SEQ ID NO:5.

In another embodiment, the cellulase variant, or an active fragment thereof, comprises an amino acid sequence comprising a substitution at positions 142 and 216, where the variant has endoglucanase activity and the amino acid positions of the variant, or active fragment thereof, are numbered by correspondence with the amino acid sequence of SEQ ID NO:5. Another embodiment is directed to a cellulase variant, or an active fragment thereof, comprising an amino acid sequence comprising a substitution at positions A142X and Q216X, where the variant has endoglucanase activity and the amino acid positions of the variant, or active fragment thereof, are numbered by correspondence with the amino acid sequence of SEQ ID NO:5. A still further embodiment is directed to a cellulase variant, or an active fragment thereof, comprising an amino acid sequence comprising a substitution at positions 142 and 216, wherein position 142 is selected from X142D, X142E, X142P, and X142Q, where the variant has endoglucanase activity and the amino acid positions of the variant, or active fragment thereof are numbered by correspondence with the amino acid sequence of SEQ ID NO:5. An even still further embodiment is directed to a cellulase variant, or an active fragment thereof, comprising an amino acid sequence comprising a substitution at positions 142 and 216, wherein position 216 is selected from X216D, X216E, X216G, X216P, X216S, X216T, and X216V, where the variant has endoglucanase activity and the amino acid positions of the variant, or active fragment thereof, are numbered by correspondence with the amino acid sequence of SEQ ID NO:5. An even still yet further embodiment is directed to a cellulase variant, or an active fragment thereof, comprising an amino acid sequence comprising an amino acid sequence comprising a substitution at positions 142 and 216, wherein position 142 is selected from A142D, A142E, A142P, and A142Q, where the variant has endoglucanase activity and the amino acid positions of the variant, or active fragment thereof, are numbered by correspondence with the amino acid sequence of SEQ ID NO:5. In yet another embodiment, the cellulase variant, or an active fragment thereof, comprises an amino acid sequence comprising a substitution at positions 142 and 216, wherein position 216 is selected from Q216D, Q216E, Q216G, Q216P, Q216S, Q216T, and Q216V, where the variant has endoglucanase activity and the amino acid positions of the variant, or active fragment thereof, are numbered by correspondence with the amino acid sequence of SEQ ID NO:5. In a further embodiment, the cellulase variant, or active fragment thereof, comprises an amino acid sequence comprising a substitution at positions 142 and 216, wherein position 142 is selected from X142D, X142E, X142P, and X142Q and position 216 is selected from X216D, X216E, X216G, X216P, X216S, X216T, and X216V, where the variant has endoglucanase activity and the amino acid positions of the variant, or active fragment thereof are numbered by correspondence with the amino acid sequence of SEQ ID NO:5. In a still further embodiment, the cellulase variant, or active fragment thereof, comprises an amino acid sequence comprising a substitution at positions 142 and 216, wherein position 142 is selected from A142D, A142E, A142P, and A142Q and position 216 is selected from Q216D, Q216E, Q216G, Q216P, Q216S, Q216T, and Q216V, where the variant has endoglucanase activity and the amino acid positions of the variant, or active fragment thereof are numbered by correspondence with the amino acid sequence of SEQ ID NO:5.

In another embodiment, the cellulase variant, or active fragment thereof, describe herein is derived from a parent or reference polypeptide selected from SEQ ID NOs:5, 11, 14, 17, and 22. In a further embodiment, the cellulase variant, or active fragment thereof, describe herein is derived from a parent or reference polypeptide selected from SEQ ID NOs:11, 14, 17, and 22. In yet another embodiment, the cellulase variant, or active fragment thereof, describe herein is derived from the parent polypeptide of SEQ ID NO:5. In a still further embodiment, the cellulase variant, or active fragment thereof, describe herein is derived from the reference polypeptide of amino acids 1-215 of SEQ ID NO:5. In an even still further embodiment, the cellulase variant, or active fragment thereof, describe herein is derived from the parent polypeptide of SEQ ID NO:11. In still another embodiment, the cellulase variant, or active fragment thereof, describe herein is derived from the parent polypeptide of SEQ ID NO:14. In yet still another embodiment, the cellulase variant, or active fragment thereof, describe herein is derived from the parent polypeptide of SEQ ID NO:17 or 22.

In a further embodiment, the cellulase variant, or active fragment thereof, has one or more improved property selected from improved thermostability, improved stability in the presence of one or more other enzyme, and improved stability in the presence of one or more other enzyme and one or more other detergent component. In another embodiment, the other enzyme is protease and/or the other detergent component is a surfactant. In some embodiments, the improved property is improved when compared to a parent or reference polypeptide. In other embodiments, the parent polypeptide comprises an amino acid sequence having at least 70%, 75%, 80%, 82%, 85%, 90%, 91%, 92%, 93%, 94%, 95%, 96%, 97%, 98%, or 99% amino acid sequence identity to the amino acid sequence of SEQ ID NO:5, 11, 14, 17, or 22. In still other embodiments, the parent polypeptide comprises an amino acid sequence having at least 70%, 80%, 85%, 90%, 91%, 92%, 93%, 94%, 95%, 96%, 97%, 98%, or 99% amino acid sequence identity to the amino acid sequence of SEQ ID NO:5. In further embodiments, the parent polypeptide comprises an amino acid sequence having at least 70%, 80%, 85%, 90%, 91%, 92%, 93%, 94%, 95%, 96%, 97%, 98%, or 99% amino acid sequence identity to the amino acid sequence of SEQ ID NO:11. In yet further embodiments, the parent polypeptide comprises an amino acid sequence having at least 70%, 80%, 85%, 90%, 91%, 92%, 93%, 94%, 95%, 96%, 97%, 98%, or 99% amino acid sequence identity to the amino acid sequence of SEQ ID NO:14. In still further embodiments, the parent polypeptide comprises an amino acid sequence having at least 70%, 80%, 85%, 90%, 91%, 92%, 93%, 94%, 95%, 96%, 97%, 98%, or 99% amino acid sequence identity to the amino acid sequence of SEQ ID NO:17 or 22. In yet other embodiments, the reference polypeptide comprises an amino acid sequence having at least 70%, 80%, 85%, 90%, 91%, 92%, 93%, 94%, 95%, 96%, 97%, 98%, or 99% amino acid sequence identity to amino acids 1-215 of SEQ ID NO:5. In still other embodiments, the parent polypeptide comprises SEQ ID NO:5. In yet other embodiments, the parent polypeptide comprises SEQ ID NO:11. In still other embodiments, the parent polypeptide comprises SEQ ID NO:14. In even still other embodiments, the parent polypeptide comprises SEQ ID NO:17 or 22. In yet still other embodiments, the reference polypeptide comprises amino acids 1-215 of SEQ ID NO:5.

In other embodiments, the improved property is improved thermostability, and the variant, or active fragment thereof, has a thermal PI that is greater than 1 or 1.1. In still other embodiments, the improved property is improved stability in the presence of one or more protease, and the variant, or active fragment thereof, has a PI that is greater than 1, 1.1, 1.5, or 2.0 when the stability of said variant, or active fragment thereof is tested in the presence of said protease. In an even further embodiment, the improved property is improved stability in the presence of one or more protease and one or more other detergent component, and wherein said variant, or active fragment thereof, has a PI that is greater than 1, 1.1, 1.5, 2.0, or 2.5 when the stability of said variant, or active fragment thereof is tested in the presence of said protease and said other detergent component. In yet a further embodiment, the PI is measured in accordance with the Cellulase Activity Assay of Example 1.

In one other embodiment, the cellulase variant, or active fragment thereof comprises an amino acid sequence having at least 70%, 75%, 80%, 82%, 85%, 90%, 91%, 92%, 93%, 94%, 95%, 96%, 97%, 98%, or 99% amino acid sequence identity to the amino acid sequence of SEQ ID NO:5 or to amino acids 1-215 of SEQ ID NO:5. In a further embodiment, the cellulase variant, or active fragment thereof, comprises an amino acid sequence having at least 70% amino acid sequence identity to the amino acid sequence of SEQ ID NO:5, with the proviso that the substitution is not A142P or Q216T and the further proviso that (i) when the substitution is Q216S the cellulase variant, or active fragment thereof, does not comprise CN103343111-0003, CN103343111-0005, AGY80101, US20150299682-0004, or WO2007071818-0012; or (ii) when the substitution is Q216G the cellulase variant, or active fragment thereof, does not comprise WO2014138983-0859. In yet a further embodiment, the cellulase variant, or active fragment thereof, comprises an amino acid sequence having at least 70% amino acid sequence identity to the amino acid sequence of SEQ ID NO:5, with the proviso that the substitution is not A142P and is not Q216T and the further proviso that (i) when the substitution is Q216S the cellulase variant, or active fragment thereof, does not comprise CN103343111-0003, CN103343111-0005, AGY80101, US20150299682-0004, or WO2007071818-0012; or (ii) when the substitution is Q216G the cellulase variant, or active fragment thereof, does not comprise WO2014138983-0859. In a still further embodiment, the cellulase variant, or active fragment thereof comprises an amino acid sequence having at least 75% amino acid sequence identity to the amino acid sequence of SEQ ID NO:5, with the proviso that when (i) the substitution is A142P the cellulase variant, or active fragment thereof, does not comprise WO2012089024-0002, WO9804663-AAW46618, GB2479462-AZN28533, WO2007071820-0019, CN103343111-0005, CN103343111-0003, US20150299682-0004, AGY80101, KOP50759, or CAD56665; ii) when the substitution is Q216T the cellulase variant, or active fragment thereof, does not comprise WO9743409-0066; or iii) when the substitution is Q216S the cellulase variant, or active fragment thereof, does not comprise CN103343111-0005, CN103343111-0003, US20150299682-0004, or AGY80101. In yet still another embodiment, the cellulase variant or active fragment thereof comprises an amino acid sequence having at least 80% amino acid sequence identity to the amino acid sequence of SEQ ID NO:5, with the proviso that when (i) the substitution is A142P the cellulase variant, or active fragment thereof, does not comprise WO2012089024-0002, WO9804663-AAW46618, GB2479462-AZN28533, WO2007071820-0019, or CN103343111-0005; or ii) when the substitution is Q216S the cellulase variant, or active fragment thereof, does not comprise CN103343111-0005. In an even still further embodiment, the cellulase variant or active fragment thereof comprises an amino acid sequence having at least 85%, 90%, 91%, 92%, 93%, 94%, 95%, 96%, 97%, 98%, or 99% amino acid sequence identity to the amino acid sequence of SEQ ID NO:5.

In a further embodiment, the cellulase variant, or active fragment thereof comprises an amino acid sequence having at least 82% amino acid sequence identity to amino acids 1-215 of SEQ ID NO:5, with the proviso that (i) when the substitution is A142P the cellulase variant, or active fragment thereof, does not comprise US20150299682-0004, CN103343111-0005, AGY80101, WO2012089024-0004, WO2012089024-0002, WO2004053039-0003, XP_003651003, CDF76465, or XP_001903789; ii) when the substitution is A142G the cellulase variant, or active fragment thereof, does not comprise XP_001226436; iii) when the substitution is Q216T the cellulase variant, or active fragment thereof, does not comprise WO9743409-0066; or iv) when the substitution is Q216S the cellulase variant, or active fragment thereof, does not comprise US20150299682-0004, CN103343111-0005, or AGY80101. In a still further embodiment, the cellulase variant, or active fragment thereof, comprises an amino acid sequence having at least 85% amino acid sequence identity to amino acids 1-215 of SEQ ID NO:5, with the proviso that (i) when the substitution is A142P or Q216S the cellulase variant, or active fragment thereof, does not comprise US20150299682-0004, CN103343111-0005, or AGY80101; or ii) when the substitution is A142G the cellulase variant, or active fragment thereof, does not comprise XP_001226436. In yet an even still further embodiment, the cellulase variant, or active fragment thereof, comprises an amino acid sequence having at least 90%, 91%, 92%, 93%, 94%, 95%, 95%, 97%, 98%, or 99% amino acid sequence identity to amino acids 1-215 of SEQ ID NO:5.

In one embodiment, the cellulase variants, or active fragments thereof, described herein are family GH45 cellulases. In some embodiments, the cellulase variants, or active fragments thereof, described herein are isolated.

Further embodiments are directed to a polynucleotide that encodes the cellulase variants, or active fragments thereof, described herein. In one embodiment, the polynucleotide is contained in an expression vector contained in a heterologous organism. The polynucleotide may be operably-linked to regulatory elements (e.g., a promoter, terminator, and enhancer) to assist in expressing the encoded cellulase variants, or active fragments thereof, described herein. In some embodiments, the cellulase variant, or active fragment thereof, described herein is expressed in a heterologous organism as a secreted polypeptide, in which case, the compositions and method encompass a method for expressing the variant or active fragment thereof as a secreted polypeptide in a heterologous organism.

DNA that encodes a cellulase variant, or active fragment thereof, described herein can be chemically synthesized from published sequences or obtained directly from host cells harboring the gene (e.g., by cDNA library screening or PCR amplification).

Further embodiments are directed to methods of producing a cellulase variant, or active fragment thereof, described herein comprising: stably transforming a host cell with an expression vector comprising a polynucleotide encoding the cellulase variant, or active fragment thereof; culturing the transformed host cell under suitable conditions to produce the cellulase variant, or active fragment thereof; and recovering the cellulase variant, or active fragment thereof.

In other embodiments, a cellulase variant, or active fragment thereof, described herein is fused to a signal peptide for directing the extracellular secretion of the variant, or active fragment thereof. For example, in certain embodiments, the signal peptide is the native signal peptide of the cellulase variant, or active fragment thereof described herein. In other embodiments, the signal peptide is a non-native signal peptide such as the *B. subtilis* AprE signal peptide.

In some embodiments, the host cell in which the cellulase variant, or active fragment thereof, described herein is expressed in a heterologous organism, i.e., an organism other than *Staphylotrichum* spp. Exemplary heterologous organisms, include, for example, *B. subtilis, B. licheniformis, B. lentus, B. brevis, Geobacillus* (formerly *Bacillus*) *stearothermophilus, B. alkalophilus, B. amyloliquefaciens, B. coagulans, B. circulans, B. lautus, B. megaterium, B. thuringiensis, S. lividans, S. murinus, P. fluorescens, P. stutzerei, P. mirabilis, R. eutropha, S. carnosus, L. lactis, E. coli,* yeast (such as, for example, *Saccharomyces* spp. or *Schizosaccharomyces* spp., e.g. *S. cerevisiae*), *C. lucknowense*, and filamentous fungi such as *Aspergillus* spp., e.g., *A. oryzae* or *A. niger, H. grisea, H. insolens,* and *T. reesei*. Methods for transforming nucleic acids into these organisms are well known in the art. A suitable procedure for transformation of *Aspergillus* host cells is described, for example, in EP238023. A suitable procedure for transformation of *Trichoderma* host cells is described, for example, in Steiger et al 2011, *Appl. Environ. Microbiol.* 77:114-121.

In some embodiments, the polynucleotide that encodes the cellulase variant, or active fragment thereof has at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to the amino acid sequence of SEQ ID NO:3. In some embodiments, the polynucleotide is codon-optimized for expression in a different host, mutated to introduce cloning sites, or otherwise altered to add functionality.

In some embodiments, expression vectors are provided in a heterologous host cell suitable for expressing the cellulase variant, or active fragment thereof, described herein, or suitable for propagating the expression vector prior to introducing it into a suitable host cell. In some embodiments, the polynucleotide is included in an expression cassette and/or cloned into a suitable expression vector by standard molecular cloning techniques. Such expression cassettes or vectors contain sequences that assist initiation and termination of transcription (e.g., promoters and terminators), and generally contain a selectable marker In some embodiments, a polynucleotide that encodes a cellulase variant, or active fragment thereof, hybridizes to the polynucleotide of SEQ ID NO:3 or the complement thereof under specified hybridization conditions. The term "hybridization" refers to the process by which a strand of nucleic acid joins with a complementary strand through base pairing, as known in the art. The term "hybridization conditions" refers to the conditions under which hybridization reactions are conducted. These conditions are typically classified by degree of "stringency" of the conditions under which hybridization is measured. The degree of stringency can be based, for example, on the melting temperature ($T_m$) of the nucleic acid binding complex or probe. For example, "maximum stringency" typically occurs at about $T_m$–5° C. (5° below the $T_m$ of the probe); "high stringency" at about 5-10° C. below the $T_m$; "intermediate stringency" at about 10-20° C. below the $T_m$ of the probe; and "low stringency" at about 20-25° C. below the $T_m$. Alternatively, or in addition, hybridization conditions can be based upon the salt or ionic strength conditions of hybridization and/or one or more stringency washes, e.g., 6×SSC=very low stringency; 3×SSC=low to medium stringency; 1×SSC=medium stringency; and 0.5×SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe. For applications requiring high selectivity, it is typically desirable to use relatively stringent conditions to form the hybrids (e.g., relatively low salt and/or high temperature conditions are used).

A further embodiment is directed to a composition comprising one or more cellulase variant, or active fragment thereof, describe herein. In another embodiment, the composition is selected from an enzyme composition, detergent composition, and fabric care composition. In some embodiments, the composition is an enzyme composition. In other embodiments, the composition is a detergent composition. In still other embodiments, the composition is a fabric care composition. In yet other embodiments, the detergent composition is a laundry detergent. In still other embodiments, the laundry detergent is selected from heavy-duty liquid (HDL) laundry detergent and heavy-duty dry (HDD) granular laundry detergent.

In some further embodiments, the composition is in a form selected from a powder, liquid, granular, bar, solid, semi-solid, gel, paste, emulsion, tablet, capsule, unit dose, sheet, and foam. In even further embodiments, the composition is in a form selected from a liquid, powder, granulated solid, tablet, sheet, and unit dose. In some embodiments, the compositions described herein are provided in unit dose form, including tablets, capsules, sachets, pouches, sheets, and multi-compartment pouches. In some embodiments, the unit dose format is designed to provide controlled release of the ingredients within a multi-compartment pouch (or other unit dose format). Suitable unit dose and controlled release formats are known in the art (See e.g., EP2100949, EP2100947, WO02/102955, WO04/111178, WO2013/165725, and U.S. Pat. Nos. 4,765,916 and 4,972,017). In some embodiments, the unit dose form is provided by tablets wrapped with a water-soluble film or water-soluble pouches.

In yet even further embodiments, the composition contains phosphate or is phosphate-free and/or contains boron or is boron-free. In still other embodiments, the composition contains phosphate. In yet still other embodiments, the composition is phosphate-free. In even still further embodiments, the composition contains boron. In yet even still further embodiments, the composition is boron-free.

In yet other embodiments, the composition further comprises (i) one or more other enzymes selected from acyl transferases, amylases, alpha-amylases, beta-amylases, alpha-galactosidases, arabinases, arabinosidases, aryl esterases, beta-galactosidases, beta-glucanases, carrageenases, catalases, chondroitinases, cutinases, endo-beta-mannanases, exo-beta-mannanases, esterases, exo-mannanases, galactanases, glucoamylases, hemicellulases, hyaluronidases, keratinases, laccases, lactases, ligninases, lipases, lipolytic enzymes, lipoxygenases, mannanases, metalloproteases, oxidases, pectate lyases, pectin acetyl esterases, pectinases, pentosanases, perhydrolases, peroxidases, phenoloxidases, phosphatases, phospholipases, phytases, polygalacturonases, proteases, pullulanases, reductases, rhamnogalacturonases, second cellulase, beta-glucanases, tannases, transglutaminases, xylan acetyl-esterases, xylanases, and xylosidases; (ii) one or more surfactants; (iii) one or more ions selected from calcium and zinc; (iv) one or more adjunct ingredients; (v) one or more stabilizers; (vi) from about 0.001% to about 5.0 weight % of the cellulase variant, or active fragment thereof, described herein; (vii) one or more bleaching agents; or (viii) combinations thereof.

In still further embodiments, the composition comprises one or more other enzyme. In yet still further embodiments, the one or more other enzyme is selected from acyl transferases, amylases, alpha-amylases, beta-amylases, alpha-galactosidases, arabinases, arabinosidases, aryl esterases, beta-galactosidases, beta-glucanases, carrageenases, catalases, chondroitinases, cutinases, endo-beta-mannanases, exo-beta-mannanases, esterases, exo-mannanases, galactanases, glucoamylases, hemicellulases, hyaluronidases, keratinases, laccases, lactases, ligninases, lipases, lipolytic enzymes, lipoxygenases, mannanases, metalloproteases, oxidases, pectate lyases, pectin acetyl esterases, pectinases, pentosanases, perhydrolases, peroxidases, phenoloxidases, phosphatases, phospholipases, phytases, polygalacturonases, proteases, pullulanases, reductases, rhamnogalacturonases, second cellulase, beta-glucanases, tannases, transglutaminases, xylan acetyl-esterases, xylanases, and xylosidases. In further embodiments, the compositions described herein further comprise a protease, mannanase, and/or amylase.

In some embodiments, the composition further comprises one or more surfactant. In some other embodiments, the surfactant is selected from non-ionic, ampholytic, semi-polar, anionic, cationic, zwitterionic, and combinations and mixtures thereof. In yet still other embodiments, the surfactant is selected from anionic, cationic, nonionic, and zwitterionic compounds. In some embodiments, the composition comprises from about 0.1% to about 60%, about 1% to about 50%, or about 5% to about 40% surfactant by weight of the composition. Exemplary surfactants include, but are not limited to sodium dodecylbenzene sulfonate, C12-14 pareth-7, C12-15 pareth-7, sodium C12-15 pareth sulfate, C14-15 pareth-4, sodium laureth sulfate (e.g., Steol CS-370), sodium hydrogenated cocoate, $C_{12}$ ethoxylates (Alfonic 1012-6, Hetoxol LA7, Hetoxol LA4), sodium alkyl benzene sulfonates (e.g., Nacconol 90G), and combinations and mixtures thereof. Anionic surfactants include but are not limited to linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. Nonionic surfactants include but are not limited to alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, polyhydroxy alkyl fatty acid amide (e.g., as described in WO92/06154), polyoxyethylene esters of fatty acids, polyoxyethylene sorbitan esters (e.g., TWEENs), polyoxyethylene alcohols, polyoxyethylene isoalcohols, polyoxyethylene ethers (e.g., TRITONs and BRIJ), polyoxyethylene esters, polyoxyethylene-p-tert-octylphenols or octylphenyl-ethylene oxide condensates (e.g., NONIDET P40), ethylene oxide condensates with fatty alcohols (e.g., LUBROL), polyoxyethylene nonylphenols, polyalkylene glycols (SYNPERONIC F108), sugar-based surfactants (e.g., glycopyranosides, thioglycopyranosides), and combinations and mixtures thereof.

In a further embodiment, the detergent compositions disclosed herein further comprise a surfactant mixture that includes, but is not limited to 5-15% anionic surfactants, <5% nonionic surfactants, cationic surfactants, phosphonates, soap, enzymes, perfume, butylphenyl methylptopionate, geraniol, zeolite, polycarboxylates, hexyl cinnamal, limonene, cationic surfactants, citronellol, and benzisothiazolinone.

In other embodiments, the composition further comprises one or more calcium and/or zinc ions.

In still other embodiments, the composition further comprises one or more adjunct ingredients. In yet other embodiments, the adjunct ingredient is selected from a bleach activator, bleach catalyst, enzyme stabilizing system, chelant, optical brightener, soil release polymer, dye transfer agent, dye transfer inhibiting agent, catalytic material, hydrogen peroxide, sources of hydrogen peroxide, preformed peracids, polymeric dispersing agent, clay soil removal agent, structure elasticizing agent, dispersant, suds suppressor, dye, perfume, colorant, filler salt, hydrotrope, photoactivator, fluorescer, fabric conditioner, hydrolyzable surfactant, solvent, preservative, anti-oxidant, anti-shrinkage agent, anti-wrinkle agent, germicide, fungicide, color speckle, anti-corrosion agent, alkalinity source, solubilizing agent, carrier, processing aid, perfume, pigment, and pH control agents (See, e.g., U.S. Pat. Nos. 6,610,642; 6,605,458; 5,705,464; 5,710,115; 5,698,504; 5,695,679; 5,686,014; and 5,646,101).

In another embodiment, the composition further comprises one or more stabilizers. In another embodiment, the stabilizer is selected from water-soluble sources of calcium and/or magnesium ions; polysaccharides; and inorganic divalent metal salts, including alkaline earth metals, such as calcium salts. In some embodiments, the enzymes employed herein are stabilized by the presence of water-soluble sources of zinc (II), calcium (II), and/or magnesium (II) ions in the finished compositions, as well as other metal ions (e.g., barium (II), scandium (II), iron (II), manganese (II), aluminum (III), tin (II), cobalt (II), copper (II), nickel (II), and oxovanadium (IV). Chlorides and sulfates also find use in some embodiments. Examples of suitable oligosaccharides and polysaccharides (e.g., dextrins) are known in the art (See, e.g., WO07/145964). In some embodiments, reversible protease inhibitors also find use, such as boron-containing compounds (e.g., borate, 4-formyl phenyl boronic acid) and/or a tripeptide aldehyde find use to further improve stability, as desired.

In yet another embodiment, the composition further comprises an effective amount of a cellulase variant, or active fragment thereof, described herein. In some embodiments, the effective amount of a cellulase variant, or active fragment thereof, is from about 0.00001% to about 10%, about 0.0001% to about 10%, about 0.001% to about 5%, about 0.001% to about 2%, or about 0.005% to about 0.5% of cellulase by weight of the composition. In other embodiments, the effective amount of cellulase variant, or active fragment thereof, is from about 0.001% to about 5.0 weight percent composition. In still other embodiments, the effective amount of cellulase variant, or active fragment thereof, is from about 0.001% to about 4.5 weight percent composition. In still yet other embodiments, the effective amount of cellulase variant, or active fragment thereof, is from about 0.001% to about 4.0 weight percent composition. In yet even other embodiments, the effective amount of cellulase variant, or active fragment thereof, is from about 0.001% to about 3.5, 3.6, 3.7, 3.8, or 3.9 weight percent composition.

In even still further embodiments, the composition further comprises one or more bleaching agents. In yet another embodiment, the bleaching agent is selected from inorganic and/or organic bleaching compound(s). Inorganic bleaches may include, but are not limited to perhydrate salts (e.g., perborate, percarbonate, perphosphate, persulfate, and persilicate salts). In some embodiments, inorganic perhydrate salts are alkali metal salts. In some embodiments, inorganic perhydrate salts are included as the crystalline solid, without additional protection, although in some other embodiments, the salt is coated. Suitable salts include, for example, those described in EP2100949.

In some embodiments, the compositions described herein further comprises one or more detergent builders or builder systems, complexing agents, polymers, foam boosters, suds suppressors, anti-corrosion agents, soil-suspending agents, anti-soil redeposition agents, dyes, bactericides, hydrotopes, optical brighteners, fabric conditioners, and perfumes.

In some embodiments, the composition described herein further comprises from about 1%, from about 3% to about 60%, or from about 5% to about 40% builder by weight of the composition. Builders may include, but are not limited to, the alkali metals, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metals, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof.

In some embodiments, the builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). Any suitable builder can find use in the compositions described herein, including those known in the art (See, e.g., EP 2100949).

In an even further embodiment, the pH of the composition is neutral to basic. The laundry compositions described herein are typically formulated such that, during use in aqueous conditions, the wash water will have a pH of from about 3.0 to about 11. Liquid products are typically formulated to have a neat pH from about 5.0 to about 9.0. Granular products are typically formulated to have a pH from about 8.0 to about 11.0. Techniques for controlling pH at recommended usage levels include the use of buffers, alkalis, acids, etc., and are well known to those skilled in the art.

The term "granular composition" refers to a conglomeration of discrete solid, macroscopic particles. Powders are a special class of granular material due to their small particle size, which makes them more cohesive and more easily suspended.

Concentrations of detergent compositions in typical wash solutions throughout the world varies from less than about 800 ppm of detergent composition ("low detergent concentration geographies"), for example about 667 ppm in Japan, to between about 800 ppm to about 2000 ppm ("medium detergent concentration geographies"), for example about 975 ppm in U.S. and about 1500 ppm in Brazil, to greater than about 2000 ppm ("high detergent concentration geographies"), for example about 4500 ppm to about 5000 ppm in Europe and about 6000 ppm in high suds phosphate builder geographies.

In some embodiments, the detergent compositions described herein may be utilized at a temperature of from about 10° C. to about 60° C., or from about 20° C. to about 60° C., or from about 30° C. to about 60° C., from about 40° C. to about 60° C., from about 40° C. to about 55° C., or all ranges within 10° C. to 60° C. In some embodiments, the detergent compositions described herein are used in "cold water washing" at temperatures of from about 10° C. to about 40° C., or from about 20° C. to about 30° C., from about 15° C. to about 25° C., from about 15° C. to about 35° C., or all ranges within 10° C. to 40° C.

As a further example, different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million (parts per million converted to grains per U.S. gallon is ppm # divided by 17.1 equals grains per gallon) of hardness minerals.

TABLE II

Water Hardness Levels

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than about 10.5 (for example about 10.5 to about 20.0) grains per gallon mixed $Ca^+/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between about 3 to about 10 grains, about 3 to about 8 grains or about 6 grains. Japanese water hardness is typically lower than North American water hardness, usually less than about 4, for example about 3 grains per gallon mixed $Ca^{2+}/Mg^{2+}$.

In some embodiments, the detergent compositions described herein further comprise a protease. In some embodiments the composition comprises from about 0.00001% to about 10% protease by weight of the composition. In another embodiment, the cleaning composition comprises from about 0.0001% to about 10%, about 0.001% to about 5%, about 0.001% to about 2%, or about 0.005% to about 0.5% protease by weight of the composition.

In one embodiment, the protease is a serine protease. Suitable proteases include those of animal, vegetable or microbial origin. In some embodiments, the protease is a microbial protease. In other embodiments, the protease is a chemically or genetically modified mutant. In another embodiment, the protease is an alkaline microbial protease or a trypsin-like protease. Exemplary alkaline proteases include subtilisins derived from, for example, *Bacillus* (e.g., subtilisin, *lentus, amyloliquefaciens*, subtilisin Carlsberg, subtilisin 309, subtilisin 147 and subtilisin 168). Exemplary additional proteases include but are not limited to those described in WO9221760, WO9523221, WO2008010925, WO09149200, WO09149144, WO09149145, WO 10056640, WO10056653, WO20100566356, WO11072099, WO201113022, WO11140364, WO 12151534, WO2015038792, WO2015089447, WO2015089441, WO2015/143360, WO2016 061438, WO2016069548, WO2016069544, WO2016069557, WO2016069563, WO2016 069569, WO2016069552, WO2016145428, WO2016183509, US Publ. No. 20080090747, U.S. Pat. Nos. 5,801,039, 5,340,735, 5,500, 364, 5,855,625, RE34606, U.S. Pat. Nos. 5,955,340, 5,700, 676, 6,312,936, 6,482,628, 8,530,219, U.S. Provisional Appl Nos. 62/331,282, 62/332,417, 62/343,618, and 62/351,649, and International Appl No. PCT/US2016/038245, as well as metalloproteases described in WO1999014341, WO1999033960, WO1999014342, WO1999 034003, WO2007044993, WO2009058303, WO2009058661, WO2014071410, WO2014 194032, WO2014194034, WO2014194054, and WO2014 194117. Exemplary proteases also include, but are not limited to trypsin (e.g., of porcine or bovine origin) and the *Fusarium* protease described in WO8906270.

Exemplary commercial proteases include, but are not limited to MAXATASE®, MAXACAL™, MAXAPEM™, OPTICLEAN®, OPTIMASE®, PROPERASE®, PURAFECT®, PURAFECT® OXP, PURAMAX™, EXCELLASE™, PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST™ (DuPont); ALCALASE®, ALCALASE® ULTRA, BLAZE®, BLAZE® EVITY®, BLAZE® EVITY® 16L, CORONASE®, SAVINASE®, SAVINASE® ULTRA, SAVINASE® EVITY®, SAVINASE® EVERTS®, PRIMASE®, DURAZYM™, POLARZYME®, OVOZYME®, KANNASE®, LIQUANASE®, LIQUANASE EVERIS®, NEUTRASE®, PROGRESS UNO®, RELASE® and ESPERASE® (Novozymes); BLAP™ and BLAP™ variants (Henkel); LAVERGY™ PRO 104 L (BASF), and KAP (*B. alkalophilus* subtilisin (Kao)).

In some embodiments, the detergent compositions described herein further comprise a suitable amylase. In one embodiment, the composition comprises from about 0.00001% to about 10%, about 0.0001% to about 10%, about 0.001% to about 5%, about 0.001% to about 2%, or about 0.005% to about 0.5% amylase by weight of the composition. Any amylase (e.g., alpha and/or beta) suitable for use in alkaline solutions may be useful to include in such composition. An exemplary amylase can be a chemically or genetically modified mutant. Exemplary amylases include, but are not limited amylases described in GB1296839, WO91 00353, WO9402597, WO94183314, WO9510603, WO9526397, WO9535382, WO9605295, WO9623873, WO9623874, WO9630481, WO9710342, WO9741213, WO9743424, WO98 13481, WO9826078, WO9902702, WO9909183, WO9919467, WO9923211, WO9929876, WO9942567, WO9943793, WO9943794, WO9946399, WO0029560, WO0060058, WO00 60059, WO0060060, WO0114532, WO0134784, WO0164852, WO0166712, WO0188107, WO0196537, WO02092797, WO0210355, WO0231124, WO2004055178, WO2004113551, WO2005001064, WO2005003311, WO2005018336, WO 2005019443, WO2005066338, WO 2006002643, WO2006012899, WO2006012902, WO2006 031554, WO2006063594, WO2006 066594, WO2006066596, WO2006136161, WO2008 000825, WO2008088493, WO2008 092919, WO2008101894, WO2008112459, WO2009 061380, WO2009061381, WO2009 100102, WO2009140504, WO2009149419, WO2010 059413, WO2010088447, WO2010 091221, WO2010104675, WO2010 115021, WO10115028, WO2010117511, WO2011076123, WO2011076897, WO2011080352, WO2011080353, WO2011080354, WO2011082425, WO 2011082429, WO2011087836, WO2011098531, WO2013063460, WO2013184577, WO2014 099523, WO2014164777, and WO2015077126. Exemplary commercial amylases include, but are not limited to AMPLIFY®, AMPLIFY PRIME®, BAN™ DURAMYL®, TERMAMYL®, TERMAMYL® ULTRA, FUNGAMYL®, STAINZYME®, STAINZYME PLUS®, STAINZYME ULTRA®, and STAINZYME EVITY® (Novozymes); EFFECTENZ™ S 1000, POWERASE™, PREFERENZ™ S 100, PREFERENZ™ S 110, EXCELLENZ™ S 2000, RAPIDASE® and MAXAMYL® P (DuPont).

In some embodiments, the detergent compositions described herein further comprise a suitable pectin degrading enzyme. As used herein, "pectin degrading enzyme(s)" encompass arabinanase (EC 3.2.1.99), galactanases (EC 3.2.1.89), polygalacturonase (EC 3.2.1.15) exo-polygalacturonase (EC 3.2.1.67), exo-poly-alpha-galacturonidase (EC 3.2.1.82), pectin lyase (EC 4.2.2.10), pectin esterase (EC 3.2.1.11), pectate lyase (EC 4.2.2.2), exo-polygalacturonate lyase (EC 4.2.2.9) and hemicellulases such as endo-1,3-β-xylosidase (EC 3.2.1.32), xylan-1,4-β-xylosidase (EC 3.2.1.37) and α-L-arabinofuranosidase (EC 3.2.1.55). Pectin degrading enzymes are natural mixtures of the above mentioned enzymatic activities. Pectin enzymes therefore include the pectin methylesterases which hydrolyse the pectin methyl ester linkages, polygalacturonases which cleave the glycosidic bonds between galacturonic acid molecules, and the pectin transeliminases or lyases which act on the pectic acids to bring about non-hydrolytic cleavage of α-1,4 glycosidic linkages to form unsaturated derivatives of galacturonic acid.

Suitable pectin degrading enzymes include those of plant, fungal, or microbial origin. In some embodiments, chemically or genetically modified mutants are included. In some embodiments, the pectin degrading enzymes are alkaline pectin degrading enzymes, i.e., enzymes having an enzymatic activity of at least 10%, at least 25%, or at least 40% of their maximum activity at a pH of from about 7.0 to about 12. In certain other embodiments, the pectin degrading enzymes are enzymes having their maximum activity at a pH of from about 7.0 to about 12. Alkaline pectin degrading enzymes are produced by alkalophilic microorganisms e.g., bacterial, fungal, and yeast microorganisms such as *Bacillus* species. In some embodiments, the microorganisms are *B. firmus, B. circulans*, and *B. subtilis* as described in JP 56131376 and JP 56068393. Alkaline pectin decomposing enzymes may include but are not limited to galacturn-1,4-α-galacturonase (EC 3.2.1.67), poly-galacturonase activities (EC 3.2.1.15, pectin esterase (EC 3.1.1.11), pectate lyase (EC 4.2.2.2) and their iso enzymes. Alkaline pectin decomposing enzymes can be produced by the *Erwinia* species. In some embodiments, the alkaline pectin decomposing enzymes are produced by *E. chrysanthemi, E. carotovora, E. amylovora, E. herbicola*, and *E. dissolvens* as described in JP 59066588, JP 63042988, and in *World J. Microbiol. Microbiotechnol.* (8, 2, 115-120) 1992. In certain other embodiments, the alkaline pectin enzymes are produced by *Bacillus* species as disclosed in JP 73006557 and *Agr. Biol. Chem.* (1972), 36 (2) 285-93. In some embodiments, the detergent compositions described herein further comprise about 0.00001% to about 10%, about 0.0001% to about 10%, about 0.001% to about 5%, about 0.001% to about 2%, or about 0.005% to about 0.5% of pectin degrading enzyme by weight of the composition.

In some embodiments, the detergent compositions described herein further comprise a suitable mannanase enzyme. In one embodiment, the composition comprises from about 0.00001% to about 10%, about 0.0001% to about 10%, about 0.001% to about 5%, about 0.001% to about 2%, or about 0.005% to about 0.5% mannanase by weight composition. An exemplary mannanase can be a chemically or genetically modified mutant. Exemplary mannanases include, but are not limited to, those of bacterial or fungal origin, such as, for example, as is described in WO 2016/007929; U.S. Pat. Nos. 6,566,114; 6,602,842; and 6,440,991; and International Patent Appl Nos: PCT/US2016/060850 and PCT/US2016/060844 filed Nov. 7, 2016. Exemplary commercial mannanases include, but are not limited to MANNAWAY® (Novozymes) and EFFECTENZ™ M 1000, PREFERENZ® M 100, MANNASTAR®, and PURABRITE™ (DuPont).

In some further embodiments, the detergent compositions described herein further comprise a suitable second cellulase. Suitable second cellulases include, but are not limited to those of bacterial or fungal origin. Chemically or genetically modified mutants are included in some embodiments. Suitable second cellulases include, but are not limited to *H. insolens* cellulases (See, e.g., U.S. Pat. No. 4,435,307). Especially suitable cellulases are the cellulases having color care benefits (See, e.g., EP0495257). Commercially available second cellulases include, but are not limited to ENDOLASE®, CELLUCLEAN®, CELLUZYME®, CAREZYME®, RENOZYME®, and CAREZYME® PREMIUM (Novozymes A/S, Denmark), PURADEX®, (DuPont), and KAC-500(B)™ (Kao Corporation). In some embodiments, cellulases are incorporated as portions or fragments of mature wild-type or variant cellulases, wherein a portion of the N-terminus is deleted (See, e.g., U.S. Pat. No. 5,874,276). In some embodiments, the detergent compositions described herein further comprise from about 0.00001% to about 10%, about 0.0001% to about 10%, about 0.001% to about 5%, about 0.001% to about 2%, or about 0.005% to about 0.5% of cellulase by weight of the composition.

In still further embodiments, the detergent compositions described herein further comprise a suitable lipase. In some embodiments, the composition comprises from about 0.00001% to about 10%, about 0.0001% to about 10%, about 0.001% to about 5%, about 0.001% to about 2%, or about 0.005% to about 0.5% lipase by weight composition. An exemplary lipase can be a chemically or genetically modified mutant. Exemplary lipases include, but are not limited to, e.g., bacterial or fungal origin, such as, e.g., *H. lanuginosa* lipase (See, e.g., EP258068, and EP305216), *R. miehei* lipase (See, e.g., EP 238 023), *Candida* lipase, such as *C. antarctica* lipase (e.g., *C. antarctica* lipase A or B; see, e.g., EP214761), *Pseudomonas* lipases such as *P. alcaligenes* lipase and *P. pseudoalcaligenes* lipase (See, e.g., EP218272), *P. cepacia* lipase (See, e.g., EP331376), *P. stutzeri* lipase (See, e.g., GB 1,372,034), *P. fluorescens* lipase, *Bacillus* lipase (e.g., *B. subtilis* lipase [Dartois et al., (1993) *Biochem. Biophys. Acta* 1131:253-260]; *B. stearothermophilus* lipase [See, e.g., JP 64/744992]; and *B. pumilus* lipase [See, e.g., WO91/16422]). Exemplary cloned lipases include, but are not limited to *P. camembertii* lipase (See, Yamaguchi et al., [1991] *Gene* 103:61-67), *G. candidum* lipase (See, Schimada et al., [1989] *J. Biochem.* 106: 383-388), and various *Rhizopus* lipases such as *R. delemar* lipase (See, Hass et al., [1991] *Gene* 109:117-113), *R. niveus* lipase (Kugimiya et al., [1992] *Biosci. Biotech. Biochem.* 56:716-719), and *R. oryzae* lipase. Other types of suitable lipolytic enzymes include cutinases such as, for example, cutinase derived from *P. mendocina* (See, WO88/09367) and from *F. solani pisi* (See, WO90/09446). Exemplary commercial lipases include, but are not limited to M1 LIPASE™, LUMA FAST™, and LIPOMAX™ (DuPont); LIPEX®, LIPOCLEAN®, LIPOLASE® and LIPOLASE® ULTRA (Novozymes); and LIPASE P™ (Amano Pharmaceutical Co. Ltd).

In some embodiments, detergent compositions described herein further comprise peroxidases in combination with hydrogen peroxide or a source thereof (e.g., a percarbonate, perborate or persulfate). In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See, e.g., WO94/12621 and WO95/01426). Suitable peroxidases/oxidases include, but are not limited to those of plant, bacterial or fungal origin. Chemically or genetically modified mutants are included in some embodiments. In some embodiments, the detergent compositions further comprise from about 0.00001% to about 10%, about 0.0001% to about 10%, about 0.001% to about 5%, about 0.001% to about 2%, about 0.005% to about 0.5% of peroxidase and/or oxidase by weight of composition.

In some embodiments, detergent compositions described herein further comprise additional enzymes, including but not limited to perhydrolases (See, e.g., WO 05/056782).

In some embodiments, the detergent compositions described herein further comprise at least one chelating agent. Suitable chelating agents may include, but are not limited to copper, iron, and/or manganese chelating agents, and mixtures thereof. In embodiments in which at least one chelating agent is used, the detergent compositions comprise from about 0.1% to about 15% or even from about 3.0% to about 10% chelating agent by weight of composition.

In some still further embodiments, the detergent compositions described herein further comprise at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

In some embodiments, the detergent compositions described herein further comprise at least one anti-redeposition agent. In some embodiments, the anti-redeposition agent is a non-ionic surfactant, such as, for example, described in EP2100949.

In some embodiments, the detergent compositions described herein further comprise one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones, and polyvinylimidazoles, or mixtures thereof. In some embodiments, the detergent compositions described herein comprise from about 0.0001% to about 10%, from about 0.01% to about 5%, or even from about 0.1% to about 3% dye transfer inhibiting agent by weight of composition.

In some embodiments, the detergent compositions described herein further comprise one or more silicates. In some such embodiments, sodium silicates (e.g., sodium disilicate, sodium metasilicate, and crystalline phyllosilicates) find use. In some embodiments, the detergent compositions described herein comprise from about 1% to about 20% or from about 5% to about 15% silicate by weight of the composition.

In yet further embodiments, the detergent compositions described herein further comprise one or more dispersant. Suitable water-soluble organic materials include, but are not limited to the homo- or co-polymeric acids or their salts, in which the polycarboxylic acid comprises at least two carboxyl radicals separated from each other by not more than two carbon atoms.

In yet further embodiments, the detergent compositions described herein further comprise one or more bleach activator and/or bleach catalyst. Bleach activators are typically organic peracid precursors that enhance the bleaching action in the course of cleaning at temperatures of 60° C. and below. Bleach activators suitable for use herein include compounds which, under perhydrolysis conditions, give aliphatic peroxycarboxylic acids having preferably from about 1 to about 10 carbon atoms, in particular from about 2 to about 4 carbon atoms, and/or optionally substituted perbenzoic acid. Suitable bleach activators include, for example, those described in EP2100949. Bleach catalysts typically include, for example, manganese triazacyclononane and related complexes, and cobalt, copper, manganese, and iron complexes, as well as those described in U.S. Pat. Nos. 4,246,612; 5,227,084; 4,810,410; and WO99/06521 and EP2100949.

In some embodiments, fabric is exposed to a cellulase variant, or active fragment thereof, described herein prior to being worn such that removal of soil subsequently adhered to the fabric is improved in the first and/or subsequent two, three, or more wash cycles over soiled fabric that is not exposed to the cellulase variant, or active fragment thereof, described herein prior to being worn. In other embodiments, fabric is exposed to the cellulase variant, or active fragment thereof, described herein after being worn such that the removal of soil subsequently adhered to the fabric is improved in the first and/or subsequent two, three, or more wash cycles over soiled fabric that is not subsequently exposed to the cellulase variant, or active fragment thereof, described herein. In still further embodiments, cellulase variant, or active fragment thereof, described herein finds use in a detergent composition, a textile finishing process, or a paper and pulp process.

Yet another embodiment is directed to enhancing the feel and/or appearance and/or providing color enhancement and/or a stone washed appearance to a cellulose containing textile material (such as, for example, cotton, flax, ramie, jute, viscose, modified viscose fibers, lyocell and cupro) comprising treating the material with an effective amount of a cellulase variant, or active fragment thereof, described herein or a composition comprising an effective amount of a cellulase variant, or active fragment thereof, described herein. A still further embodiment is directed to a method for reducing color redeposition during the stone washing of colored fabrics comprising contacting the fabric with an effective amount of a cellulase variant, or active fragment thereof, described herein or a composition comprising an effective amount of a cellulase variant, or active fragment thereof, described herein under conditions sufficient to impart a stone-washed appearance to the fabric. In still another embodiment, a cellulose containing textile material treated with an effective amount of a cellulase variant, or active fragment thereof, described herein or a composition comprising an effective amount of a cellulase variant, or active fragment thereof, described herein retains substantially all of the material's tensile strength as compared to an untreated cellulose containing textile material. In yet still another embodiment, a cellulose containing textile material treated with an effective amount of a cellulase variant, or active fragment thereof, described herein or a composition comprising an effective amount of a cellulase variant, or active fragment thereof, described herein retains 50%, 60%, 70%, 80%, 90%, 91%, 92%, 93%, 94%, 95%, 96%, 97%, 98%, 99%, and 100% of the material's tensile strength as compared to an untreated cellulose containing textile material.

Other aspects and embodiments of the present compositions and methods will be apparent from the foregoing description and following examples. Various alternative embodiments beyond those described herein can be employed in practicing the invention without departing from the spirit and scope of the invention. Accordingly, the claims, and not the specific embodiments described herein, define the scope of the invention and as such methods and structures within the scope of the claims and their equivalents are covered thereby.

EXAMPLES

The following examples are provided to demonstrate and/or illustrate certain aspects of the present disclosure and should not be construed to limit the scope of the disclosure or any subsequently claimed invention.

Example 1

Assays

The following assays are standard assays used in the examples described below. Occasionally specific protocols called for deviations from these standard assays. In those cases, deviations from these standard assay protocols below are identified in the examples.
Performance Index
The performance index (PI) of an enzyme compares the performance of the variant (measured value) with a parent or reference polypeptide (theoretical or measured value) at the same protein concentration. Theoretical concentrations for the parent or reference polypeptide can be calculated using the parameters extracted from a Langmuir fit of a standard curve of the parent enzyme. A PI that is greater than 1 (PI>1) indicates improved performance by a variant as compared to the parent or reference polypeptide, while a PI of 1 (PI=1) identifies a variant that performs the same as the parent or reference polypeptide, and a PI that is less than 1 (PI<1) identifies a variant that does not perform as well as the parent or reference polypeptide. For example, the STCE1 wild-type (STCE1-WT) mature protein set forth as SEQ ID NO:5 is the parent of the STCE1-A142P variant set forth as SEQ ID NO:8.
Protein Determination Assay (A280)
Absorbance at 280 nm was measured for purified enzyme samples in microtiter plates (Costar 3635, Sigma/Aldrich, USA) using a SpectraMax plate reader (Molecular Devices, USA). The responses of the STCE1-WT standards (standard protein ranges 50 ppm to 1000 ppm) were used to plot a standard curve. Absorbance values of variant samples were then interpolated from those graphs.

Protein Determination Assay (HPLC)
For high resolution concentration determinations, high performance liquid chromatography (HPLC) method was performed on protein samples. An Agilent 1290 U (HPLC) equipped with a Zorbax C-3 column was used for protein quantitation. Samples were eluted from the column using a gradient of 0.1% trifluoroacetic acid (TFA) in water and 0.07% TFA in acetonitrile. Absorbance was measured at 220 nm, and peaks were integrated using ChemStation software (Agilent Technologies, USA). The protein concentrations of the samples were calculated based on a standard curve of the purified STCE1-WT mature protein (SEQ ID NO:5).
Cellulase Activity Assay Using PAHBAH Reagent
The activity of cellulase enzymes was tested on carboxymethyl cellulose (CMC) substrate using the 4-hydroxybenzoic acid hydrazide (PAHBAH) reagent. The enzymatic activity was based on the hydrolysis of CMC substrate into reducing sugars followed by the detection of the new reducing ends by the PAHBAH reagent. The reagent PAHBAH stock solution (Sigma-Aldrich, USA) was prepared as 5% solution in 0.5 N hydrochloric acid (HCL). The PAHBAH reagent was further diluted in 0.5 M sodium hydroxide (NaOH) in 1:4 ratios to make up a final 1% solution. 1% CMC substrate was made in one of three different buffer solutions: 50 mM HEPES buffer solution, pH 8.2; 50 mM sodium acetate (NaOAc) buffer solution, pH 5; and 50 mM CAPS buffer solution, pH 10.8. The enzyme samples, adjusted to either pH 5 (4 µL), pH 8.2 (6 µL) or pH 10 (8 µL), were added to a microtiter plates (MTP) containing 40 µl of the 1% CMC solution and incubated at 40° C. in iEMS™ Microplate Incubator/Shaker HT (ThermoFisher Scientific Inc, USA) for 15 min; then 8 µl of enzyme-substrate mix was transferred to a new MTP containing 20 µl of 1% PAHBAH per well and incubated at 95° C. in a thermocycler machine (Eppendorf™ Mastercycler™ pro PCR system, Thermo Fisher Scientific, USA) for 5 min. Finally, 20 µl of each reaction solution was transferred to a fresh MTP and the absorbance was measured at 410 nm using a SpectraMax plate reader.
Stability Measurement Using Cellulase Activity Assay
Cellulase enzyme samples were tested for stability in the presence and absence of protease under various stress conditions set forth on Table 1 by measuring residual activity. The stressed and unstressed cellulase activities were measured using the cellulase activity assay described herein. The protease used in the assays was commercially available BPN'-Y217L subtilisin, which is forth below as SEQ ID NO:7.
The stability assay conditions that were used are described in Table 1. Prior to using commercially available detergent in the stability assays, the enzymes contained in the detergent was inactivated by heating the detergent samples in a water bath set to 100° C. for 2 hrs.

TABLE 1

| Conditions for cellulase stability assays using CMC substrate | | |
| --- | --- | --- |
| Measurement | Condition | Stress temperature (° C.) and incubation time |
| Thermostability of STCE1-WT and variants thereof | 50 mM HEPES buffer pH 8.2 | 80° C. for 10 min |
| Stability of STCE1-WT and variants thereof in the presence of Protease | 1500 ppm BPN'-Y217L protease in 50 mM HEPES buffer pH 8.2 | 65° C. for 37 min |
| Stability of *H. insolens*, *N. crassa*, *T. terrestris* and variants thereof | 1500 ppm BPN'-Y217L protease in 50 mM HEPES buffer pH 8.2 | 65° C. for 15 min |

TABLE 1-continued

Conditions for cellulase stability assays using CMC substrate

| Measurement | Condition | Stress temperature (° C.) and incubation time |
|---|---|---|
| Stability of STCE1-WT and variants thereof in the presence of detergent and protease | 1% OMO Klein & Krachtig* plus 1000 ppm BPN'-Y217L protease in 50 mM HEPES buffer pH 8.2 | 37° C. for 24 hr |
| Stability of H. insolens and variants thereof in the presence of detergent and protease | 1% OMO Klein & Krachtig* plus 1000 ppm BPN'-Y217L protease in 50 mM HEPES buffer pH 8.2 | 37° C. for 36 hr |
| Stability of N. crassa and variants thereof in the presence of detergent and protease | 1% OMO Klein & Krachtig* plus 1000 ppm BPN'-Y217L protease in 50 mM HEPES buffer pH 8.2 | 37° C. for 2 hr |
| Stability of T. terrestris and variants thereof in the presence of detergent and protease | 1% OMO Klein & Krachtig* plus 1000 ppm BPN'-Y217L protease in 50 mM HEPES buffer pH 8.2 | 37° C. for 4 hr |

*Heavy-duty liquid laundry detergent commercially sold by Unilever

For the unstressed test conditions, the enzyme samples were not incubated prior to assaying for activity.

For the stressed test conditions, the enzyme samples were prepared in PCR/MTP plates, sealed, and incubated at the elevated temperatures and under the conditions described in Table 1 using: i) an Eppendorf™ 384 MasterCycler™ Pro Thermocycler to measure thermostability, and stability in the presence of protease (ii) an iEMS incubator to measure stability in the presence of detergent and protease. After the various incubation periods, the samples were assayed for cellulase activity.

Stressed and unstressed activities were measured by the cellulase activity assay described above. The residual activity of the enzyme sample tested in each assay was calculated as the mean of three replicates with blank subtracted. The relative residual activity of each enzyme sample was calculated as the ratio between residual activity and unstressed activity. The relative residual activity percentage was calculated by multiplying the relative residual activity number by 100. The PI of each STCE1-WT variant was calculated as the ratio between relative residual activity for the variant and relative residual activity for the STCE1-WT cellulase.

Example 2

Expression of Various G1145 Cellulases and Variants Thereof

The gene encoding the STCE1-WT cellulase (previously described as a family 45 glycoside hydrolase in the publication, Koga, J., Y. Baba, A. Shimonaka, T. Nishimura, S. Hanamura and T. Kono (2008), "Purification and characterization of a new family 45 endoglucanase, STCE1, from Staphylotrichum coccosporum and its overproduction in Humicola insolens." Appl. Environ. Microbiol. 74(13): 4210-4217) was selected as a template for generating the parent cellulase and variants thereof. The genes encoding the Humicola insolens-WT cellulase (accession number CAA01574.1), and the Neurospora crassa-WT cellulase (accession number XP_957107.1) were also selected as templates for generating the parent cellulases and variants thereof. In addition, a one amino acid variant of the Thielavia terrestris-WT cellulase (accession number XP_003651003.1) was also selected as template for generating the parent cellulase and variants thereof. The modified Thielavia terrestris cellulase has a histidine (H) at position 120 of the mature cellulase protein sequence and is describe here as Thielavia terrestris 120H.

The stce1, T. terrestris and N. crassa genes, encoding the wildtype (WT) form of the proteins (also referred to herein as the parent), contained an intron within the coding DNA that was removed using molecular biology techniques known in the art. The resulting genes were sub-cloned into the expression vector pTTT-pyr2 utilizing standard reagents. The pTTTpyr2 vector is similar to the pTTTpyrG vector described previously, for example, in WO2011153449A1 except that the A. nidulans pyrG gene is replaced with the H. jecorina pyr2 gene. The pTTT-pyr2 expression vector contained the T. reesei cbhI-derived promoter (cbhI) and cbhI terminator regions allowing for a strong inducible expression of the gene of interest, the A. nidulans amdS and pyr2 selective markers conferring growth of transformants on acetamide as a sole nitrogen source, and the T. reesei telomere regions allowing for non-chromosomal plasmid maintenance in a fungal cell.

A map of the pTTT-pyr2 based vector containing the stce1-WT cellulase gene (SEQ ID NO:3), pTTT-pyr2-stce1 is shown in FIG. 1. Similarly built vectors (pTTT-pyr2-H. insolens, pTTT-pyr2-N. crassa, and pTTT-pyr2-T. terrestris) were prepared for the expression of the H. insolens, N. crassa and T. terrestris cellulases.

Using molecular biology techniques known in the art, stce1, H. insolens, N. crassa and T. terrestris single amino acid substitutions were designed by introducing the codon sequence for the desired amino acid change in the base plasmids pTTT-pyr2-stce1, pTTT-pyr2-H. insolens, pTTT-pyr2-N. crassa, and pTTT-pyr2-T. terrestris. Protoplasts of a suitable Trichoderma reesei host strains were transformed by the PEG based protocol described in U.S. Pat. No. 8,679,792. After growth of transformants, spores from each well were pooled and re-patched using minimal medium containing acetamide as a sole nitrogen source. Upon sporulation, spores were harvested and used for inoculation in a Aachen medium. Cultures were incubated for 6 days at 28° C., 80% humidity and 50 mm shaking throw in a Multitron shaker incubator (Infors, Switzerland). The culture broth was filtered to collect the clarified supernatant, which was stored at −20° C.

The nucleotide sequence of the stce1-WT gene in the pTTT-pyr2-STCE1 vector is set forth as SEQ ID NO:3 (951 base pairs). The amino acid sequence of the translation product of the stce1-WT gene is set forth as SEQ ID NO:4 (316 amino acids), wherein the N-terminal 21 amino acids constitute the signal peptide. The amino acid sequence of the mature form of STCE1-WT protein is set forth as SEQ ID NO:5 (295 amino acids), wherein the C-terminal 37 amino acids constitute the carbohydrate binding module (CBM).

The STCE1-WT and variant proteins were purified by ammonium sulfate precipitation, adding 3M $(NH_4)_2SO_4$ to clarified culture broth in 1:1 dilution and using a Relisorb OC 400 resin (Resindon, Italy) in 20 mM $KH_2PO_4$, pH 6.0. The resin was washed with 20 mM $KH_2PO_4$ pH 6.0+0.5M $(NH_4)_2SO_4$ buffer and the STCE1 proteins were eluted in 20 mM $KH_2PO_4$ pH 6.0 buffer and refrigerated until assayed.

The nucleotide sequence of the *H. insolens*-WT gene in the pTTT-pyr2-*H. insolens* vector is set forth as SEQ ID NO:9. The amino acid sequence of the translation product of the *H. insolens*-WT gene is set forth as SEQ ID NO:10. The amino acid sequence of the mature *H. insolens*-WT cellulase is set forth as SEQ ID NO:11.

The nucleotide sequence of the *N. crassa*-WT gene in the pTTT-pyr2-*N. crassa* vector is set forth as SEQ ID NO:12. The amino acid sequence of the translation product of the *N. crassa*-WT gene is set forth as SEQ ID NO:13. The amino acid sequence of the mature *N. crassa*-WT cellulase is set forth as SEQ ID NO:14.

The nucleotide sequence of the *T. terrestris*-120H gene in the pTTT-pyr2-*T. terrestris* vector is set forth as SEQ ID NO:15. The amino acid sequence of the translation product of the *T. terrestris*-120H gene is set forth as SEQ ID NO:16. The amino acid sequence of the mature *T. terrestris*-120H cellulase is set forth as SEQ ID NO:17.

Example 3

Crystal Structure Determination and Unique Features of STCE1-WT Cellulase

Crystallization of STCE1-WT Protein

The mature STCE1-WT protein (SEQ ID NO:5) was found refractory to crystallization. Purified STCE1-WT protein was digested by papain enzyme, which clipped the protein backbone following the G214 position in the linker domain of the mature STCE1-WT protein (SEQ ID NO:5). The amino acid sequence of the clipped STCE1-WT protein, also referred to as truncated STCE1-WT, obtained by papain digestion is set forth as SEQ ID NO:6 (214 amino acids).

This truncated STCE1-WT protein was crystallized using the hanging drop method from a solution of protein stock at a concentration of 25.5 mg/mL in 50 mM MES pH 6.3. Aliquots of 2.5 mL of the protein stock and 2.5 mL of the crystallization solution (1.79M ammonium sulfate, 95 mM Tris pH 8.5 and 91 mM sodium iodide) were mixed on a plastic coverslip and inverted and sealed on a chamber containing the crystallization solution in a Linbro 6×4 culture plate. Crystals grew in the space group P43212 with unit cell dimensions; a=39.4 Å, b=39.4 Å, and c=228.65 Å. Data were collected on the native crystal to a resolution of 2.0 Å and the structure of STCE1-WT was determined by molecular replacement using a related protein, *Melanocarpus albomyces* endoglucanase (pdb ID 1OA7) as the phasing model. The crystal data collected for STCE1-WT is set forth in Table 2.

TABLE 2

Statistics of truncated STCE1-WT data

| Wavelength | 1.54 Å |
| Space group | P4$_3$2$_1$2 |
| Molecules in asymmetric unit | 1 |
| Unit cell dimensions | 39.4, 39.4, 228.65 Å |
| Resolution | 2.0 |
| Unique reflections | 13244 |
| Multiplicity | 6.4 |
| Completeness | 94% |

TABLE 2-continued

Statistics of truncated STCE1-WT data

| $R_{merge}$ | 0.06 |
| $I/\sigma_I$ | 21 |

The model was fitted in the resulting electron density using the program COOT as described in Emsley et al (Emsley, P., B. Lohkamp, W. G. Scott and K. Cowtan (2010). "Features and development of Coot." *Acta Crystallogr D Biol Crystallogr* 66(Pt 4): 486-501). After fitting and refitting adjustments, the coordinates were refined using the REFMAC program with standard defaults in the CCP4 software suite. The statistics of the structural model are presented in Table 3.

TABLE 3

Statistics of the refined model

| R work | 0.196 |
| R free | 0.262 |
| No. protein residues | 214 |
| No. atoms | 1674 |
| rmsd Bond lengths | 0.015 Å |
| rmsd bond angles | 1.79° |

Structure Determination of Truncated STCE1-WT

Figure 2:
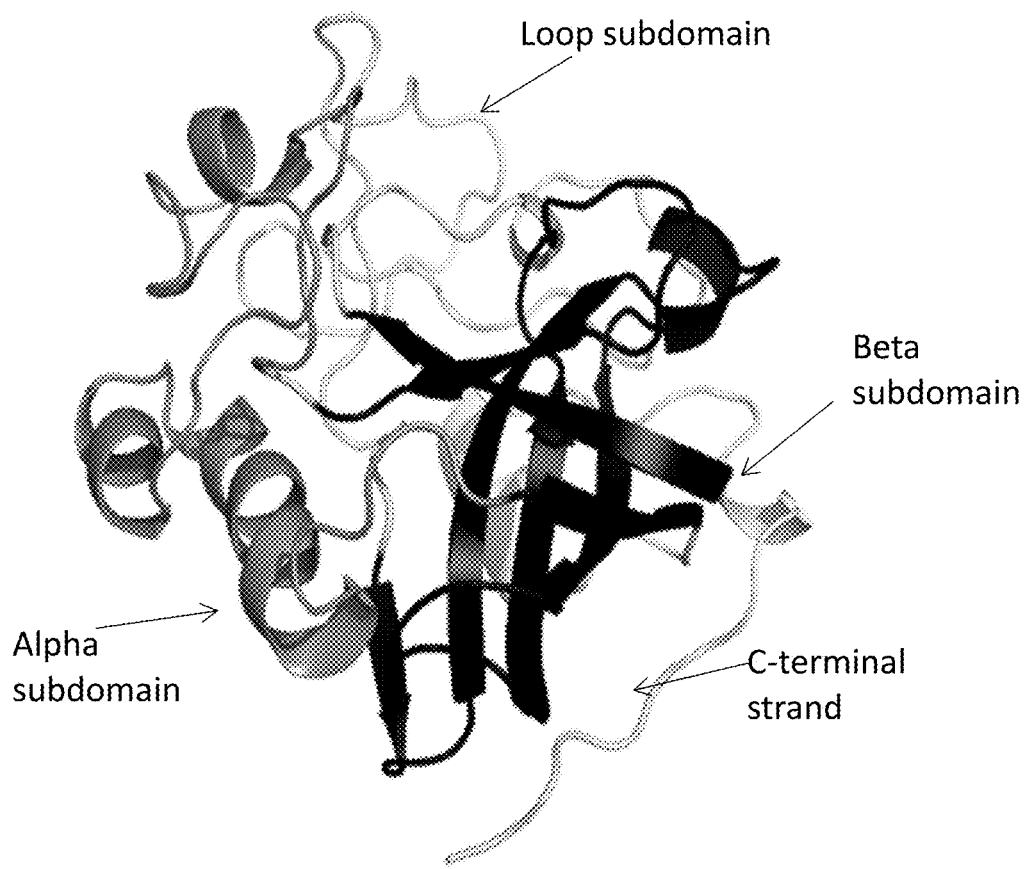
FIG. 2 provides a schematic of the main chain folding of the truncated STCE1-WT cellulase, showing the beta subdomain (in black), the loop subdomain (light lines), the alpha subdomain (medium dark), and the C-terminal strand.

FIG. 2 depicts the structure of the catalytic core of truncated STCE1-WT cellulase. The catalytic core can be visualized as consisting of three subdomains: a twisted beta barrel domain formed by strands belonging to residues 1-9, 61-121, and 180-185; an alpha helical domain formed by residues 125-172; and an extended loop domain formed by residues 10-60. The C-terminal segment, which would extend into the linker and CBM in the full length molecule, extends over the beta subdomain and will be considered part of it for the remainder of this discussion.

Figure 3:
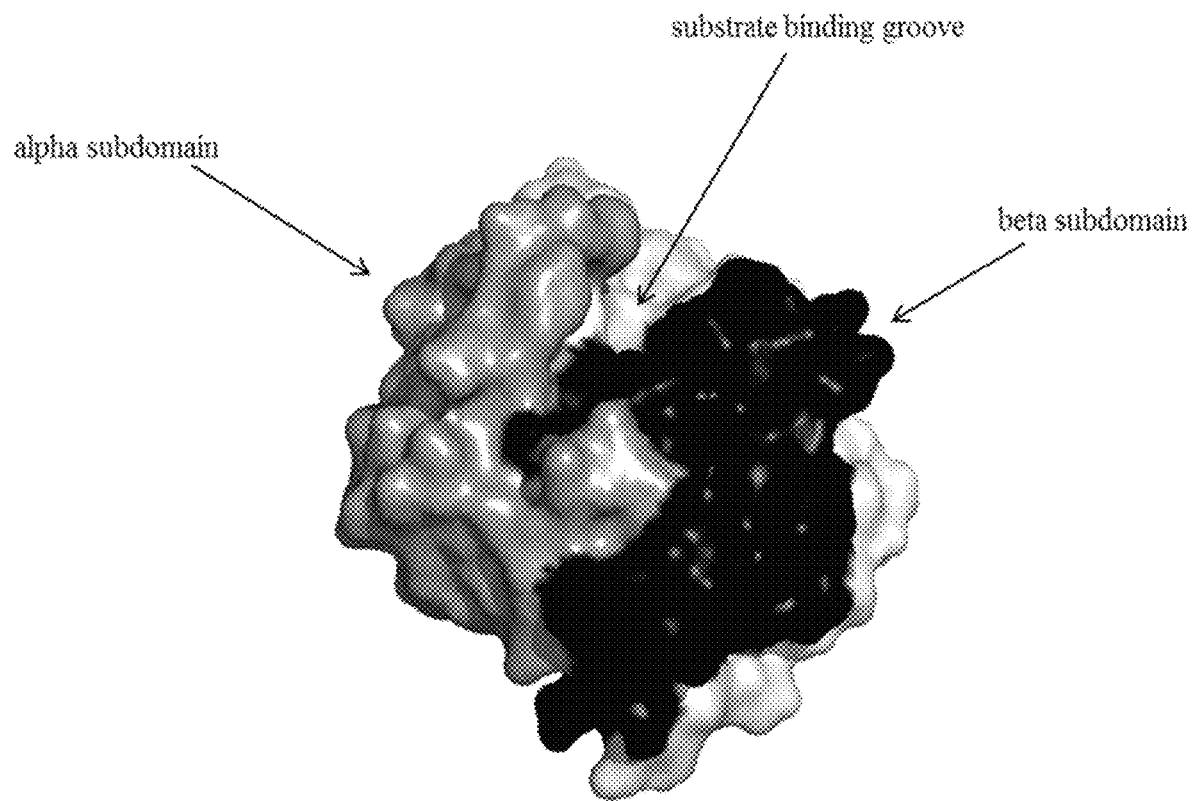
FIG. 3 provides a surface rendering of truncated STCE1-WT cellulase displaying a view of the substrate binding cleft found to occur in the groove formed between the beta (dark color) and alpha (medium color) subdomains.

FIG. 3 shows a surface rendering, depicting the substrate binding cleft formed between the beta barrel and alpha helical subdomains. The substrate binding cleft is found to occur in the groove formed between the beta and alpha subdomains. The crystal structure includes part of the linker domain that would connect the catalytic core with the CBM. This partial linker extends over the central beta strand formed by residues 100-107 which itself is part of the beta barrel subdomain.

Figure 4:
FIG. 4 provides a structural comparison of three GH45 cellulase family enzyme structures where the schematic of truncated STCE1-WT is shown in black, the schematic for *Humicola insolens* endoglucanase is shown in medium gray, and the schematic for *Melanocarpus albomyces* endoglucanase is shown in light gray.

The structure of the catalytic core of truncated STCE1-WT cellulase is homologous to the catalytic core of two other known GH45 family enzymes, the *Melanocarpus albomyces* endoglucanase (pdb ID 1OA7) and the Endoglucanase V from *Humicola insolens* (pdb ID 3ENG). As shown in FIG. 4, the overall protein folding is highly similar among the three structures, including the distribution of the six disulfide bridges. It can be seen that the overall folding of these enzymes is highly conserved, even though the catalytic core of STCE1-WT shares only 75.2% and 80.8% sequence identity, respectively, with the catalytic cores of the other two GH45 cellulases.

Example 4

Evaluation of Protease Labile Sites in STCE1-WT Cellulase

In order to identify protease labile sites, STCE1-WT cellulase (SEQ ID NO:5) was incubated with commercially available BPN'-Y217L protease (10:1 ratio) at 37° C. The amino acid sequence of the commercially available BPN'-Y217L is set forth as SEQ ID NO:7.

Protease treated samples of the cellulase were withdrawn at differing time points and assayed for cellulase activity. The incubation reactions were stopped by using 1N HCl, and the sample was filtered to collect soluble fraction. The samples were further digested with trypsin to obtain appropriate sized fragments for mass spectrometric analysis. Tryptic digests were subjected to LC MS/MS using the Proxeon Easy-nano system (Thermo Scientific, FL, USA). Trypsin is known to cleave polypeptide backbones C-terminal to positively charged amino acid residues, lysine (K) or arginine (R). In addition to the expected cleavage pattern due to trypsin action on STCE1-WT (SEQ ID NO:5), the BPN'-Y217L cleavage pattern identified cleavage sites at A142 and Q216.

In view of the above, single amino acid variants were generated for the A142 and Q216 sites and these variants were assayed under various conditions to measure improvements in properties valuable for laundry cellulases. In particular, the stability of these variant cellulase and STCE1-WT cellulase were measured under the test conditions described in Example 1 including: thermostability, stability in the presence of a protease, and stability in the presence of protease and detergent. The relative activity and stability performance results are shown in Table 4, reported as performance index (PI) of variants versus STCE1-WT (SEQ ID NO:5). These results indicate that replacing alanine at position 142 with an amino acid selected from D, E, P and Q yielded variants with improved stability. Likewise, replacing glutamine at position 216 with an amino acid selected from D, E, G, P, S, T and V also yielded variants with improved stability when compared to STCE1-WT (SEQ ID NO:5).

TABLE 4

Relative Performance Compared to STCE1-WT, Reported as PI

| | | | Stability Performance | | |
|---|---|---|---|---|---|
| Position | Variant | CMC Activity, pH 8.2 | Detergent (OMO) and Protease | Protease | Thermal |
| 142 | A142D | 0.9 | 2.7 | 1.7 | 1.0 |
| 142 | A142E | 1.0 | 2.9 | 1.9 | 1.0 |
| 142 | A142P | 0.9 | 3.0 | 2.2 | 1.0 |
| 142 | A142Q | 1.1 | 0.8 | 1.1 | 0.9 |
| 216 | Q216D | 1.0 | 0.9 | 1.0 | 1.2 |
| 216 | Q216E | 1.0 | 0.8 | 1.2 | 0.5 |
| 216 | Q216G | 1.0 | 0.8 | 1.2 | 1.0 |
| 216 | Q216P | 1.0 | 1.2 | 1.0 | 1.0 |
| 216 | Q216S | 1.1 | 1.0 | 0.9 | 1.0 |
| 216 | Q216T | 1.2 | 1.1 | 1.1 | 1.0 |
| 216 | Q216V | 1.1 | 1.5 | 1.1 | 1.1 |

Example 5

Long Term Stability Analysis of the STCE1-A142P Variant Cellulase

The STCE1-A142P variant (SEQ ID NO:8) was tested for long term stability in various liquid detergents containing a protease relative to two other cellulases, the STCE1-WT parent and a commercial Benchmark cellulase (Carezyme® 4500L) (Novozymes AS, Denmark). The amino acid sequence of the mature form of the STCE1-A142P variant is set forth as SEQ ID NO:8 (295 amino acids).

The in-detergent stability of the STCE1-A142P variant was tested in commercial Heavy Duty Liquid (HDL) detergents: OMO Color Klein & Krachtig (Unilever), Persil Color-Gel (Henkel) and Ariel Actilift™ Excel Gel (Procter and Gamble). All commercial detergents were purchased in the Netherlands in 2014. For the detergent resistance stability tests in Persil and Ariel, the enzymes present in the detergents were heat inactivated as described in Example 1. The STCE1-A142P variant, STCE1-WT parent, or Benchmark was added to cooled detergent to provide a final concentration of 200 ppm in detergent. To determine the level of cellulase resistance to proteolytic inactivation, commercially available BPN'-Y217L subtilisin protease was added to the cooled cellulase containing detergent to final concentration of 1000 ppm in detergent.

Another subset of stability tests were carried out in commercial OMO Color Klein & Krachtig detergent wherein the detergent was not heat inactivated and thus contained the protease already present in the commercially available detergent. The STCE1-WT parent, STCE1-A142P variant, or commercial Benchmark cellulase was added to this detergent to a final concentration of 200 ppm in detergent. All detergent samples were incubated at 30° C. in an incubator. To determine remaining cellulase activity, aliquots were removed from each detergent reaction sample at different time intervals and tested using the AZCL-HE-Cellulose substrate (Cellazyme C tablet, Megazyme International) Briefly, 100 µl of sample was added to 1.9 ml of 50 mM Acetate/Bis-Tris/HEPES/CHES, pH 8.0 buffer and mixed well. 500 µl of sample in substrate was pre-incubated at 40° C. for 2 min followed by addition of a Cellazyme C tablet and incubated for another 10 min at 40° C. Following this step, the reaction was stopped by adding 10 ml of 2% Tris (pH 12.0) solution. Resultant solution was then filtered through a Whatman number #1 filter paper and absorbance measured in SpectraMax plate reader at 590 nm wavelength. The resultant data was calculated as percent remaining cellulase activity, with day zero activity considered as 100%. The results are shown in FIGS. 5A-5C.

Figure 5A:
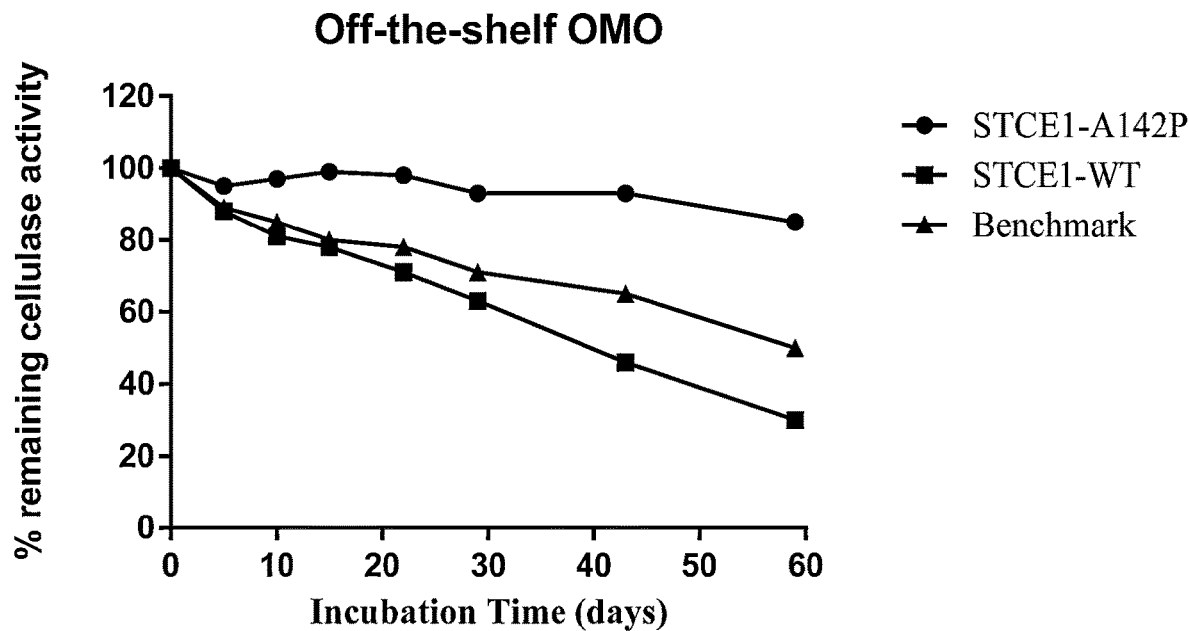
FIGS. 5A-5C depict the long term stability of STCE1-A142P, STCE1-WT, and Benchmark cellulases in detergents containing a protease.
Figure 5B:
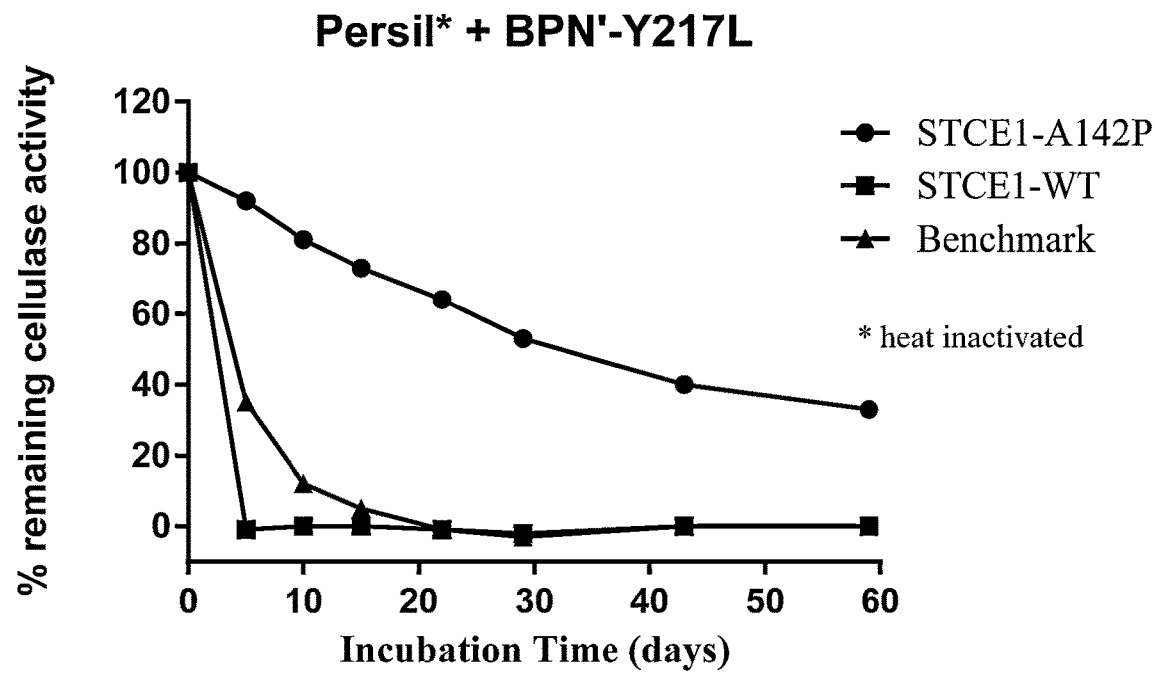
Figure 5C:
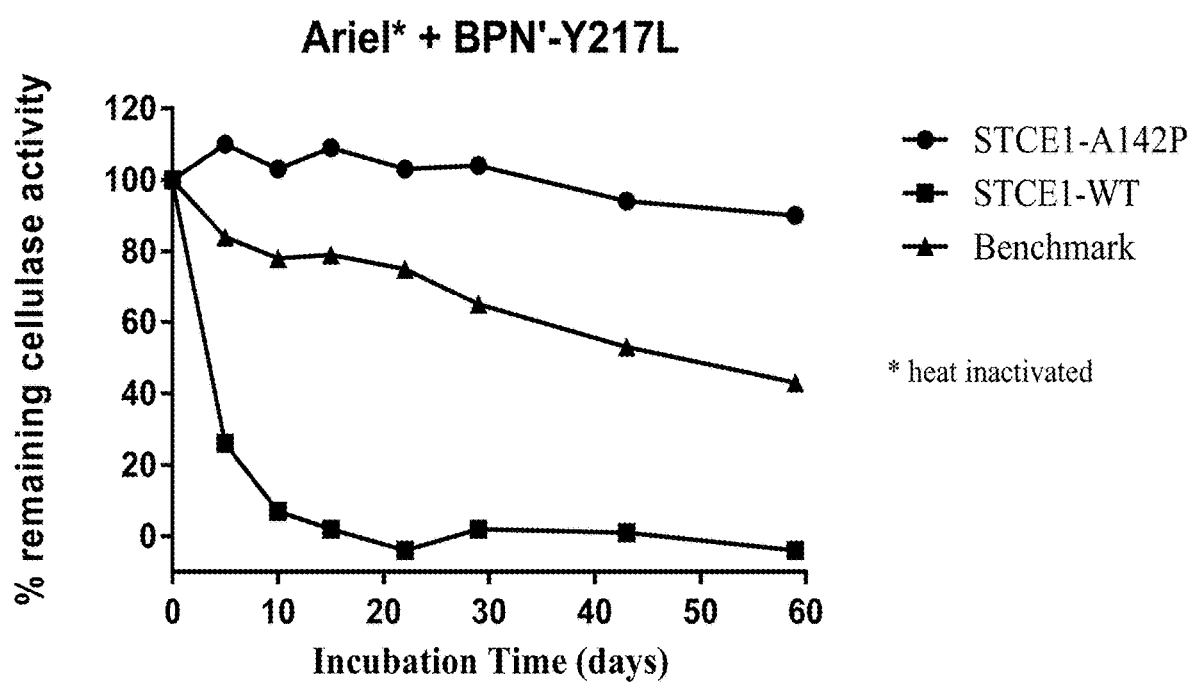

As FIGS. 5A-5C show, the STCE1-A142P variant has remarkable stability in the detergents tested as compared to the STCE1-WT and Benchmark cellulases.

Example 6

Performance of Cellulases in a Liquid Detergent

Performance tests were carried out in commercial Kirkland Signature™ liquid detergent (Sun Products Corp., USA). Detergent was heat inactivated at 80° C. for 3 hrs, followed by addition of 1% boric acid, 2% glycerol and 0.02% $CaCl_2$) after cooling. To this detergent stabilizer mix, either STCE1-WT, Benchmark (Carezyme® 4500L), or STCE1-A142P variant cellulase was added along with commercially available proteases: BPN'-Y217L or Properase® (DuPont, USA) protease. All samples were incubated at 37° C. in an incubator up to 6 weeks. Aliquots of the samples were taken every couple of weeks and were tested for wash performance on cellulase-sensitive stains. 2 g/L of liquid detergent was added per wash cycle in a Tergotometer (India Tergotometer, India). To a total of 1.5 L wash liquor, cellulase and either commercially available BPN'-Y217L or Properase® protease were added such that their final concentrations in wash liquor were 3 ppm each. To mimic depilling performance six swatches of pre-pilled homogenous size (127 mm×127 mm) brushed interlock fabric were added to the Tergotometer pot, filled with 1.49 L of deionized water and 7.5 ml of Ca$^{2+}$Mg$^{2+}$ (4:1) liquid in an overall 250 ppm water hardness. The wash cycle was carried out at a temperature of 30° C., for 90 min. After single wash cycle, the swatches were rinsed in the running water for 10 min and dry-spun in Front Load Washing Machine (Bosch). The swatches were cooled to room temperature before fuzz and pill measurement readings were taken as Panel Unit Scores (PUS).

PUS were measured using a Multiray device (Videometer A/S Denmark) with six readings taken per swatch with and the average of thirty-six readings being used as the PUS for each sample. These readings are based on a calibration model generated by treating pre-pilled swatches with varying units of cellulase enzyme to generate a standard curve with readings between 1 to 5 PUS measured, depending on the fuzz and pills present on the surface of the fabric.

The higher the PUS (3-5), the better the performance or longer stability of the cellulase enzyme in the presence of protease; whereas, low PUS (1-2) indicate little or no improvement in cellulase performance in the presence of protease. Results are shown in Table 5. As indicated from the performance results shown on Table 6, the Day 0 wash results shows that the STCE1-A142P variant has similar depilling performance when compared with STCE1-WT and Benchmark. The wash result of aged samples shows that the STCE1-A142P variant retains a markedly higher depilling performance than STCE1-WT and Benchmark in Kirkland Signature UltraClean HE Liquid laundry detergent (Kirkland HDL, purchased in Costco, USA) when stored at 37° C. in the presence of two commercially available proteases commonly used in detergent applications, BPN'-Y217L and Properase®.

TABLE 5

Measure of cellulase depilling activity in Kirkland HDL detergent

| Enzyme(s) | Incubation time (weeks) | | |
|---|---|---|---|
| | 0 | 2 | 6 |
| No Enzyme | 1.5 | 1.5 | 1.7 |
| STCE1-A142P variant cellulase | 4.5 | 4.6 | 4.4 |

TABLE 5-continued

Measure of cellulase depilling activity in Kirkland HDL detergent

| Enzyme(s) | Incubation time (weeks) | | |
|---|---|---|---|
| | 0 | 2 | 6 |
| STCE1-WT cellulase | 4.6 | 4.6 | 4.4 |
| Benchmark cellulase | 4.4 | 4.4 | 4.2 |
| STCE1-A142P cellulase + BPN'-Y217L protease | 4.6 | 3.5 | 3.1 |
| STCE1-WT cellulase + BPN'-Y217L protease | 4.3 | 2.0 | 1.5 |
| Benchmark cellulase + BPN'-Y217L protease | 4.4 | 2.5 | 1.6 |
| STCE1-A142P variant cellulase + Properase® protease | 4.5 | 3.8 | 3.7 |
| STCE1-WT cellulase + Properase® protease | 4.4 | 3.5 | 2.5 |
| Benchmark cellulase + Properase® protease | 4.4 | 3.0 | 2.2 |

Example 7

Comparison of STCE1-WT Cellulase to Related Molecules and Identification of Homologous Cellulases Related proteins were identified by a BLAST search (as described in Altschul, S. F., T. L. Madden, A. A. Schaffer, J. Zhang, Z. Zhang, W. Miller and D. J. Lipman (1997), "Gapped BLAST and PSI-BLAST: a new generation of protein database search programs." *Nucleic Acids Res* 25 (17): 3389-3402) against the NCBI non-redundant protein database using the mature STCE1-WT protein sequence (SEQ ID NO:5) and a subset of the results are shown in Table 6. A similar search was run against the Genome Quest Patent database with search parameters set to default values using the mature protein amino acid sequences for STCE1-WT cellulase (SEQ ID NO:5) as the query sequence, and a subset are shown in Table 7.

TABLE 6

NCBI Protein Sequence Search of STCE1 WT Protein Sequence

| Accession Number | % ID | Organism | Subject Length | Alignment Length |
|---|---|---|---|---|
| BAG69187 | 100.0 | *Staphylotrichum coccosporum* | 316 | 295 |
| KOP50759 | 79.6 | *Madurella mycetomatis* | 238 | 211 |
| CDF76466 | 79.4 | *Scytalidium indonesiacum* | 277 | 218 |
| CDF76460 | 78.9 | *Chaetomium senegalense* | 190 | 190 |
| XP_006694935 | 78.6 | *Chaetomium thermophilum* var. *thermophilum* DSM 1495 | 314 | 294 |
| AGY80101 | 78.6 | *Chaetomium thermophilum* | 293 | 294 |
| CAD56665 | 75.5 | *Melanocarpus albomyces* | 235 | 212 |
| CAA01574 | 73.6 | *Humicola insolens* | 305 | 298 |
| BAA74956 | 73.2 | *Humicola grisea* var. *thermoidea* | 305 | 295 |
| XP_003651003 | 71.7 | *Thielavia terrestris* NRRL 8126 | 299 | 293 |
| CDF76465 | 70.8 | *Remersonia thermophila* | 260 | 271 |
| XP_001903789 | 68.9 | *Podospora anserina* S mat+ | 302 | 293 |
| KFH43153 | 68.3 | *Acremonium chrysogenum* ATCC 11550 | 232 | 205 |
| XP_001226436 | 67.8 | *Chaetomium globosum* CBS 148.51 | 308 | 301 |
| CEP15980 | 66.5 | *Parasitella parasitica* | 393 | 200 |
| XP_957107 | 66.1 | *Neurospora crassa* | 293 | 292 |
| XP_008593736 | 65.8 | *Beauveria bassiana* ARSEF 2860 | 258 | 202 |
| XP_009853913 | 65.8 | *Neurospora tetrasperma* FGSC 2509 | 293 | 292 |
| KGQ12157 | 65.7 | *Beauveria bassiana* D1-5 | 232 | 207 |
| EQB52129 | 65.4 | *Colletotrichum gloeosporioides* Cg-14 | 229 | 205 |
| XP_007840161 | 65.0 | *Pestalotiopsis fici* W106-1 | 233 | 206 |

TABLE 6-continued

NCBI Protein Sequence Search of STCE1 WT Protein Sequence

| Accession Number | % ID | Organism | Subject Length | Alignment Length |
|---|---|---|---|---|
| XP_008020030 | 65.0 | *Setosphaeria turcica* Et28A | 227 | 203 |
| XP_001547700 | 58.4 | *Botrytis cinerea* T4 | 355 | 233 |
| P45699 | 48.2 | *Fusarium oxysporum* | 376 | 353 |

TABLE 7

Genome Quest Search for Homologs of STCE1-WT Protein Sequence

| Patent No/GENESEQ™ Identifier | % ID | Organism | Subject Length | Alignment Length |
|---|---|---|---|---|
| WO2011002063-0006 | 100 | *S. coccosporum* IFO 31817 | 295 | 295 |
| US20140051147-0038 | 100 | *S. coccosporum* IFO 31817 | 296 | 295 |
| US20140051147-0040 | 100 | *S. coccosporum* IFO 31817 | 299 | 295 |
| WO2012106824-0018 | 100 | *S. coccosporum* | 316 | 295 |
| US20140051147-0004 | 100 | *S. coccosporum* IFO 31817 | 298 | 294 |
| WO2005054475-AEA35116 | 99.66 | Fungi | 317 | 296 |
| WO2005056787-AEB69298 | 99.33 | Unidentified | 297 | 297 |
| CN103343111- BBB37873 | 85.05 | *C. thermophilum* | 217 | 214 |
| CN105155324-BCN40565 | 84.58 | *C. thermophilum* | 217 | 214 |
| WO2012089024-0002 | 82.55 | *T. terrestris*, *T. terrestris* NRRL 8126 Synthetic | 237 | 212 |
| WO2016090474-0358 | 81.36 | *C. olivicolor* | 309 | 295 |
| WO9804663-AAW46618 | 81.22 | *H. insolens* | 234 | 213 |
| GB2479462-AZN28533 | 80.75 | *H. insolens* | 213 | 213 |
| WO2007071820-0019 | 80.75 | *A. thermophilum* | 235 | 213 |
| US20150299682-0004 | 80 | *T. hyrcaniae* | 305 | 295 |
| CN103343111- BBB37871 | 79.59 | *C. thermophilum* | 314 | 294 |
| WO2015109405-0384 | 79.32 | *C. thermophilum* | 310 | 295 |
| WO2016090474-0328 | 77.71 | *C. olivicolor* | 335 | 314 |
| WO2009085859-0065 | 76.42 | *A. oryzae, H. insolens A. oryzae* Chimeric Synthetic | 1097 | 229 |
| CN101784659-0080 | 76.42 | rice koji mold | 1097 | 229 |
| WO2009085935-0075 | 76.42 | *A. oryzae*, rice koji mold, *A. oryzae* Synthetic, *A. oryzae H. insolens* Chimeric Synthetic, *A. oryzae* Chimeric Unidentified, *A. oryzae* Synthetic Unidentified | 1097 | 229 |
| WO9743409-0066 | 75.93 | *H. nigrescens, H. insolens* Chimeric, *H. nigrescens*, Hybrid | 306 | 295 |
| WO2016090472-0739 | 75.59 | *Melanocarpus albomyces* | 235 | 213 |
| WO2014086976-0036 | 74.06 | Artificial Sequence, Synthetic Unidentified | 278 | 293 |
| WO2012089024-0004 | 74.06 | *T. terrestris, T. terrestris* NRRL 8126 Synthetic | 299 | 293 |
| WO9407998-ABB04129 | 73.99 | *H. insolens* Synthetic | 284 | 296 |
| CN103184163-BAY17845 | 73.99 | *H. insolens* Synthetic | 305 | 296 |
| WO2007071818-0012 | 73.9 | *S. coccosporum, A. thermophilum* | 297 | 295 |
| WO2004053039-0003 | 73.72 | *T. terrestris, T. terrestis*, IAMA.A, locally born shuttle spore shell | 299 | 293 |
| US20050121156-0006 | 73.65 | *H. insolens* | 285 | 296 |
| WO9811239-0043 | 73.65 | *H. insolens* | 286 | 296 |
| WO9407998-ABB04141 | 73.65 | *H. insolens* Synthetic | 284 | 296 |
| WO9407998-ABB04140 | 73.65 | *H. insolens* Synthetic | 284 | 296 |
| WO2012106824-0007 | 73.65 | *H. insolens* | 284 | 296 |
| WO9407998-ABB04135 | 73.31 | *H. insolens* Synthetic | 284 | 296 |
| WO9743409-0056 | 73.65 | *H. insolens*; DSM 1800, *B. amyloliquefaciens* | 305 | 296 |
| WO9218599-0001 | 73.65 | empty | 304 | 296 |
| EP0633311-0002 | 73.65 | *H. insolens* | 305 | 296 |
| WO9218598-0002 | 73.65 | empty | 304 | 296 |
| JP2000217583-0031 | 73.65 | *H. insolens* | 304 | 296 |
| WO2012106824-0016 | 73.65 | *H. grisea* var. thermoidea | 305 | 296 |
| WO2013181760-0760 | 73.65 | *S. thermophilum*; CBS 625.91 | 305 | 296 |
| WO9803640-0003 | 73.65 | *H. insolens* | 305 | 296 |
| WO2008151999-0002 | 73.65 | *H. insolens, H. jecorina, T. reesei*, Artificial Sequence | 305 | 296 |
| WO2005056787-0002 | 73.65 | *H. insolens* MN200-1, *H. insolens*, Unidentified | 289 | 296 |
| CN103184163-0001 | 73.65 | *H. insolens* | 318 | 296 |
| WO0240997-0224 | 73.41 | *H. insolens* | 276 | 267 |
| WO2005054475-AEA35112 | 73.4 | Fungi | 286 | 297 |
| IN2003CH00919-0009 | 73.38 | empty | 299 | 293 |
| CN1198939-0004 | 73.31 | empty | 286 | 296 |

TABLE 7-continued

Genome Quest Search for Homologs of STCE1-WT Protein Sequence

| Patent No/GENESEQ™ Identifier | % ID | Organism | Subject Length | Alignment Length |
|---|---|---|---|---|
| WO9407998-ABB04139 | 73.31 | *H. insolens* Synthetic | 284 | 296 |
| WO9407998-ABB04131 | 73.31 | *H. insolens* Synthetic | 284 | 296 |
| WO9407998-ABB04132 | 73.31 | *H. insolens* Synthetic | 284 | 296 |
| WO9407998-ABB04137 | 73.31 | *H. insolens* Synthetic | 284 | 296 |
| WO9407998-ABB04138 | 73.31 | *H. insolens* Synthetic | 284 | 296 |
| WO9407998-ABB04133 | 72.97 | *H. insolens* Synthetic | 284 | 296 |
| JP2003070489-0002 | 73.31 | *H. insolens* | 305 | 296 |
| CN1151762-0007 | 73.31 | empty | 304 | 296 |
| CN1231689-0001 | 73.31 | empty | 304 | 296 |
| WO9218688-0001 | 73.31 | empty | 303 | 296 |
| CN1230988-0001 | 73.31 | empty | 305 | 296 |
| CN1230988-0002 | 73.31 | empty | 304 | 296 |
| CN1231689-0002 | 73.31 | empty | 302 | 296 |
| EP0959128-0003 | 73.06 | empty | 306 | 297 |
| CN101955921-1027 | 73.04 | empty | 297 | 293 |
| WO9407998-ABB04146 | 72.97 | *H. insolens* Synthetic | 284 | 296 |
| WO9219726- AAR28818 | 72.97 | *H. insolens* | 305 | 296 |
| WO9218688- AAR28300 | 72.97 | *H. insolens*; DSM 1800 | 305 | 296 |
| CN1151762-0008 | 72.97 | empty | 303 | 296 |
| WO9617994- AAG78352 | 72.97 | *H. insolens* Synthetic | 305 | 296 |
| WO9617994- AAG78356 | 72.97 | *H. insolens* | 305 | 296 |
| WO9617994- AAG78358 | 72.97 | *H. insolens* Synthetic | 305 | 296 |
| WO9617994- AAG78355 | 72.64 | *H. insolens* Synthetic | 305 | 296 |
| WO9617994- AAG78353 | 72.64 | *H. insolens* Synthetic | 305 | 296 |
| WO9617994- AAG78357 | 72.64 | *H. insolens* Synthetic | 305 | 296 |
| WO9617994- AAG78354 | 72.64 | *H. insolens* Synthetic | 305 | 296 |
| WO9617994- AAG78360 | 72.64 | *H. insolens* Synthetic | 305 | 296 |
| WO2007071820-0017 | 72.52 | *A. thermophilum* | 264 | 262 |
| WO9617994- AAG78359 | 72.3 | *H. insolens* Synthetic | 305 | 296 |
| WO9407998-ABB04147 | 71.62 | *H. insolens* Synthetic | 284 | 296 |
| WO2014138983-0859 | 71.33 | *T. australiensis* | 293 | 293 |
| US7361487-0006 | 71.28 | *A. thermophilum*; strain ALK04245 *C. thermophilum*; strain ALKO4265 Chimeric Synthetic | 315 | 296 |
| WO2007071820-0041 | 71.28 | *A. thermophilum, C. thermophilum* Chimeric | 311 | 296 |
| WO9407998-ABB04136 | 70.95 | *H. insolens* Synthetic | 267 | 296 |
| WO9617994- AAG78361 | 70.95 | *H. insolens* Synthetic | 305 | 296 |
| WO2012101206-0036 | 70.48 | *R. thermophila* | 260 | 271 |
| CN1230995-0003 | 70.27 | *A. thermophilum* Synthetic, *A. thermophilum* | 293 | 296 |
| WO2007071820-0040 | 70.07 | *S. indonesiacum, Scytalidium* sp.; indonesiacum | 300 | 294 |
| WO2012101206-0046 | 69.65 | | 277 | 257 |
| WO2012106824-0020 | 69.28 | *P. anserina* | 302 | 293 |
| WO9407998-ABB04143 | 69.26 | *H. insolens* Synthetic | 284 | 296 |
| WO9743409-0068 | 69.15 | *Cylindrocarpon*; sp. *H. insolens* Chimeric, Hybrid | 306 | 295 |
| WO9407998-ABB04145 | 68.92 | *H. insolens* Synthetic | 284 | 296 |
| WO2007071820-0039 | 68.71 | *H. jecorina A. thermophilum* Chimeric, *A. thermophilum* | 298 | 294 |
| WO2014026630-0002 | 68.49 | *S. fimicola*, ATCC 52644 | 294 | 292 |
| WO2014035458-0326 | 68.44 | *C. globosum* | 308 | 301 |
| WO2014101753-0002 | 68.03 | *H. hyalothermophila, Humicola* sp.; CBS454.80 | 286 | 294 |
| WO2012106824-0027 | 67.81 | *N. crassa* | 293 | 292 |
| WO9743409-0072 | 67.8 | *C. rosea f. catenulata, H. insolens* Chimeric, Hybrid | 304 | 295 |
| WO9743409-0070 | 67.34 | *F. anguioides H. insolens* Chimeric, *F. anguioides*, Hybrid | 308 | 297 |
| WO9743409-0074 | 65.54 | *T. roseum, T. roseum H. insolens* Chimeric, Hybrid | 307 | 296 |

Example 8

Alignment of GH45 Cellulases with STCE1-WT

Figure 6A:
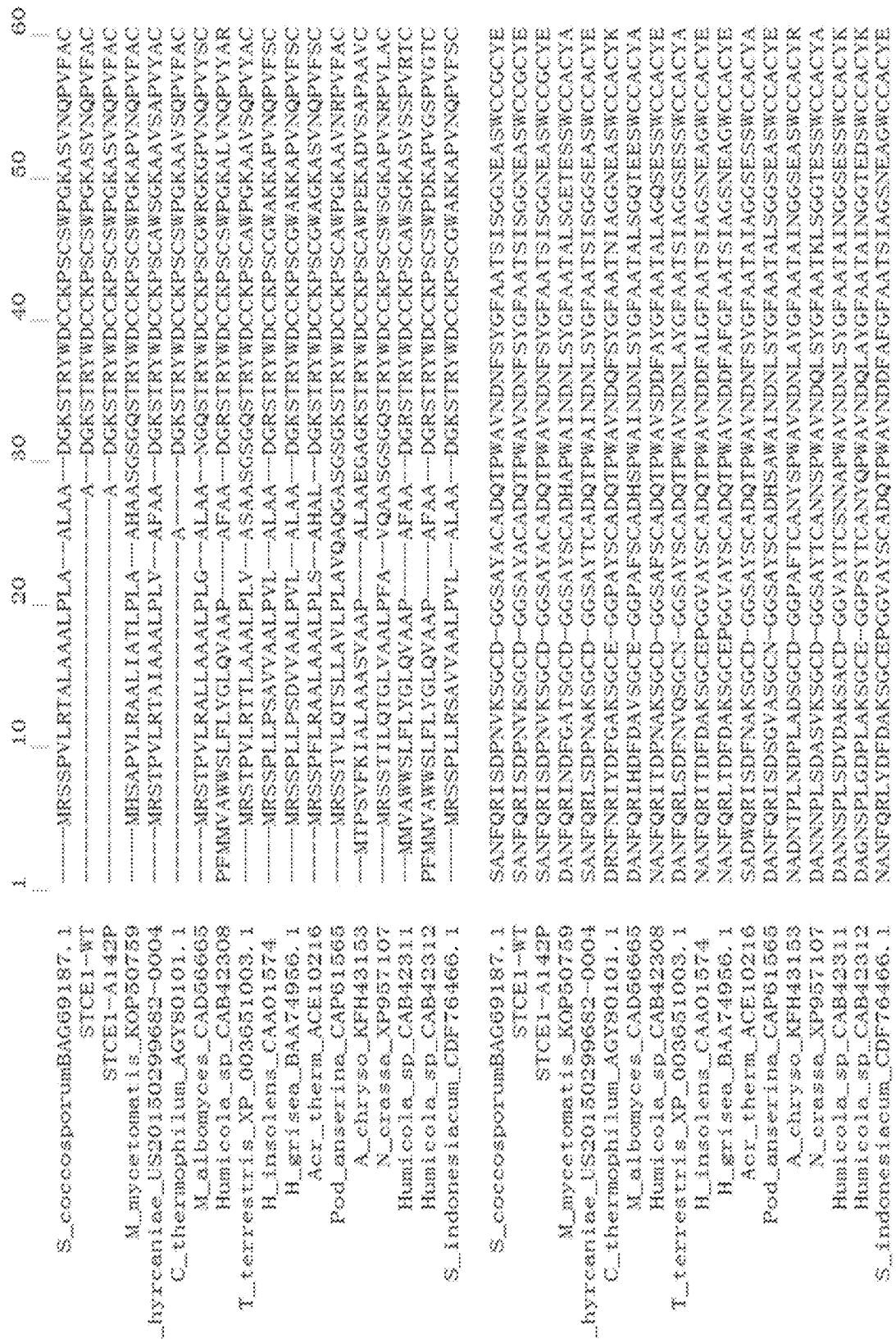
Figure 7:
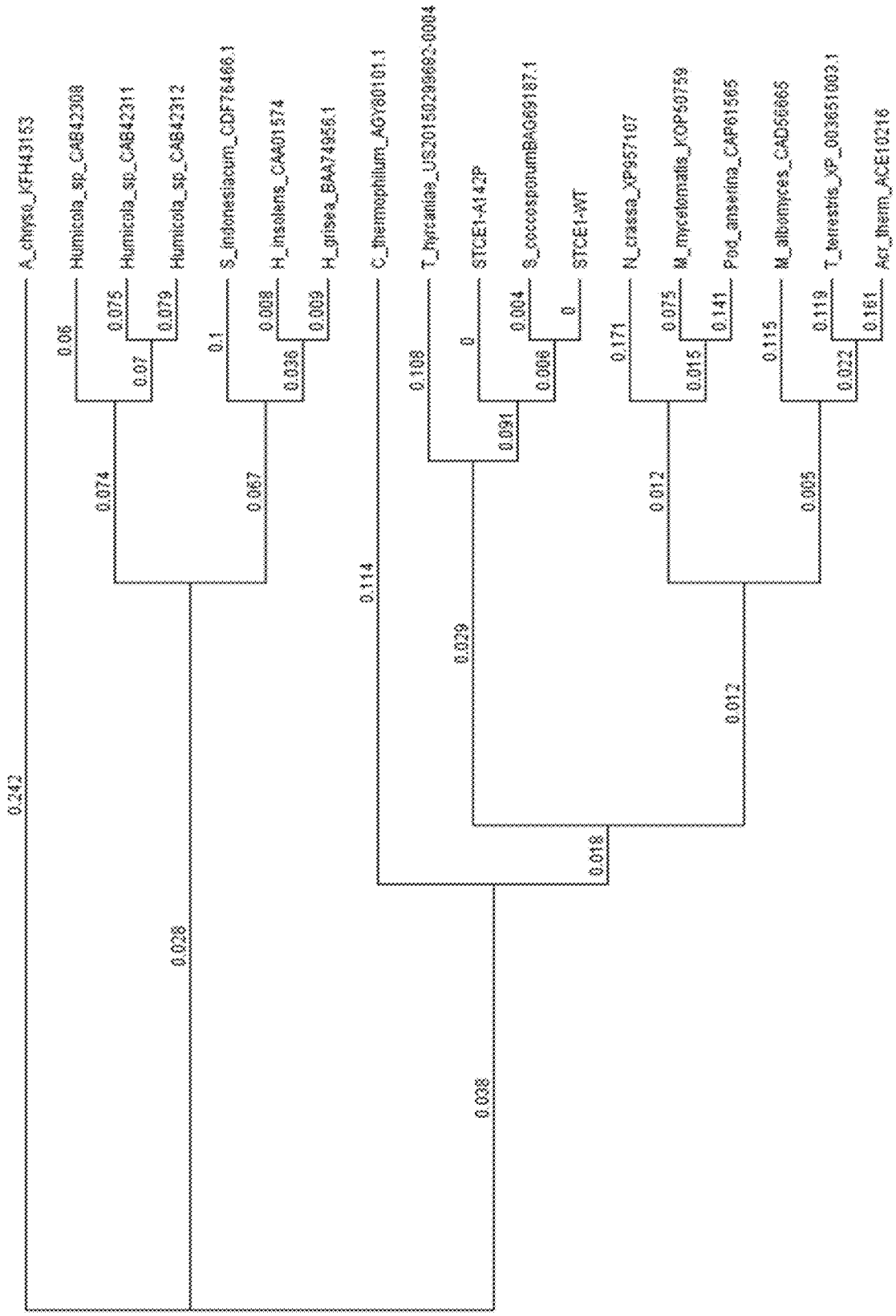
FIG. 7 provides a phylogenetic tree of STCE1-WT cellulase and variants thereof with other GH45 cellulases described in Example 7.

An alignment of the amino acid sequences of the following cellulases S_coccosporum_BAG69187.1 (SEQ ID NO:1), STCE1-WT (SEQ ID NO:5), STCE1-A142P (SEQ ID NO:8), *Madurella mycetomatis* (NCBI Accession No: KOP50759) (SEQ ID NO:2), S_indonesiacum (NCBI Accession No: CDF76466.1)(SEQ ID NO:29), C_thermophilum (NCBI Accession NO: AGY80101.1)(SEQ ID NO:19), M_albomyces (NCBI Accession No: CAD56665) (SEQ ID NO:20), H_insolens (NCBI Accession No: CAA01574.1)(SEQ ID NO:10), H_grisea (NCBI Accession No:BAA74956.1)(SEQ ID NO:23), T_terrestris (NCBI Accession No: XP_003651003.1)(SEQ ID NO:22), *Podospora anserina* S mat+ (NCBI Accession No: XP_001903789; GenBank accession number CAP61565.1) (SEQ ID NO:25), *Acremonium chrysogenum* (NCBI Accession NO: KFH43153)(SEQ ID NO:26), *Neurospora crassa* (NCBI Accession No: XP_957107)(SEQ ID NO:13), SEQ ID NO:4 from US20150299682 (SEQ ID NO:18), SEQ ID NO:66 from WO9743409 (Genome Quest Identifier: CAB42308) (SEQ ID NO:21), SEQ ID NO:6 from U.S. Pat. No. 7,361,487 (Genome Quest Identifier: ACE10216.1) (SEQ ID NO:24), SEQ ID NO:72 from WO9743409 (Genome Quest Identifier: CAB42311) (SEQ ID NO:27), and SEQ ID NO:74 from WO9743409 (Genome Quest Identifier: CAB42312) (SEQ ID NO:28) is shown in FIG. 6A-C. The sequences were aligned with default parameters using the MUSCLE program from Geneious software (Biomatters Ltd.) (Robert C. Edgar. MUSCLE: multiple sequence alignment with high accuracy and high throughput Nucl. Acids Res. (2004) 32 (5): 1792-1797). A phylogenetic tree for amino acid sequences of the mature forms of the subtilisins from FIG. 6 was built using the Geneious Tree builder program and is shown in FIG. 7.

Example 9

Identification of Additional Substitutions in STCE-1 Cellulase that Impart Improved Stability Under Multiple Conditions Additional substitutions on the STCE-1 cellulase backbone were generated using methods described in Example 2. Similarly to the evaluations described in Example 4, the activity and stability of the singly substituted cellulase variants was evaluated as described in Example 1. The relative activity and stability performance results are shown in Table 8, reported as performance index (PI) of variants versus STCE1-WT (SEQ ID NO:5).

TABLE 8

STCE-1 Cellulase Variants Showing Improved Activity and/or Improved Stability Performance Across Multiple Conditions.

| | | CMC | Stability Performance | | |
|---|---|---|---|---|---|
| Position | Variant | Activity, pH 8.2 | Detergent (OMO) and protease | Protease | Thermal |
| 4 | K4V | 1.0 | 1.3 | 1.4 | 1.1 |
| 20 | G20N | 1.2 | 1.2 | 1.3 | 0.8 |
| 23 | S23L | 1.2 | 1.5 | 1.2 | 0.9 |
| 29 | F29W | 1.1 | 1.6 | 1.2 | 1.0 |
| 32 | S32D | 1.1 | 2.2 | 1.7 | 0.9 |
| 32 | S32Y | 1.2 | 1.4 | 1.2 | 0.8 |
| 36 | Q36T | 1.1 | 1.8 | 1.6 | 1.1 |
| 44 | K44V | 1.1 | 1.5 | 1.0 | 1.1 |
| 51 | S51T | 1.2 | 2.0 | 1.2 | 1.1 |
| 77 | S77M | 1.0 | 1.5 | 1.3 | 1.1 |
| 77 | S77K | 1.1 | 1.3 | 1.4 | 1.1 |
| 80 | N80S | 1.2 | 1.3 | 1.3 | 1.1 |
| 87 | G87A | 1.1 | 1.3 | 1.3 | 1.2 |
| 90 | E90A | 1.2 | 1.2 | 0.9 | 1.0 |
| 97 | P97S | 1.4 | 2.2 | 1.0 | 1.1 |
| 98 | V98G | 1.1 | 1.7 | 1.2 | 1.1 |
| 99 | A99Y | 1.1 | 1.7 | 1.2 | 1.0 |
| 99 | A99E | 1.0 | 1.5 | 1.3 | 1.3 |
| 102 | T102K | 1.0 | 1.1 | 1.1 | 1.3 |
| 112 | G112T | 1.2 | 1.8 | 1.0 | 1.1 |
| 112 | G112S | 1.2 | 1.8 | 1.4 | 1.2 |
| 112 | G112V | 1.2 | 2.1 | 1.3 | 1.2 |
| 116 | T116V | 1.2 | 1.2 | 1.0 | 1.0 |
| 135 | S135T | 1.0 | 2.6 | 2.0 | 1.1 |
| 136 | P136E | 1.0 | 2.0 | 1.9 | 1.1 |
| 136 | P136K | 0.9 | 1.8 | 2.0 | 1.0 |
| 136 | P136S | 1.1 | 2.4 | 1.6 | 0.9 |
| 153 | S153D | 1.2 | 2.0 | 1.4 | 1.1 |
| 154 | Q154E | 1.0 | 2.6 | 1.9 | 1.0 |
| 157 | S157D | 1.1 | 1.8 | 1.1 | 1.1 |
| 161 | A161P | 0.9 | 2.0 | 1.7 | 0.9 |
| 161 | A161E | 1.2 | 2.2 | 1.4 | 1.2 |
| 163 | K163V | 1.2 | 2.3 | 1.4 | 1.1 |

TABLE 8-continued

STCE-1 Cellulase Variants Showing Improved Activity and/or Improved Stability Performance Across Multiple Conditions.

| | | CMC | Stability Performance | | |
|---|---|---|---|---|---|
| Position | Variant | Activity, pH 8.2 | Detergent (OMO) and protease | Protease | Thermal |
| 192 | L192V | 1.4 | 1.1 | 1.1 | 1.0 |
| 194 | A194S | 1.4 | 1.5 | 1.3 | 1.1 |
| 204 | G204S | 1.0 | 1.8 | 1.1 | 1.0 |
| 208 | V208H | 1.2 | 1.9 | 1.0 | 0.9 |
| 208 | V208K | 1.1 | 1.5 | 1.1 | 0.9 |
| 210 | T210V | 1.2 | 1.9 | 1.0 | 1.0 |
| 212 | P212S | 1.2 | 2.0 | 0.7 | 1.0 |
| 217 | S217G | 1.1 | 1.4 | 0.9 | 1.5 |
| 217 | S217M | 1.2 | 1.1 | 1.2 | 1.1 |
| 221 | S221L | 0.9 | 1.7 | 0.9 | 1.0 |
| 221 | S221M | 1.1 | 1.2 | 1.1 | 1.4 |
| 222 | S222A | 0.9 | 2.0 | 1.1 | 1.0 |
| 225 | S225K | 1.1 | 1.5 | 1.1 | 1.0 |
| 227 | K227R | 1.1 | 1.1 | 1.3 | 1.1 |
| 232 | S232T | 1.1 | 1.0 | 1.2 | 0.8 |

Example 10

Evaluation of Mutations that Improve Stability Across GH45 Cellulases

FIG. 8 provides a MUSCLE multiple sequence alignment of the catalytic domains of the following GH45 cellulases: STCE1-WT (SEQ ID NO: 5), *H. insolens* (SEQ ID NO: 11), *N. crassa* (SEQ ID NO:14) and *T. terrestris* 120H (SEQ ID NO:17). Single amino acid substitutions at positions that correspond to the positions (based on the multiple sequence alignment set forth in FIG. 8) that were shown to improve the stability of the STCE1-WT cellulase (as shown in Example 9) were evaluated in the related GH45 cellulases: *H. insolens*-WT (SEQ ID NO:11), *N. crassa*-WT (SEQ ID NO:14), and *T. terrestris*-120H (SEQ ID NO:17). The stability performance of these other GH45 variant cellulases and associated parents were measured under the test conditions described in Example 1, the results are shown in Tables 10, 11 and 12, reported as performance index (PI) of variants versus parent. Substituting amino acids at positions in other endoglucanases (e.g., *H. insolens*, *N. crassa* and *T. terrestris*) at positions that correspond to the positions that improved the stability of STCE1-WT yielded numerous GH45 variants with improved stability.

TABLE 10

Relative Performance Compared to *H. insolens*-WT, Reported as PI

| *H. insolens* enzyme, sequence numbering relative to *H. insolens* | Sequence numbering relative to mature STCE1-WT | Stability | |
|---|---|---|---|
| | | Detergent | Protease |
| WT (SEQ ID NO: 11) | (SEQ ID NO: 5) | | |
| *H. insolens*-WT (parent) | — | 1.0 | 1.0 |
| K20N | K20N | 1.4 | 0.3 |
| Q36T | Q36T | 1.6 | 0.9 |
| G113T | G112T | 2.0 | 1.3 |
| N154D | H153D | 2.0 | 0.9 |
| A162P | A161P | 2.0 | 1.8 |

TABLE 11

Relative Performance Compared to N. crassa-WT, Reported as PI

| N. crassa enzyme, sequence numbering relative to mature N. crassa WT (SEQ ID NO: 14) | Sequence numbering relative to mature STCE1-WT (SEQ ID NO: 5) | Stability Detergent | Stability Protease |
|---|---|---|---|
| N. crassa-WT (parent) | — | 1.0 | 1.0 |
| N38T | N36T | 5.0 | 35 |
| G114T | G112T | 2.0 | 27 |
| S155D | G153D | 40 | 0 |
| Q156E | Q154E | 81 | 0 |
| A163P | A161P | 15 | 64 |

TABLE 12

Relative Performance Compared to T. terrestris-WT, Reported as PI

| T. terrestris enzyme, sequence numbering relative to mature T. terrestris 120H (SEQ ID NO: 17) | Sequence numbering relative to mature STCE1-WT (SEQ ID NO: 5) | Stability Detergent | Stability Protease |
|---|---|---|---|
| T. terrestris-120H (parent) | — | 1.0 | 1.0 |
| A25L | A23L | 1.7 | 0 |
| Q38T | Q36T | 1.7 | 110 |
| G114T | G112T | 1.6 | 0 |
| S137T | S135T | 1.0 | 48 |
| S138E | S136E | 1.7 | 0 |
| Q156E | Q154E | 17 | 840 |

We claim:

1. A cellulase variant comprising an amino acid sequence comprising a substitution of A142P, wherein said variant has endoglucanase activity, wherein said variant has an amino acid sequence having at least 91% sequence identity to SEQ ID NO: 5, and wherein the amino acid positions of the variant, are numbered by correspondence with the amino acid sequence of SEQ ID NO:5.

2. The cellulase variant claim 1, wherein said variant has at least one improved property selected from improved thermostability, stability in the presence of one or more protease, and stability in the presence of one or more protease and one or more other detergent component when compared to a parent or reference polypeptide.

3. The cellulase variant of claim 1, wherein said variant comprises an amino acid sequence having at least 92%, 93%, 94%, 95%, 96%, 97%, 98%, or 99% amino acid sequence identity to the amino acid sequence of SEQ ID NO:5.

4. The cellulase variant of claim 1, wherein said variant is derived from a parent or reference polypeptide of SEQ ID NO: 5.

5. The cellulase variant of claim 4, wherein the parent or reference polypeptide comprises (i) an amino acid sequence having at least 92%, 93%, 94%, 95%, 96%, 97%, 98%, or 99% to amino acids 1-215 of SEQ ID NO:5.

6. The cellulase variant of claim 2, wherein the improved property is (i) improved thermostability and wherein said variant has a thermal performance index (PI) that is greater than 1 or 1.1; (ii) improved stability in the presence of one or more protease and wherein said variant has a PI that is greater than 1, 1.1, 1.5, or 2.0 when the stability of said variant is tested in the presence of said protease; and/or (iii) improved stability in the presence of one or more protease and one or more other detergent component, and wherein said variant has a PI that is greater than 1, 1.1, 1.5, 2.0, or 2.5 when the stability of said variant is tested in the presence of said protease and said other detergent component.

7. The cellulase variant of claim 6, wherein the PI is measured in accordance with the Cellulase Activity Assay of Example 1.

8. The cellulase variant of claim 6, wherein the other detergent component is a surfactant.

9. The cellulase variant of claim 1, wherein said variant, is a family GH45 cellulase.

10. A composition comprising the cellulase variant of claim 1.

11. The composition of claim 10, wherein said composition is selected from an enzyme composition, detergent composition, and fabric care composition.

12. The composition of claim 10, further comprising (i) one or more other enzymes selected from the group consisting of acyl transferases, amylases, alpha-amylases, beta-amylases, alpha-galactosidases, arabinases, arabinosidases, aryl esterases, beta-galactosidases, beta-glucanases, carrageenases, catalases, chondroitinases, cutinases, endo-beta-mannanases, exo-beta-mannanases, esterases, exo-mannanases, galactanases, glucoamylases, hemicellulases, hyaluronidases, keratinases, laccases, lactases, ligninases, lipases, lipolytic enzymes, lipoxygenases, mannanases, metalloproteases, oxidases, pectate lyases, pectin acetyl esterases, pectinases, pentosanases, perhydrolases, peroxidases, phenoloxidases, phosphatases, phospholipases, phytases, polygalacturonases, proteases, pullulanases, reductases, rhamnogalacturonases, second cellulase, beta-glucanases, tannases, transglutaminases, xylan acetyl-esterases, xylanases, and xylosidases; (ii) one or more surfactants; (iii) one or more ions selected from calcium and zinc; (iv) one or more adjunct ingredients; (v) one or more stabilizers; (vi) from about 0.001% to about 5.0 weight % of said cellulase variant of claim 1; (vii) one or more bleaching agents; and/or (viii) combinations thereof.

13. The composition of claim 10, wherein said composition is a laundry detergent.

14. The composition of claim 10, wherein the composition is in a form selected from a liquid, a powder, a granulated solid, a tablet, a sheet, and a unit dose.

15. The composition of claim 10, wherein said composition is phosphate-free and/or is boron-free.

* * * * *

SEQUENCE LISTING

```
<160> NUMBER OF SEQ ID NOS: 29

<210> SEQ ID NO 1
<211> LENGTH: 316
<212> TYPE: PRT
<213> ORGANISM: Staphylotrichum coccosporum

<400> SEQUENCE: 1

Met Arg Ser Ser Pro Val Leu Arg Thr Ala Leu Ala Ala Ala Leu Pro
1               5                   10                  15

Leu Ala Ala Leu Ala Ala Asp Gly Lys Ser Thr Arg Tyr Trp Asp Cys
                20                  25                  30

Cys Lys Pro Ser Cys Ser Trp Pro Gly Lys Ala Ser Val Asn Gln Pro
            35                  40                  45

Val Phe Ala Cys Ser Ala Asn Phe Gln Arg Ile Ser Asp Pro Asn Val
        50                  55                  60

Lys Ser Gly Cys Asp Gly Gly Ser Ala Tyr Ala Cys Ala Asp Gln Thr
65                  70                  75                  80

Pro Trp Ala Val Asn Asp Asn Phe Ser Tyr Gly Phe Ala Ala Thr Ser
                85                  90                  95

Ile Ser Gly Gly Asn Glu Ala Ser Trp Cys Cys Gly Cys Tyr Glu Leu
            100                 105                 110

Thr Phe Thr Ser Gly Pro Val Ala Gly Lys Thr Met Val Val Gln Ser
        115                 120                 125

Thr Ser Thr Gly Gly Asp Leu Gly Thr Asn His Phe Asp Leu Ala Met
    130                 135                 140

Pro Gly Gly Gly Val Gly Ile Phe Asp Gly Cys Ser Pro Gln Phe Gly
145                 150                 155                 160

Gly Leu Ala Gly Asp Arg Tyr Gly Gly Val Ser Ser Arg Ser Gln Cys
                165                 170                 175

Asp Ser Phe Pro Ala Ala Leu Lys Pro Gly Cys Tyr Trp Arg Phe Asp
            180                 185                 190

Trp Phe Lys Asn Ala Asp Asn Pro Thr Phe Thr Phe Arg Gln Val Gln
        195                 200                 205

Cys Pro Ser Glu Leu Val Ala Arg Thr Gly Cys Arg Arg Asn Asp Asp
    210                 215                 220

Gly Asn Phe Pro Val Phe Thr Pro Pro Ser Gly Gly Gln Ser Ser Ser
225                 230                 235                 240
```

```
Ser Ser Ser Ser Ser Ala Lys Pro Thr Ser Thr Ser Thr
            245                 250                 255

Thr Ser Thr Lys Ala Thr Ser Thr Ser Thr Ala Ser Ser Gln Thr
        260                 265                 270

Ser Ser Ser Thr Gly Gly Gly Cys Ala Ala Gln Arg Trp Ala Gln Cys
    275                 280                 285

Gly Gly Ile Gly Phe Ser Gly Cys Thr Thr Cys Val Ser Gly Thr Thr
        290                 295                 300

Cys Asn Lys Gln Asn Asp Trp Tyr Ser Gln Cys Leu
305                 310                 315

<210> SEQ ID NO 2
<211> LENGTH: 238
<212> TYPE: PRT
<213> ORGANISM: Madurella mycetomatis

<400> SEQUENCE: 2

Met His Ser Ala Pro Val Leu Arg Ala Ala Leu Ile Ala Thr Leu Pro
1               5                   10                  15

Leu Ala Ala His Ala Ala Ser Gly Ser Gly Gln Ser Thr Arg Tyr Trp
            20                  25                  30

Asp Cys Cys Lys Pro Ser Cys Ser Trp Pro Gly Lys Ala Pro Val Asn
        35                  40                  45

Gln Pro Val Phe Ala Cys Asp Ala Asn Phe Gln Arg Ile Asn Asp Phe
    50                  55                  60

Gly Ala Thr Ser Gly Cys Asp Gly Gly Ser Ala Tyr Ser Cys Ala Asp
65                  70                  75                  80

His Ala Pro Trp Ala Ile Asn Asp Asn Leu Ser Tyr Gly Phe Ala Ala
                85                  90                  95

Thr Ala Leu Ser Gly Glu Thr Glu Ser Ser Trp Cys Cys Ala Cys Tyr
            100                 105                 110

Ala Leu Thr Phe Thr Ser Gly Pro Val Ala Gly Lys Thr Met Val Val
        115                 120                 125

Gln Ser Thr Ser Thr Gly Gly Asp Leu Gly Ser Asn His Phe Asp Leu
    130                 135                 140

Asn Ile Pro Gly Gly Gly Val Gly Leu Phe Asp Gly Cys Thr Pro Gln
145                 150                 155                 160

Phe Gly Gly Leu Pro Gly Ala Gln Tyr Gly Gly Ile Ser Asp Arg Ser
                165                 170                 175

Gln Cys Ser Ser Phe Pro Ser Gln Leu Gln Pro Gly Cys Asn Trp Arg
            180                 185                 190

Phe Asp Trp Phe Met Asn Ala Asp Asn Pro Ser Phe Thr Phe Asp Gln
        195                 200                 205

Val Gln Cys Pro Asp Glu Leu Val Ala Arg Thr Gly Cys Arg Arg Ser
    210                 215                 220

Asp Asp Ala Asn Phe Pro Ala Phe Ser Pro Ser Arg Leu
225                 230                 235

<210> SEQ ID NO 3
<211> LENGTH: 951
<212> TYPE: DNA
<213> ORGANISM: Staphylotrichum coccosporum

<400> SEQUENCE: 3
atgcgttcct cccccgtcct ccgcacggcc ctggccgctg ccctcccct  ggccgccctc    60 gctgccgatg gcaagtcgac ccgctactgg gactgttgca agccgtcgtg ctcgtggccc   120
```

-continued

```
ggcaaggcct cggtgaacca gcccgtcttc gcctgcagcg ccaacttcca gcgcatcagc    180
gaccccaacg tcaagtcggg ctgcgacggc ggctccgcct acgcctgcgc cgaccagacc    240
ccgtgggccg tcaacgacaa cttctcgtac ggcttcgccg ccacgtccat ctcgggcggc    300
aacgaggcct cgtggtgctg tggctgctac gagctgacct tcacctcggg ccccgtcgct    360
ggcaagacca tggttgtcca gtccaccctcg accggcggcg acctcggcac caaccacttc    420
gacctggcca tgcccggtgg tggtgtcggc atcttcgacg gctgctcgcc ccagttcggc    480
ggcctcgccg gcgaccgcta cggcggcgtc tcgtcgcgca gccagtgcga ctcgttcccc    540
gccgccctca gcccggctg ctactggcgc ttcgactggt tcaagaacgc cgacaacccg    600
accttcacct tccgccaggt ccagtgcccg tcggagctcg tcgcccgcac cggctgccgc    660
cgcaacgacg acggcaactt ccccgtcttc accctccct cgggcggtca gtcctcctcg    720
tcttcctcct ccagcagcgc caagcccacc tccacctcca cctcgaccac ctccaccaag    780
gctacctcca ccacctcgac cgcctccagc cagacctcgt cgtccaccgg cggcggctgc    840
gccgcccagc gctgggcgca gtgcggcggc atcgggttct cgggctgcac cacgtgcgtc    900
agcggcacca cctgcaacaa gcagaacgac tggtactcgc agtgcctttg a             951
```

```
<210> SEQ ID NO 4
<211> LENGTH: 316
<212> TYPE: PRT
<213> ORGANISM: Staphylotrichum coccosporum

<400> SEQUENCE: 4
```

```
Met Arg Ser Ser Pro Val Leu Arg Thr Ala Leu Ala Ala Ala Leu Pro
1               5                   10                  15

Leu Ala Ala Leu Ala Ala Asp Gly Lys Ser Thr Arg Tyr Trp Asp Cys
            20                  25                  30

Cys Lys Pro Ser Cys Ser Trp Pro Gly Lys Ala Ser Val Asn Gln Pro
        35                  40                  45

Val Phe Ala Cys Ser Ala Asn Phe Gln Arg Ile Ser Asp Pro Asn Val
    50                  55                  60

Lys Ser Gly Cys Asp Gly Gly Ser Ala Tyr Ala Cys Ala Asp Gln Thr
65                  70                  75                  80

Pro Trp Ala Val Asn Asp Asn Phe Ser Tyr Gly Phe Ala Ala Thr Ser
                85                  90                  95

Ile Ser Gly Gly Asn Glu Ala Ser Trp Cys Cys Gly Cys Tyr Glu Leu
            100                 105                 110

Thr Phe Thr Ser Gly Pro Val Ala Gly Lys Thr Met Val Val Gln Ser
        115                 120                 125

Thr Ser Thr Gly Gly Asp Leu Gly Thr Asn His Phe Asp Leu Ala Met
    130                 135                 140

Pro Gly Gly Gly Val Gly Ile Phe Asp Gly Cys Ser Pro Gln Phe Gly
145                 150                 155                 160

Gly Leu Ala Gly Asp Arg Tyr Gly Gly Val Ser Ser Arg Ser Gln Cys
                165                 170                 175

Asp Ser Phe Pro Ala Ala Leu Lys Pro Gly Cys Tyr Trp Arg Phe Asp
            180                 185                 190

Trp Phe Lys Asn Ala Asp Asn Pro Thr Phe Thr Phe Arg Gln Val Gln
        195                 200                 205

Cys Pro Ser Glu Leu Val Ala Arg Thr Gly Cys Arg Arg Asn Asp Asp
    210                 215                 220
```

Gly Asn Phe Pro Val Phe Thr Pro Pro Ser Gly Gln Ser Ser Ser
225                 230                 235                 240

Ser Ser Ser Ser Ser Ala Lys Pro Thr Ser Thr Thr Ser Thr
            245                 250                 255

Thr Ser Thr Lys Ala Thr Ser Thr Thr Ser Thr Ala Ser Ser Gln Thr
            260                 265                 270

Ser Ser Ser Thr Gly Gly Cys Ala Ala Gln Arg Trp Ala Gln Cys
        275                 280                 285

Gly Gly Ile Gly Phe Ser Gly Cys Thr Thr Cys Val Ser Gly Thr Thr
        290                 295                 300

Cys Asn Lys Gln Asn Asp Trp Tyr Ser Gln Cys Leu
305                 310                 315

<210> SEQ ID NO 5
<211> LENGTH: 295
<212> TYPE: PRT
<213> ORGANISM: Staphylotrichum coccosporum

<400> SEQUENCE: 5

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
        115                 120                 125

Gly Ile Phe Asp Gly Cys Ser Pro Gln Phe Gly Gly Leu Ala Gly Asp
    130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser
    210                 215                 220

Ser Ala Lys Pro Thr Ser Thr Ser Thr Thr Thr Ser Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270

```
Ser Gly Cys Thr Thr Cys Val Ser Gly Thr Thr Cys Asn Lys Gln Asn
        275                 280                 285

Asp Trp Tyr Ser Gln Cys Leu
        290                 295

<210> SEQ ID NO 6
<211> LENGTH: 214
<212> TYPE: PRT
<213> ORGANISM: Staphylotrichum coccosporum

<400> SEQUENCE: 6

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
                20                  25                  30

Ala Asn Phe Gln Arg Ile Ser Asp Pro Asn Val Lys Ser Gly Cys Asp
            35                  40                  45

Gly Gly Ser Ala Tyr Ala Cys Ala Asp Gln Thr Pro Trp Ala Val Asn
        50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Gly
                100                 105                 110

Asp Leu Gly Thr Asn His Phe Asp Leu Ala Met Pro Gly Gly Gly Val
            115                 120                 125

Gly Ile Phe Asp Gly Cys Ser Pro Gln Phe Gly Gly Leu Ala Gly Asp
        130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly
        210

<210> SEQ ID NO 7
<211> LENGTH: 338
<212> TYPE: PRT
<213> ORGANISM: artificial sequence
<220> FEATURE:
<223> OTHER INFORMATION: variant of BPN' protein

<400> SEQUENCE: 7

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
        50                  55                  60
```

```
Gly Thr His Val Ala Gly Thr Val Ala Ala Leu Asn Asn Ser Ile Gly
 65                  70                  75                  80

Val Leu Gly Val Ala Pro Ser Ala Ser Leu Tyr Ala Val Lys Val Leu
                 85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Leu Asn Gly Thr Ser Met Ala Ser
    210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln Lys Ser Phe Pro Glu Val Val Gly Lys Thr Val Asp Gln
        275                 280                 285

Ala Arg Glu Tyr Phe Thr Leu His Tyr Pro Gln Tyr Asp Val Tyr Phe
    290                 295                 300

Leu Pro Glu Gly Ser Pro Val Thr Leu Asp Leu Arg Tyr Asn Arg Val
305                 310                 315                 320

Lys Val Phe Tyr Asn Pro Gly Thr Asn Val Val Asn His Val Pro His
                325                 330                 335

Val Gly

<210> SEQ ID NO 8
<211> LENGTH: 295
<212> TYPE: PRT
<213> ORGANISM: artificial sequence
<220> FEATURE:
<223> OTHER INFORMATION: mature form of the STCE1-A142P variant

<400> SEQUENCE: 8

Ala Asp Gly Lys Ser Thr Arg Tyr Trp Asp Cys Cys Lys Pro Ser Cys
  1               5                  10                  15

Ser Trp Pro Gly Lys Ala Ser Val Asn Gln Pro Val Phe Ala Cys Ser
                 20                  25                  30

Ala Asn Phe Gln Arg Ile Ser Asp Pro Asn Val Lys Ser Gly Cys Asp
             35                  40                  45

Gly Gly Ser Ala Tyr Ala Cys Ala Asp Gln Thr Pro Trp Ala Val Asn
         50                  55                  60

Asp Asn Phe Ser Tyr Gly Phe Ala Ala Thr Ser Ile Ser Gly Gly Asn
 65                  70                  75                  80
```

```
Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
            115                 120                 125

Gly Ile Phe Asp Gly Cys Ser Pro Gln Phe Gly Gly Leu Pro Gly Asp
        130                 135                 140

Arg Tyr Gly Gly Val Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
            195                 200                 205

Phe Thr Pro Pro Ser Gly Gly Gln Ser Ser Ser Ser Ser Ser Ser Ser
    210                 215                 220

Ser Ala Lys Pro Thr Ser Thr Ser Thr Ser Thr Ser Thr Lys Ala
225                 230                 235                 240

Thr Ser Thr Thr Ser Thr Ala Ser Ser Gln Thr Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
            275                 280                 285

Asp Trp Tyr Ser Gln Cys Leu
        290                 295

<210> SEQ ID NO 9
<211> LENGTH: 1060
<212> TYPE: DNA
<213> ORGANISM: Humicola insolens

<400> SEQUENCE: 9
ggatccaaga tgcgttcctc ccccctcctc ccgtccgccg ttgtggccgc cctgccggtg      60
ttggcccttg ccgctgatgg caggtccacc cgctactggg actgctgcaa gccttcgtgc     120
ggctgggcca agaaggctcc cgtgaaccag cctgtctttt cctgcaacgc caacttccag     180
cgtatcacgg acttcgacgc caagtccggc tgcgagccgg cggtgtcgc ctactcgtgc      240 gccgaccaga ccccatgggc tgtgaacgac gacttcgcgc tcggttttgc tgccacctct     300
attgccggca gcaatgaggc gggctggtgc tgcgcctgct acgagctcac cttcacatcc     360
ggtcctgttg ctggcaagaa gatggtcgtc cagtccacca gcactggcgg tgatcttggc     420
agcaaccact cgatctcaa catccccggc ggcggcgtcg gcatcttcga cggatgcact      480
ccccagttcg gcggtctgcc cggccagcgc tacgcggca tctcgtcccg caacgagtgc      540
gatcggttcc ccgacgccct caagcccggc tgctactggc gcttcgactg gttcaagaac     600
gccgacaatc cgagcttcag cttcgtcag gtccagtgcc cagccgagct cgtcgctcgc      660
accggatgcc gccgcaacga cgacggcaac ttccctgccg tccagatccc ctccagcagc     720
accagctctc cggtcaacca gcctaccagc accagcacca cgtccacctc caccacctcg     780
agcccgccag tccagcctac gactcccagc ggctgcactg ctgagaggtg ggctcagtgc     840
ggcggcaatg gctggagcgg ctgcaccacc tgcgtcgctg gcagcacttg cacgaagatt     900
```

-continued

```
aatgactggt accatcagtg cctgtagacg cagggcagct tgagggcctt actggtggcc      960
gcaacgaaat gacactccca atcactgtat tagttcttgt acataatttc gtcatccctc     1020
cagggattgt cacataaatg caatgaggaa caatgagtac                           1060
```

<210> SEQ ID NO 10
<211> LENGTH: 305
<212> TYPE: PRT
<213> ORGANISM: Humicola insolens

<400> SEQUENCE: 10

```
Met Arg Ser Ser Pro Leu Leu Pro Ser Ala Val Val Ala Ala Leu Pro
1               5                   10                  15

Val Leu Ala Leu Ala Ala Asp Gly Arg Ser Thr Arg Tyr Trp Asp Cys
                20                  25                  30

Cys Lys Pro Ser Cys Gly Trp Ala Lys Lys Ala Pro Val Asn Gln Pro
            35                  40                  45

Val Phe Ser Cys Asn Ala Asn Phe Gln Arg Ile Thr Asp Phe Asp Ala
        50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Ser Ser Thr Ser Ser
225                 230                 235                 240

Pro Val Asn Gln Pro Thr Ser Thr Ser Thr Ser Thr Thr
                245                 250                 255

Ser Ser Pro Pro Val Gln Pro Thr Pro Ser Gly Cys Thr Ala Glu
            260                 265                 270

Arg Trp Ala Gln Cys Gly Gly Asn Gly Trp Ser Gly Cys Thr Thr Cys
        275                 280                 285

Val Ala Gly Ser Thr Cys Thr Lys Ile Asn Asp Trp Tyr His Gln Cys
    290                 295                 300

Leu
305
```

<210> SEQ ID NO 11
<211> LENGTH: 284
<212> TYPE: PRT
<213> ORGANISM: Humicola insolens

<400> SEQUENCE: 11

Ala Asp Gly Arg Ser Thr Arg Tyr Trp Asp Cys Cys Lys Pro Ser Cys
1               5                   10                  15

Gly Trp Ala Lys Lys Ala Pro Val Asn Gln Pro Val Phe Ser Cys Asn
            20                  25                  30

Ala Asn Phe Gln Arg Ile Thr Asp Phe Asp Ala Lys Ser Gly Cys Glu
        35                  40                  45

Pro Gly Gly Val Ala Tyr Ser Cys Ala Asp Gln Thr Pro Trp Ala Val
    50                  55                  60

Asn Asp Asp Phe Ala Leu Gly Phe Ala Ala Thr Ser Ile Ala Gly Ser
65                  70                  75                  80

Asn Glu Ala Gly Trp Cys Cys Ala Cys Tyr Glu Leu Thr Phe Thr Ser
                85                  90                  95

Gly Pro Val Ala Gly Lys Lys Met Val Val Gln Ser Thr Ser Thr Gly
            100                 105                 110

Gly Asp Leu Gly Ser Asn His Phe Asp Leu Asn Ile Pro Gly Gly Gly
        115                 120                 125

Val Gly Ile Phe Asp Gly Cys Thr Pro Gln Phe Gly Gly Leu Pro Gly
    130                 135                 140

Gln Arg Tyr Gly Gly Ile Ser Ser Arg Asn Glu Cys Asp Arg Phe Pro
145                 150                 155                 160

Asp Ala Leu Lys Pro Gly Cys Tyr Trp Arg Phe Asp Trp Phe Lys Asn
                165                 170                 175

Ala Asp Asn Pro Ser Phe Ser Phe Arg Gln Val Gln Cys Pro Ala Glu
            180                 185                 190

Leu Val Ala Arg Thr Gly Cys Arg Arg Asn Asp Asp Gly Asn Phe Pro
        195                 200                 205

Ala Val Gln Ile Pro Ser Ser Thr Ser Ser Pro Val Asn Gln Pro
    210                 215                 220

Thr Ser Thr Ser Thr Thr Ser Thr Ser Thr Thr Ser Ser Pro Val
225                 230                 235                 240

Gln Pro Thr Thr Pro Ser Gly Cys Thr Ala Glu Arg Trp Ala Gln Cys
                245                 250                 255

Gly Gly Asn Gly Trp Ser Gly Cys Thr Thr Cys Val Ala Gly Ser Thr
            260                 265                 270

Cys Thr Lys Ile Asn Asp Trp Tyr His Gln Cys Leu
        275                 280

<210> SEQ ID NO 12
<211> LENGTH: 882
<212> TYPE: DNA
<213> ORGANISM: Neurospora crassa

<400> SEQUENCE: 12
atgcgctcct ccactattct gcaaaccggg ctagtggccg ctcttccttt cgccgtccag    60
gctgcttccg gatccggcca gtccaccaga tattgggact gctgcaaacc atcttgctcc   120
tggtccggca aggctcctgt caaccgaccc gtcctcgctt gcgacgcaaa caacaacccc   180
ctgagcgacg ccagtgtcaa gtctggatgt gatggcggtt ctgcatacac ctgtgccaac   240
aactcaccat gggcggtgaa cgaccagctc tcctacggct tgccgccac gaaactcagt   300 ggtggaaccg agtcatcttg gtgctgtgcc tgttatgccc ttaccttcac ttcgggccct   360
gttgctggca gaccttggt cgttcagtct accgtaccg gcggtgatct cggctccaac   420
cacttcgata tcaacatgcc cggcggcggc gtcggcctgt tgatggatg taaacgacag   480

| | | |
|---|---|---|
| ttcggcggtc tcccccggcgc tcaatatggc ggcatcagct cccgcagcca gtgcgactcg | 540 | |
| ttccctgccg ctctcaagcc cggttgccag tggcgcttcg actggttcca gaacgccgat | 600 | |
| aacccgaact tcaccttcaa gcaggtccaa tgcccatccg agctcacatc ccgcaccggc | 660 | |
| tgcaagcgaa acgacgactc ccaattccct gtcttcactc cgccctctgg tggaggcagt | 720 | |
| aaccccctcta ctccgacaac ccctccctct tcaggcggcg gttccggatg tacagcggat | 780 | |
| aaatacgctc aatgtggtgg ctcggggtgg tctggctgca ccaactgccc gtctggatcg | 840 | |
| acctgcaaga ctatcaacga ttattaccat cagtgtgcct ga | 882 | |

```
<210> SEQ ID NO 13
<211> LENGTH: 293
<212> TYPE: PRT
<213> ORGANISM: Neurospora crassa

<400> SEQUENCE: 13
```

Met Arg Ser Ser Thr Ile Leu Gln Thr Gly Leu Val Ala Ala Leu Pro
1               5                   10                  15

Phe Ala Val Gln Ala Ala Ser Gly Ser Gly Gln Ser Thr Arg Tyr Trp
            20                  25                  30

Asp Cys Cys Lys Pro Ser Cys Ser Trp Ser Gly Lys Ala Pro Val Asn
        35                  40                  45

Arg Pro Val Leu Ala Cys Asp Ala Asn Asn Asn Pro Leu Ser Asp Ala
    50                  55                  60

Ser Val Lys Ser Gly Cys Asp Gly Gly Ser Ala Tyr Thr Cys Ala Asn
65                  70                  75                  80

Asn Ser Pro Trp Ala Val Asn Asp Gln Leu Ser Tyr Gly Phe Ala Ala
                85                  90                  95

Thr Lys Leu Ser Gly Gly Thr Glu Ser Ser Trp Cys Cys Ala Cys Tyr
            100                 105                 110

Ala Leu Thr Phe Thr Ser Gly Pro Val Ala Gly Lys Thr Leu Val Val
        115                 120                 125

Gln Ser Thr Ser Thr Gly Gly Asp Leu Gly Ser Asn His Phe Asp Ile
    130                 135                 140

Asn Met Pro Gly Gly Gly Val Gly Leu Phe Asp Gly Cys Lys Arg Gln
145                 150                 155                 160

Phe Gly Gly Leu Pro Gly Ala Gln Tyr Gly Gly Ile Ser Ser Arg Ser
                165                 170                 175

Gln Cys Asp Ser Phe Pro Ala Ala Leu Lys Pro Gly Cys Gln Trp Arg
            180                 185                 190

Phe Asp Trp Phe Gln Asn Ala Asp Asn Pro Asn Phe Thr Phe Lys Gln
        195                 200                 205

Val Gln Cys Pro Ser Glu Leu Thr Ser Arg Thr Gly Cys Lys Arg Asn
    210                 215                 220

Asp Asp Ser Gln Phe Pro Val Phe Thr Pro Ser Gly Gly Gly Ser
225                 230                 235                 240

Asn Pro Ser Thr Pro Thr Thr Pro Ser Ser Gly Gly Gly Ser Gly
                245                 250                 255

Cys Thr Ala Asp Lys Tyr Ala Cys Gly Gly Ser Gly Trp Ser Gly
            260                 265                 270

Cys Thr Asn Cys Pro Ser Gly Ser Thr Cys Lys Thr Ile Asn Asp Tyr
        275                 280                 285

Tyr His Gln Cys Ala
    290

```
<210> SEQ ID NO 14
<211> LENGTH: 272
<212> TYPE: PRT
<213> ORGANISM: Neurospora crassa

<400> SEQUENCE: 14

Ala Ser Gly Ser Gly Gln Ser Thr Arg Tyr Trp Asp Cys Cys Lys Pro
1               5                   10                  15

Ser Cys Ser Trp Ser Gly Lys Ala Pro Val Asn Arg Pro Val Leu Ala
            20                  25                  30

Cys Asp Ala Asn Asn Asn Pro Leu Ser Asp Ala Ser Val Lys Ser Gly
        35                  40                  45

Cys Asp Gly Gly Ser Ala Tyr Thr Cys Ala Asn Asn Ser Pro Trp Ala
    50                  55                  60

Val Asn Asp Gln Leu Ser Tyr Gly Phe Ala Ala Thr Lys Leu Ser Gly
65                  70                  75                  80

Gly Thr Glu Ser Ser Trp Cys Cys Ala Cys Tyr Ala Leu Thr Phe Thr
                85                  90                  95

Ser Gly Pro Val Ala Gly Lys Thr Leu Val Val Gln Ser Thr Ser Thr
            100                 105                 110

Gly Gly Asp Leu Gly Ser Asn His Phe Asp Ile Asn Met Pro Gly Gly
        115                 120                 125

Gly Val Gly Leu Phe Asp Gly Cys Lys Arg Gln Phe Gly Gly Leu Pro
    130                 135                 140

Gly Ala Gln Tyr Gly Gly Ile Ser Ser Arg Ser Gln Cys Asp Ser Phe
145                 150                 155                 160

Pro Ala Ala Leu Lys Pro Gly Cys Gln Trp Arg Phe Asp Trp Phe Gln
                165                 170                 175

Asn Ala Asp Asn Pro Asn Phe Thr Phe Lys Gln Val Gln Cys Pro Ser
            180                 185                 190

Glu Leu Thr Ser Arg Thr Gly Cys Lys Arg Asn Asp Asp Ser Gln Phe
        195                 200                 205

Pro Val Phe Thr Pro Pro Ser Gly Gly Ser Asn Pro Ser Thr Pro
    210                 215                 220

Thr Thr Pro Pro Ser Ser Gly Gly Gly Ser Gly Cys Thr Ala Asp Lys
225                 230                 235                 240

Tyr Ala Gln Cys Gly Gly Ser Gly Trp Ser Gly Cys Thr Asn Cys Pro
                245                 250                 255

Ser Gly Ser Thr Cys Lys Thr Ile Asn Asp Tyr Tyr His Gln Cys Ala
            260                 265                 270

<210> SEQ ID NO 15
<211> LENGTH: 897
<212> TYPE: DNA
<213> ORGANISM: Thielavia terrestris

<400> SEQUENCE: 15
atgcgctcta ctcccgttct tcgcacaacc ctggccgctg cacttcctct ggtcgcctcc      60
gcggccagtg gcagtggcca gtccacgaga tactgggact gctgcaagcc gtcgtgcgct     120
tggcccggga aggccgccgt cagccaaccg gtctacgcgt gcgatgccaa cttccagcgc     180
ctgtccgact tcaatgtcca gtcgggctgc aacggcggct cggcctactc ctgcgccgac     240
cagactccct gggcggtgaa cgacaatctc gcctacggct cgccgcgac gagcatcgcc     300 ggcgggtccg aatcctcgtg gtgctgcgcc tgctacgcgc tcaccttcac ttccggtccc     360
gtcgccggca agacaatggt ggtgcagtca acgagcactg gcggcgacct gggaagtaac     420
```

-continued

```
catttcgata tcgccatgcc cggcggcggc gtgggcatct tcaacggctg cagctcgcag    480
ttcggcggcc tccccggcgc tcaatacggc ggcatttcgt cgcgcgacca gtgcgattcc    540
ttccccgcgc cgctcaagcc cggctgccag tggcggtttg actggttcca gaacgccgac    600
aacccgacgt tcacgttcca gcaggtgcag tgccccgccg agatcgttgc ccgctccggc    660
tgcaagcgca acgacgactc cagcttcccc gtcttcaccc ccccaagcgg tggcaacggt    720
ggcaccggga cgcccacgtc gactgcgcct gggtcgggcc agacgtctcc cggcggcggc    780
agtggctgca cgtctcagaa gtgggctcag tgcggtggca tcggcttcag cggatgcacc    840
acctgtgtct ctggcaccac ctgccagaag ttgaacgact actactcgca gtgcctc       897
```

<210> SEQ ID NO 16
<211> LENGTH: 299
<212> TYPE: PRT
<213> ORGANISM: Thielavia terrestris

<400> SEQUENCE: 16

```
Met Arg Ser Thr Pro Val Leu Arg Thr Thr Leu Ala Ala Ala Leu Pro
1               5                   10                  15

Leu Val Ala Ser Ala Ala Ser Gly Ser Gly Gln Ser Thr Arg Tyr Trp
            20                  25                  30

Asp Cys Cys Lys Pro Ser Cys Ala Trp Pro Gly Lys Ala Ala Val Ser
        35                  40                  45

Gln Pro Val Tyr Ala Cys Asp Ala Asn Phe Gln Arg Leu Ser Asp Phe
    50                  55                  60

Asn Val Gln Ser Gly Cys Asn Gly Gly Ser Ala Tyr Ser Cys Ala Asp
65                  70                  75                  80

Gln Thr Pro Trp Ala Val Asn Asp Asn Leu Ala Tyr Gly Phe Ala Ala
                85                  90                  95

Thr Ser Ile Ala Gly Gly Ser Glu Ser Ser Trp Cys Cys Ala Cys Tyr
            100                 105                 110

Ala Leu Thr Phe Thr Ser Gly Pro Val Ala Gly Lys Thr Met Val Val
        115                 120                 125

Gln Ser Thr Ser Thr Gly Gly Asp Leu Gly Ser Asn His Phe Asp Ile
    130                 135                 140

Ala Met Pro Gly Gly Gly Val Gly Ile Phe Asn Gly Cys Ser Ser Gln
145                 150                 155                 160

Phe Gly Gly Leu Pro Gly Ala Gln Tyr Gly Gly Ile Ser Ser Arg Asp
                165                 170                 175

Gln Cys Asp Ser Phe Pro Ala Pro Leu Lys Pro Gly Cys Gln Trp Arg
            180                 185                 190

Phe Asp Trp Phe Gln Asn Ala Asp Asn Pro Thr Phe Thr Phe Gln Gln
        195                 200                 205

Val Gln Cys Pro Ala Glu Ile Val Ala Arg Ser Gly Cys Lys Arg Asn
    210                 215                 220

Asp Asp Ser Ser Phe Pro Val Phe Thr Pro Ser Gly Gly Asn Gly
225                 230                 235                 240

Gly Thr Gly Thr Pro Thr Ser Thr Ala Pro Gly Ser Gly Gln Thr Ser
                245                 250                 255

Pro Gly Gly Gly Ser Gly Cys Thr Ser Gln Lys Trp Ala Gln Cys Gly
            260                 265                 270
```

```
Gly Ile Gly Phe Ser Gly Cys Thr Thr Cys Val Ser Gly Thr Thr Cys
            275                 280                 285

Gln Lys Leu Asn Asp Tyr Tyr Ser Gln Cys Leu
    290                 295

<210> SEQ ID NO 17
<211> LENGTH: 278
<212> TYPE: PRT
<213> ORGANISM: Thielavia terrestris

<400> SEQUENCE: 17

Ala Ser Gly Ser Gly Gln Ser Thr Arg Tyr Trp Asp Cys Cys Lys Pro
1               5                   10                  15

Ser Cys Ala Trp Pro Gly Lys Ala Ala Val Ser Gln Pro Val Tyr Ala
            20                  25                  30

Cys Asp Ala Asn Phe Gln Arg Leu Ser Asp Phe Asn Val Gln Ser Gly
        35                  40                  45

Cys Asn Gly Gly Ser Ala Tyr Ser Cys Ala Asp Gln Thr Pro Trp Ala
    50                  55                  60

Val Asn Asp Asn Leu Ala Tyr Gly Phe Ala Ala Thr Ser Ile Ala Gly
65                  70                  75                  80

Gly Ser Glu Ser Ser Trp Cys Cys Ala Cys Tyr Ala Leu Thr Phe Thr
                85                  90                  95

Ser Gly Pro Val Ala Gly Lys Thr Met Val Val Gln Ser Thr Ser Thr
            100                 105                 110

Gly Gly Asp Leu Gly Ser Asn His Phe Asp Ile Ala Met Pro Gly Gly
        115                 120                 125

Gly Val Gly Ile Phe Asn Gly Cys Ser Ser Gln Phe Gly Gly Leu Pro
    130                 135                 140

Gly Ala Gln Tyr Gly Gly Ile Ser Ser Arg Asp Gln Cys Asp Ser Phe
145                 150                 155                 160

Pro Ala Pro Leu Lys Pro Gly Cys Gln Trp Arg Phe Asp Trp Phe Gln
                165                 170                 175

Asn Ala Asp Asn Pro Thr Phe Thr Phe Gln Gln Val Gln Cys Pro Ala
            180                 185                 190

Glu Ile Val Ala Arg Ser Gly Cys Lys Arg Asn Asp Asp Ser Ser Phe
        195                 200                 205

Pro Val Phe Thr Pro Pro Ser Gly Gly Asn Gly Gly Thr Gly Thr Pro
    210                 215                 220

Thr Ser Thr Ala Pro Gly Ser Gly Gln Thr Ser Pro Gly Gly Gly Ser
225                 230                 235                 240

Gly Cys Thr Ser Gln Lys Trp Ala Gln Cys Gly Gly Ile Gly Phe Ser
                245                 250                 255

Gly Cys Thr Thr Cys Val Ser Gly Thr Thr Cys Gln Lys Leu Asn Asp
            260                 265                 270

Tyr Tyr Ser Gln Cys Leu
            275

<210> SEQ ID NO 18
<211> LENGTH: 305
<212> TYPE: PRT
<213> ORGANISM: Thielavia hyrcaniae
```

<400> SEQUENCE: 18

```
Met Arg Ser Thr Pro Val Leu Arg Thr Ala Ile Ala Ala Ala Leu Pro
1               5                   10                  15

Leu Val Ala Phe Ala Ala Asp Gly Lys Ser Thr Arg Tyr Trp Asp Cys
            20                  25                  30

Cys Lys Pro Ser Cys Ala Trp Ser Gly Lys Ala Ala Val Ser Ala Pro
        35                  40                  45

Val Tyr Ala Cys Ser Ala Asn Phe Gln Arg Leu Ser Asp Pro Asn Ala
    50                  55                  60

Lys Ser Gly Cys Asp Gly Gly Ser Ala Tyr Thr Cys Ala Asp Gln Thr
65                  70                  75                  80

Pro Trp Ala Ile Asn Asp Asn Leu Ser Tyr Gly Phe Ala Ala Thr Ser
                85                  90                  95

Ile Ser Gly Gly Ser Glu Ala Ser Trp Cys Cys Ala Cys Tyr Glu Leu
            100                 105                 110

Thr Phe Asn Ser Gly Pro Val Ala Gly Lys Lys Met Val Val Gln Ser
        115                 120                 125

Thr Ser Thr Gly Gly Asp Leu Gly Thr Asn His Phe Asp Leu Asn Ile
130                 135                 140

Pro Gly Gly Gly Val Gly Leu Phe Asp Gly Cys Lys Asn Gln Phe Gly
145                 150                 155                 160

Gly Leu Pro Gly Ala Gln Tyr Gly Gly Ile Ser Ser Arg Ser Gln Cys
                165                 170                 175

Asp Ser Phe Pro Glu Ala Leu Lys Pro Gly Cys Tyr Trp Arg Phe Asp
            180                 185                 190

Trp Phe Gln Asn Ala Asp Asn Pro Thr Phe Thr Phe Arg Gln Val Gln
        195                 200                 205

Cys Pro Ser Glu Leu Val Ala Arg Thr Gly Cys Arg Arg Asn Asp Asp
    210                 215                 220

Ser Ser Phe Pro Val Phe Thr Pro Gly Thr Ser Gly Ser Ser Ser Thr
225                 230                 235                 240

Ala Lys Pro Ala Ser Ser Thr Arg Ala Thr Ser Thr Lys Thr Ser
                245                 250                 255

Ala Pro Ala Thr Gln Thr Ser Ser Thr Gly Gly Gly Cys Val Ala Gln
            260                 265                 270

Lys Trp Ala Gln Cys Gly Gly Ser Gly Phe Ser Gly Cys Thr Thr Cys
        275                 280                 285

Ala Ala Gly Ser Thr Cys Thr Lys Gln Asn Asp Tyr Tyr Ser Gln Cys
    290                 295                 300

Leu
305
```

<210> SEQ ID NO 19
<211> LENGTH: 293
<212> TYPE: PRT
<213> ORGANISM: Chaetomium thermophilum

<400> SEQUENCE: 19

```
Ala Asp Gly Lys Ser Thr Arg Tyr Trp Asp Cys Cys Lys Pro Ser Cys
1               5                   10                  15

Ser Trp Pro Gly Lys Ala Ala Val Ser Gln Pro Val Phe Ala Cys Asp
            20                  25                  30

Arg Asn Phe Asn Arg Ile Tyr Asp Phe Gly Ala Lys Ser Gly Cys Glu
        35                  40                  45
```

Gly Gly Pro Ala Tyr Ser Cys Ala Asp Gln Thr Pro Trp Ala Val Asn
        50                  55                  60

Asp Gln Phe Ser Tyr Gly Phe Ala Ala Thr Asn Ile Ala Gly Gly Asn
 65                  70                  75                  80

Glu Ala Ser Trp Cys Cys Ala Cys Tyr Lys Leu Thr Phe Thr Ser Gly
                     85                  90                  95

Pro Val Ala Gly Lys Val Met Val Val Gln Ser Thr Ser Thr Gly Gly
                100                 105                 110

Asp Leu Gly Asn Asn His Phe Asp Leu Asn Ile Pro Gly Gly Gly Val
            115                 120                 125

Gly Ile Phe Asp Gly Cys Thr Pro Gln Phe Gly Gly Leu Pro Gly Glu
        130                 135                 140

Arg Tyr Gly Gly Ile Ser Ser Arg Ser Gln Cys Asp Ser Phe Pro Asp
145                 150                 155                 160

Ala Leu Lys Pro Gly Cys Tyr Trp Arg Phe Asp Trp Phe Leu Asn Ala
                165                 170                 175

Asp Asn Pro Asn Phe Thr Phe Glu Arg Val Gln Cys Pro Ser Glu Leu
            180                 185                 190

Val Ala Arg Thr Gly Cys Lys Arg Asn Asp Asp Gly Asn Tyr Pro Val
        195                 200                 205

Phe Thr Pro Pro Ser Gly Asp Ser Pro Ser Ser Ser Ala Ala Pro
210                 215                 220

Thr Ser Thr Ser Thr Ser Gln Gln Pro Gln Gln Pro Thr Ser Ser Ser
225                 230                 235                 240

Ser Gln Ala Ser Val Pro Thr Ser Asn Pro Gly Gly Cys Thr Ser Gln
                245                 250                 255

Lys Trp Ala Gln Cys Gly Gly Ile Gly Phe Thr Gly Cys Thr Thr Cys
            260                 265                 270

Val Ser Gly Thr Thr Cys Thr Lys Leu Asn Asp Trp Tyr Ser Gln Cys
        275                 280                 285

Thr Met Ile Asn Leu
        290

<210> SEQ ID NO 20
<211> LENGTH: 235
<212> TYPE: PRT
<213> ORGANISM: Melanocarpus albomyces

<400> SEQUENCE: 20

Met Arg Ser Thr Pro Val Leu Arg Ala Leu Leu Ala Ala Ala Leu Pro
 1               5                  10                  15

Leu Gly Ala Leu Ala Ala Asn Gly Gln Ser Thr Arg Tyr Trp Asp Cys
            20                  25                  30

Cys Lys Pro Ser Cys Gly Trp Arg Gly Lys Gly Pro Val Asn Gln Pro
        35                  40                  45

Val Tyr Ser Cys Asp Ala Asn Phe Gln Arg Ile His Asp Phe Asp Ala
    50                  55                  60

Val Ser Gly Cys Glu Gly Gly Pro Ala Phe Ser Cys Ala Asp His Ser
 65                  70                  75                  80

Pro Trp Ala Ile Asn Asp Asn Leu Ser Tyr Gly Phe Ala Ala Thr Ala
                 85                  90                  95

Leu Ser Gly Gln Thr Glu Glu Ser Trp Cys Cys Ala Cys Tyr Ala Leu
            100                 105                 110

Thr Phe Thr Ser Gly Pro Val Ala Gly Lys Thr Met Val Val Gln Ser
        115                 120                 125

```
Thr Ser Thr Gly Gly Asp Leu Gly Ser Asn His Phe Asp Leu Asn Ile
    130                 135                 140
Pro Gly Gly Val Gly Leu Phe Asp Gly Cys Thr Pro Gln Phe Gly
145                 150                 155                 160
Gly Leu Pro Gly Ala Arg Tyr Gly Gly Ile Ser Ser Arg Gln Glu Cys
                165                 170                 175
Asp Ser Phe Pro Glu Pro Leu Lys Pro Gly Cys Gln Trp Arg Phe Asp
                180                 185                 190
Trp Phe Gln Asn Ala Asp Asn Pro Ser Phe Thr Phe Glu Arg Val Gln
                195                 200                 205
Cys Pro Glu Glu Leu Val Ala Arg Thr Gly Cys Arg Arg His Asp Asp
210                 215                 220
Gly Gly Phe Ala Val Phe Lys Ala Pro Ser Ala
225                 230                 235

<210> SEQ ID NO 21
<211> LENGTH: 306
<212> TYPE: PRT
<213> ORGANISM: unknown
<220> FEATURE:
<223> OTHER INFORMATION: Humicola sp.

<400> SEQUENCE: 21

Pro Phe Met Met Val Ala Trp Trp Ser Leu Phe Leu Tyr Gly Leu Gln
1               5                   10                  15
Val Ala Ala Pro Ala Phe Ala Ala Asp Gly Arg Ser Thr Arg Tyr Trp
                20                  25                  30
Asp Cys Cys Lys Pro Ser Cys Ser Trp Pro Gly Lys Ala Leu Val Asn
                35                  40                  45
Gln Pro Val Tyr Ala Arg Asn Ala Asn Phe Gln Arg Ile Thr Asp Pro
50                  55                  60
Asn Ala Lys Ser Gly Cys Asp Gly Gly Ser Ala Phe Ser Cys Ala Asp
65                  70                  75                  80
Gln Thr Pro Trp Ala Val Ser Asp Asp Phe Ala Tyr Gly Phe Ala Ala
                85                  90                  95
Thr Ala Leu Ala Gly Gln Ser Glu Ser Ser Trp Cys Cys Ala Cys Tyr
                100                 105                 110
Glu Leu Thr Phe Thr Ser Gly Pro Val Ala Gly Lys Lys Met Ala Val
                115                 120                 125
Gln Ser Thr Ser Thr Gly Gly Asp Leu Gly Ser Asn His Phe Asp Leu
                130                 135                 140
Asn Met Pro Gly Gly Gly Val Gly Ile Phe Asp Gly Cys Ser Pro Gln
145                 150                 155                 160
Val Gly Gly Leu Ala Gly Gln Arg Tyr Gly Gly Val Ser Ser Arg Ser
                165                 170                 175
Glu Cys Asp Ser Phe Pro Ala Ala Leu Lys Pro Gly Cys Tyr Trp Arg
                180                 185                 190
Tyr Asp Trp Phe Lys Asn Ala Asp Asn Pro Ser Phe Ser Phe Arg Gln
                195                 200                 205
Val Gln Cys Pro Ala Glu Leu Val Ala Arg Thr Gly Cys Arg Arg Asn
210                 215                 220
Asp Asp Gly Asn Phe Pro Ala Val Gln Ile Pro Ser Ser Ser Thr Ser
225                 230                 235                 240
Ser Pro Val Asn Gln Pro Thr Ser Thr Ser Thr Ser Thr Ser Thr
                245                 250                 255
```

```
Thr Ser Ser Pro Pro Val Gln Pro Thr Thr Pro Ser Gly Cys Thr Ala
            260                 265                 270

Glu Arg Trp Ala Gln Cys Gly Gly Asn Gly Trp Ser Gly Cys Thr Thr
        275                 280                 285

Cys Val Ala Gly Ser Thr Cys Thr Lys Ile Asn Asp Trp Tyr His Gln
    290                 295                 300

Cys Leu
305

<210> SEQ ID NO 22
<211> LENGTH: 299
<212> TYPE: PRT
<213> ORGANISM: Thielavia terrestris NRRL 8126

<400> SEQUENCE: 22

Met Arg Ser Thr Pro Val Leu Arg Thr Thr Leu Ala Ala Ala Leu Pro
1               5                   10                  15

Leu Val Ala Ser Ala Ala Ser Gly Ser Gly Gln Ser Thr Arg Tyr Trp
            20                  25                  30

Asp Cys Cys Lys Pro Ser Cys Ala Trp Pro Gly Lys Ala Ala Val Ser
        35                  40                  45

Gln Pro Val Tyr Ala Cys Asp Ala Asn Phe Gln Arg Leu Ser Asp Phe
    50                  55                  60

Asn Val Gln Ser Gly Cys Asn Gly Gly Ser Ala Tyr Ser Cys Ala Asp
65                  70                  75                  80

Gln Thr Pro Trp Ala Val Asn Asp Asn Leu Ala Tyr Gly Phe Ala Ala
                85                  90                  95

Thr Ser Ile Ala Gly Gly Ser Glu Ser Ser Trp Cys Cys Ala Cys Tyr
            100                 105                 110

Ala Leu Thr Phe Thr Ser Gly Pro Val Ala Gly Lys Thr Met Val Val
        115                 120                 125

Gln Ser Thr Ser Thr Gly Gly Asp Leu Gly Ser Asn Gln Phe Asp Ile
    130                 135                 140

Ala Met Pro Gly Gly Gly Val Gly Ile Phe Asn Gly Cys Ser Ser Gln
145                 150                 155                 160

Phe Gly Gly Leu Pro Gly Ala Gln Tyr Gly Gly Ile Ser Ser Arg Asp
                165                 170                 175

Gln Cys Asp Ser Phe Pro Ala Pro Leu Lys Pro Gly Cys Gln Trp Arg
            180                 185                 190

Phe Asp Trp Phe Gln Asn Ala Asp Asn Pro Thr Phe Thr Phe Gln Gln
        195                 200                 205

Val Gln Cys Pro Ala Glu Ile Val Ala Arg Ser Gly Cys Lys Arg Asn
    210                 215                 220

Asp Asp Ser Ser Phe Pro Val Phe Thr Pro Pro Ser Gly Gly Asn Gly
225                 230                 235                 240

Gly Thr Gly Thr Pro Thr Ser Thr Ala Pro Gly Ser Gly Gln Thr Ser
                245                 250                 255

Pro Gly Gly Gly Ser Gly Cys Thr Ser Gln Lys Trp Ala Gln Cys Gly
            260                 265                 270

Gly Ile Gly Phe Ser Gly Cys Thr Thr Cys Val Ser Gly Thr Thr Cys
        275                 280                 285

Gln Lys Leu Asn Asp Tyr Tyr Ser Gln Cys Leu
    290                 295
```

```
<210> SEQ ID NO 23
<211> LENGTH: 305
<212> TYPE: PRT
<213> ORGANISM: Humicola grisea

<400> SEQUENCE: 23

Met Arg Ser Ser Pro Leu Leu Pro Ser Asp Val Val Ala Ala Leu Pro
1               5                   10                  15

Val Leu Ala Leu Ala Ala Asp Gly Lys Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Leu Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Phe Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Ser Ser Ser Thr Ser Ser
225                 230                 235                 240

Pro Val Gly Gln Pro Thr Ser Thr Ser Thr Thr Ser Thr Ser Thr Thr
                245                 250                 255

Ser Ser Pro Pro Val Gln Pro Thr Thr Pro Ser Gly Cys Thr Ala Glu
            260                 265                 270

Arg Trp Ala Gln Cys Gly Gly Asn Gly Trp Ser Gly Cys Thr Thr Cys
        275                 280                 285

Val Ala Gly Ser Thr Cys Thr Lys Ile Asn Asp Trp Tyr His Gln Cys
    290                 295                 300

Leu
305

<210> SEQ ID NO 24
<211> LENGTH: 315
<212> TYPE: PRT
<213> ORGANISM: unknown
<220> FEATURE:
<223> OTHER INFORMATION: Acremonium sp.

<400> SEQUENCE: 24

Met Arg Ser Ser Pro Phe Leu Arg Ala Ala Leu Ala Ala Ala Leu Pro
1               5                   10                  15
```

```
Leu Ser Ala His Ala Leu Asp Gly Lys Ser Thr Arg Tyr Trp Asp Cys
                20                  25                  30

Cys Lys Pro Ser Cys Gly Trp Ala Gly Lys Ala Ser Val Asn Gln Pro
            35                  40                  45

Val Phe Ser Cys Ser Ala Asp Trp Gln Arg Ile Ser Asp Phe Asn Ala
        50                  55                  60

Lys Ser Gly Cys Asp Gly Gly Ser Ala Tyr Ser Cys Ala Asp Gln Thr
65                  70                  75                  80

Pro Trp Ala Val Asn Asp Asn Phe Ser Tyr Gly Phe Ala Ala Thr Ala
                85                  90                  95

Ile Ala Gly Gly Ser Glu Ser Ser Trp Cys Cys Ala Cys Tyr Ala Leu
            100                 105                 110

Thr Phe Asn Ser Gly Pro Val Ala Gly Lys Thr Met Val Val Gln Ser
        115                 120                 125

Thr Ser Thr Gly Gly Asp Leu Gly Ser Asn Gln Phe Asp Leu Ala Ile
130                 135                 140

Pro Gly Gly Gly Val Gly Ile Phe Asn Gly Cys Ala Ser Gln Phe Gly
145                 150                 155                 160

Gly Leu Pro Gly Ala Gln Tyr Gly Gly Ile Ser Asp Arg Ser Gln Cys
                165                 170                 175

Ser Ser Phe Pro Ala Pro Leu Gln Pro Gly Cys Gln Trp Arg Phe Asp
            180                 185                 190

Trp Phe Gln Asn Ala Asp Asn Pro Thr Phe Thr Phe Gln Arg Val Gln
        195                 200                 205

Cys Pro Ser Glu Leu Thr Ser Arg Thr Gly Cys Lys Arg Asp Asp Asp
210                 215                 220

Ala Ser Tyr Pro Val Phe Asn Pro Pro Ser Val Pro Gly Leu Asp Gly
225                 230                 235                 240

Ser Asn Pro Gly Asn Pro Thr Thr Thr Val Val Pro Ala Ser Thr
                245                 250                 255

Ser Thr Ser Arg Pro Thr Ser Ser Thr Ser Pro Val Ser Thr Pro
            260                 265                 270

Thr Gly Gln Pro Gly Gly Cys Thr Thr Gln Lys Trp Gly Gln Cys Gly
        275                 280                 285

Gly Ile Gly Tyr Thr Gly Cys Thr Asn Cys Val Ala Gly Thr Thr Cys
290                 295                 300

Thr Gln Leu Asn Pro Trp Tyr Ser Gln Cys Leu
305                 310                 315

<210> SEQ ID NO 25
<211> LENGTH: 302
<212> TYPE: PRT
<213> ORGANISM: Podospora anserina

<400> SEQUENCE: 25

Met Arg Ser Ser Thr Val Leu Gln Thr Ser Leu Leu Ala Val Leu Pro
1               5                   10                  15

Leu Ala Val Gln Ala Gln Gly Ala Ser Gly Ser Gly Lys Ser Thr Arg
                20                  25                  30

Tyr Trp Asp Cys Cys Lys Pro Ser Cys Ala Trp Pro Gly Lys Ala Ala
            35                  40                  45

Val Asn Arg Pro Val Phe Ala Cys Asp Ala Asn Phe Gln Arg Ile Ser
        50                  55                  60

Asp Ser Gly Val Ala Ser Gly Cys Asn Gly Gly Ser Ala Tyr Ser Cys
65                  70                  75                  80
```

```
Ala Asp His Ser Ala Trp Ala Ile Asn Asp Asn Leu Ser Tyr Gly Phe
                85                  90                  95

Ala Ala Thr Ala Leu Ser Gly Gly Ser Glu Ala Ser Trp Cys Cys Ala
            100                 105                 110

Cys Tyr Glu Leu Thr Phe Thr Asp Gly Pro Val Ala Gly Lys Lys Met
            115                 120                 125

Val Val Gln Ser Thr Ser Thr Gly Gly Asp Leu Gly Ser Asn His Phe
        130                 135                 140

Asp Leu Asn Ile Pro Gly Gly Gly Val Gly Leu Phe Asp Gly Cys Lys
145                 150                 155                 160

Pro Gln Phe Gly Gly Leu Pro Gly Ala Thr Tyr Gly Gly Ile Ser Asp
                165                 170                 175

Arg Ser Gln Cys Ala Ser Phe Pro Asp Ala Leu Lys Pro Gly Cys Asn
            180                 185                 190

Trp Arg Phe Asp Trp Phe Lys Asn Ala Asp Asn Pro Ser Phe Thr Phe
        195                 200                 205

Arg Gln Val Gln Cys Pro Ser Glu Leu Thr Ala Arg Ser Gly Cys Lys
        210                 215                 220

Arg Asp Asp Asp Ser Arg Phe Pro Val Phe Ser Pro Pro Gly Gly Gly
225                 230                 235                 240

Ser Gln Pro Gln Pro Gln Pro Thr Ser Ser Ala Ala Gln Asn Pro Asn
                245                 250                 255

Pro Thr Pro Ser Ala Ala Pro Gly Gly Cys Arg Ala Ala Lys Tyr Ala
            260                 265                 270

Gln Cys Gly Gly Gln Gly Phe Thr Gly Cys Thr Thr Cys Glu Ala Gly
            275                 280                 285

Ser Thr Cys Thr Ala Ser Asn Gln Trp Tyr Ser Gln Cys Leu
        290                 295                 300

<210> SEQ ID NO 26
<211> LENGTH: 232
<212> TYPE: PRT
<213> ORGANISM: Acremonium chrysogenum ATCC11550

<400> SEQUENCE: 26

Met Thr Pro Ser Val Phe Lys Ile Ala Leu Ala Ala Ala Ser Val Ala
1               5                   10                  15

Ala Pro Ala Leu Ala Ala Glu Gly Ala Gly Lys Ser Thr Arg Tyr Trp
                20                  25                  30

Asp Cys Cys Lys Pro Ser Cys Ala Trp Pro Glu Lys Ala Asp Val Ser
            35                  40                  45

Ala Pro Ala Ala Val Cys Asn Ala Asp Asn Thr Pro Leu Asn Asp Pro
        50                  55                  60

Leu Ala Asp Ser Gly Cys Asp Gly Gly Pro Ala Phe Thr Cys Ala Asn
65                  70                  75                  80

Tyr Ser Pro Trp Ala Val Asn Asp Asn Leu Ala Tyr Gly Phe Ala Ala
                85                  90                  95

Thr Ala Ile Asn Gly Gly Ser Glu Ala Ser Trp Cys Cys Ala Cys Tyr
            100                 105                 110

Arg Leu Thr Phe Thr Asp Gly Pro Val Ala Gly Lys Thr Met Ile Val
            115                 120                 125

Gln Ser Thr Asn Thr Gly Gly Asp Ile Ser Asn Asn His Phe Asp Ile
        130                 135                 140

Leu Met Pro Gly Gly Gly Val Gly Leu Phe Asp Gly Cys Thr Pro Gln
145                 150                 155                 160
```

```
Tyr Gly Gly Ile Pro Gly Ala Gln Tyr Gly Val Ser Ser Arg Glu
            165                 170                 175

Glu Cys Glu Gln Met Pro Glu Ala Leu Lys Glu Gly Cys Phe Trp Arg
        180                 185                 190

Phe Asp Trp Phe Ala Asn Ala Asp Asn Pro Asn Leu Asn Phe Glu Gln
            195                 200                 205

Val Gln Cys Pro Ser Glu Ile Thr Ala Ile Ser Gly Cys Thr Arg Ser
210                 215                 220

Asp Asp Gly Asn Phe Pro Ala Ala
225                 230
```

<210> SEQ ID NO 27
<211> LENGTH: 304
<212> TYPE: PRT
<213> ORGANISM: unknown
<220> FEATURE:
<223> OTHER INFORMATION: Humicola sp.

<400> SEQUENCE: 27

```
Met Met Val Ala Trp Trp Ser Leu Phe Leu Tyr Gly Leu Gln Val Ala
1               5                   10                  15

Ala Pro Ala Phe Ala Ala Asp Gly Arg Ser Thr Arg Tyr Trp Asp Cys
            20                  25                  30

Cys Lys Pro Ser Cys Ala Trp Ser Gly Lys Ala Ser Val Ser Ser Pro
        35                  40                  45

Val Arg Thr Cys Asp Ala Asn Asn Ser Pro Leu Ser Asp Val Asp Ala
    50                  55                  60

Lys Ser Ala Cys Asp Gly Gly Val Ala Tyr Thr Cys Ser Asn Asn Ala
65                  70                  75                  80

Pro Trp Ala Val Asn Asp Asn Leu Ser Tyr Gly Phe Ala Ala Thr Ala
                85                  90                  95

Ile Asn Gly Gly Ser Glu Ser Ser Trp Cys Cys Ala Cys Tyr Lys Leu
            100                 105                 110

Thr Phe Thr Ser Gly Pro Ala Ser Gly Lys Val Met Val Val Gln Ser
        115                 120                 125

Thr Asn Thr Gly Tyr Asp Leu Ser Asn Asn His Phe Asp Ile Leu Met
    130                 135                 140

Pro Gly Gly Gly Val Gly Ala Phe Asp Gly Cys Ser Arg Gln Tyr Gly
145                 150                 155                 160

Ser Ile Pro Gly Glu Arg Tyr Gly Gly Val Thr Ser Arg Asp Gln Cys
                165                 170                 175

Asp Gln Met Pro Ser Ala Leu Lys Gln Gly Cys Tyr Trp Arg Phe Asp
            180                 185                 190

Trp Phe Lys Asn Ala Asp Asn Pro Ser Phe Ser Phe Arg Gln Val Gln
        195                 200                 205

Cys Pro Ala Glu Leu Val Ala Arg Thr Gly Cys Arg Arg Asn Asp Asp
    210                 215                 220

Gly Asn Phe Pro Ala Val Gln Ile Pro Ser Ser Thr Ser Ser Pro
225                 230                 235                 240

Val Asn Gln Pro Thr Ser Thr Ser Thr Ser Thr Ser
                245                 250                 255

Ser Pro Pro Val Gln Pro Thr Pro Ser Gly Cys Thr Ala Glu Arg
                260                 265                 270
```

```
Trp Ala Gln Cys Gly Gly Asn Gly Trp Ser Gly Cys Thr Thr Cys Val
            275                 280                 285
Ala Gly Ser Thr Cys Thr Lys Ile Asn Asp Trp Tyr His Gln Cys Leu
            290                 295                 300

<210> SEQ ID NO 28
<211> LENGTH: 307
<212> TYPE: PRT
<213> ORGANISM: unknown
<220> FEATURE:
<223> OTHER INFORMATION: Humicola sp.

<400> SEQUENCE: 28

Pro Phe Met Met Val Ala Trp Trp Ser Leu Phe Leu Tyr Gly Leu Gln
1               5                   10                  15

Val Ala Ala Pro Ala Phe Ala Ala Asp Gly Arg Ser Thr Arg Tyr Trp
            20                  25                  30

Asp Cys Cys Lys Pro Ser Cys Ser Trp Pro Asp Lys Ala Pro Val Gly
            35                  40                  45

Ser Pro Val Gly Thr Cys Asp Ala Gly Asn Ser Pro Leu Gly Asp Pro
        50                  55                  60

Leu Ala Lys Ser Gly Cys Glu Gly Gly Pro Ser Tyr Thr Cys Ala Asn
65                  70                  75                  80

Tyr Gln Pro Trp Ala Val Asn Asp Gln Leu Ala Tyr Gly Phe Ala Ala
                85                  90                  95

Thr Ala Ile Asn Gly Gly Thr Glu Asp Ser Trp Cys Cys Ala Cys Tyr
            100                 105                 110

Lys Leu Thr Phe Thr Asp Gly Pro Ala Ser Gly Lys Thr Met Ile Val
            115                 120                 125

Gln Ser Thr Asn Thr Gly Gly Asp Leu Ser Asp Asn His Phe Asp Leu
        130                 135                 140

Leu Ile Pro Gly Gly Gly Val Gly Ile Phe Asp Gly Cys Thr Ser Gln
145                 150                 155                 160

Tyr Gly Gln Ala Leu Pro Gly Ala Gln Tyr Gly Gly Val Ser Ser Arg
                165                 170                 175

Ala Glu Cys Asp Gln Met Pro Glu Ala Ile Lys Ala Gly Cys Gln Trp
            180                 185                 190

Arg Tyr Asp Trp Phe Lys Asn Ala Asp Asn Pro Ser Phe Ser Phe Arg
            195                 200                 205

Gln Val Gln Cys Pro Ala Glu Leu Val Ala Arg Thr Gly Cys Arg Arg
        210                 215                 220

Asn Asp Asp Gly Asn Phe Pro Ala Val Gln Ile Pro Ser Ser Ser Thr
225                 230                 235                 240

Ser Ser Pro Val Asn Gln Pro Thr Ser Thr Ser Thr Ser Thr Ser Thr
                245                 250                 255

Thr Thr Ser Ser Pro Pro Val Gln Pro Thr Thr Pro Ser Gly Cys Thr
            260                 265                 270

Ala Glu Arg Trp Ala Gln Cys Gly Gly Asn Gly Trp Ser Gly Cys Thr
            275                 280                 285

Thr Cys Val Ala Gly Ser Thr Cys Thr Lys Ile Asn Asp Trp Tyr His
        290                 295                 300

Gln Cys Leu
305
```

```
<210> SEQ ID NO 29
<211> LENGTH: 277
<212> TYPE: PRT
<213> ORGANISM: Scytalidium indonesiacum

<400> SEQUENCE: 29

Met Arg Ser Ser Pro Leu Leu Arg Ser Ala Val Val Ala Ala Leu Pro
1               5                   10                  15

Val Leu Ala Leu Ala Ala Asp Gly Lys Ser Thr Arg Tyr Trp Asp Cys
                20                  25                  30

Cys Lys Pro Ser Cys Gly Trp Ala Lys Lys Ala Pro Val Asn Gln Pro
            35                  40                  45

Val Phe Ser Cys Asn Ala Asn Phe Gln Arg Leu Tyr Asp Phe Asp Ala
        50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Phe Gly Phe Ala Ala Thr
                85                  90                  95

Ser Ile Ala Gly Ser Asn Glu Ala Gly Trp Cys Cys Ala Cys Tyr Glu
                100                 105                 110

Leu Thr Phe Thr Ser Gly Pro Val Ala Gly Lys Lys Met Val Val Gln
            115                 120                 125

Ser Thr Ser Thr Gly Gly Asp Leu Gly Ser Asn His Phe Asp Leu Asn
130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Glu Arg Phe Pro Asp Ala Leu Lys Pro Gly Cys Tyr Trp Arg Phe
            180                 185                 190

Asp Trp Phe Lys Asn Ala Asp Asn Pro Asn Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Ser Ser Ser Thr Ser Ser
225                 230                 235                 240

Pro Arg Ile Gln Asn Leu Gly Ser Thr Arg Met Leu Ser Arg Ser Arg
                245                 250                 255

Arg Arg Arg Pro Ala Gly Gly Ser Gln Leu Ala Ala Ala Gly Gly Val
            260                 265                 270

Arg Gly Gly Ala Pro
            275
```